US010872696B2

(12) United States Patent
Bernstein et al.

(10) Patent No.: US 10,872,696 B2
(45) Date of Patent: Dec. 22, 2020

(54) METHOD OF HYPOGLYCEMIA RISK DETERMINATION

(71) Applicant: ABBOTT DIABETES CARE INC., Alameda, CA (US)

(72) Inventors: Daniel M. Bernstein, El Granada, CA (US); Kenneth J. Doniger, Menlo Park, CA (US); Timothy C. Dunn, San Francisco, CA (US); Gary A. Hayter, Oakland, CA (US); Howard Wolpert, Brookline, MA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 733 days.

(21) Appl. No.: 15/427,586

(22) Filed: Feb. 8, 2017

(65) Prior Publication Data

US 2017/0147769 A1 May 25, 2017

Related U.S. Application Data

(63) Continuation of application No. 13/984,806, filed as application No. PCT/US2011/066610 on Dec. 21, 2011, now abandoned.

(60) Provisional application No. 61/486,117, filed on May 13, 2011, provisional application No. 61/442,085, filed on Feb. 11, 2011.

(51) Int. Cl.
*G16H 50/20* (2018.01)
*G16H 40/63* (2018.01)
*G16H 10/20* (2018.01)
*G06F 19/00* (2018.01)
*A61B 5/00* (2006.01)
*A61B 5/145* (2006.01)
*A61B 5/151* (2006.01)
*G16H 50/30* (2018.01)
*A61B 5/15* (2006.01)

(52) U.S. Cl.
CPC ........... *G16H 50/20* (2018.01); *A61B 5/0022* (2013.01); *A61B 5/14532* (2013.01); *A61B 5/14546* (2013.01); *A61B 5/151* (2013.01); *A61B 5/150358* (2013.01); *A61B 5/486* (2013.01); *A61B 5/4839* (2013.01); *A61B 5/6898* (2013.01); *A61B 5/7275* (2013.01); *A61B 5/742* (2013.01); *A61B 5/743* (2013.01); *A61B 5/7475* (2013.01); *G06F 19/3418* (2013.01); *G06F 19/3468* (2013.01); *G16H 10/20* (2018.01); *G16H 40/63* (2018.01); *G16H 50/30* (2018.01)

(58) Field of Classification Search
None
See application file for complete search history.

(56) References Cited

U.S. PATENT DOCUMENTS

| | | |
|---|---|---|
| 4,545,382 A | 10/1985 | Higgins et al. |
| 4,711,245 A | 12/1987 | Higgins et al. |
| 5,262,035 A | 11/1993 | Gregg et al. |
| 5,262,305 A | 11/1993 | Heller et al. |
| 5,264,104 A | 11/1993 | Gregg et al. |
| 5,320,725 A | 6/1994 | Gregg et al. |
| 5,356,249 A | 10/1994 | Heller et al. |
| 5,509,410 A | 4/1996 | Hill et al. |
| 5,536,249 A | 7/1996 | Castellano et al. |
| 5,543,236 A | 8/1996 | Heller et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 5,925,021 A | 7/1999 | Castellano et al. |
| 6,071,391 A | 6/2000 | Gotoh et al. |
| 6,103,033 A | 8/2000 | Say et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,281,006 B1 | 8/2001 | Heller et al. |
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,600,997 B2 | 7/2003 | Deweese et al. |

(Continued)

OTHER PUBLICATIONS

WO, PCT/US2011/066610 ISR and Written Opinion, dated Apr. 30, 2012.
Barker, N., "A Practical Introduction to the Bootstrap Using the SAS System", SAS Conference Proceedings, 2005, Paper PK02, 17 pages.
Benton, D., et al., "Performance of the Parametric Bootstrap Method in Small Sample Interval Estimates", Adv. & Appl. in Stat., 2002, vol. 2, No. 3, pp. 269-285.

(Continued)

*Primary Examiner* — G Steven Vanni
(74) *Attorney, Agent, or Firm* — One LLP

(57) ABSTRACT

Presented herein are one or more software applications to help a user manager their diabetes. Embodiments and descriptions of the various applications are provided below in conjunction with an analyte measurement device.

27 Claims, 60 Drawing Sheets

(56) References Cited

U.S. PATENT DOCUMENTS

| | | |
|---|---|---|
| 6,605,200 B1 | 8/2003 | Mao et al. |
| 6,605,201 B1 | 8/2003 | Mao et al. |
| 6,616,819 B1 | 9/2003 | Liamos et al. |
| 6,618,934 B1 | 9/2003 | Feldman et al. |
| 6,638,716 B2 | 10/2003 | Heller et al. |
| 6,650,471 B2 | 11/2003 | Doi |
| 6,654,625 B1 | 11/2003 | Say et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,932,892 B2 | 8/2005 | Chen et al. |
| 6,932,894 B2 | 8/2005 | Mao et al. |
| 6,942,518 B2 | 9/2005 | Liamos et al. |
| 7,041,468 B2 | 5/2006 | Drucker et al. |
| 7,167,818 B2 | 1/2007 | Brown |
| 7,299,082 B2 | 11/2007 | Feldman et al. |
| 7,766,829 B2 | 8/2010 | Sloan et al. |
| 7,866,026 B1 | 1/2011 | Wang et al. |
| 8,262,874 B2 | 9/2012 | Forrow et al. |
| 8,514,086 B2 | 8/2013 | Harper et al. |
| 8,601,465 B2 | 12/2013 | Bernstein et al. |
| 9,913,599 B2 | 3/2018 | Bernstein et al. |
| 2003/0208110 A1 | 11/2003 | Mault et al. |
| 2004/0054263 A1 | 3/2004 | Moerman |
| 2004/0186365 A1 | 9/2004 | Jin et al. |
| 2004/0254434 A1 | 12/2004 | Goodnow et al. |
| 2005/0101841 A9 | 5/2005 | Kaylor et al. |
| 2005/0182306 A1 | 8/2005 | Sloan |
| 2006/0025662 A1 | 2/2006 | Buse et al. |
| 2006/0040402 A1 | 2/2006 | Brauker et al. |
| 2006/0091006 A1 | 5/2006 | Wang et al. |
| 2006/0173260 A1 | 8/2006 | Gaoni et al. |
| 2006/0224141 A1 | 10/2006 | Rush et al. |
| 2007/0056858 A1 | 3/2007 | Chen et al. |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0199818 A1 | 8/2007 | Petyt et al. |
| 2007/0227911 A1 | 10/2007 | Wang et al. |
| 2007/0233013 A1 | 10/2007 | Schoenberg |
| 2008/0066305 A1 | 3/2008 | Wang et al. |
| 2008/0081977 A1 | 4/2008 | Hayter et al. |
| 2008/0102441 A1 | 5/2008 | Chen et al. |
| 2008/0119705 A1 | 5/2008 | Patel et al. |
| 2008/0148873 A1 | 6/2008 | Wang |
| 2008/0161666 A1 | 7/2008 | Feldman et al. |
| 2008/0234992 A1 | 9/2008 | Ray et al. |
| 2008/0249470 A1 | 10/2008 | Malave et al. |
| 2008/0267823 A1 | 10/2008 | Wang et al. |
| 2009/0054748 A1 | 2/2009 | Feldman |
| 2009/0095625 A1 | 4/2009 | Forrow |
| 2009/0164251 A1 | 6/2009 | Hayter |
| 2009/0171589 A1 | 7/2009 | Kovatchev |
| 2009/0240128 A1 | 9/2009 | Mensinger et al. |
| 2009/0247857 A1 | 10/2009 | Harper et al. |
| 2009/0253970 A1 | 10/2009 | Bashan et al. |
| 2009/0255811 A1 | 10/2009 | Forrow et al. |
| 2009/0294277 A1 | 12/2009 | Thomas et al. |
| 2010/0081909 A1 | 4/2010 | Budiman et al. |
| 2010/0198034 A1 | 8/2010 | Thomas et al. |
| 2010/0198142 A1 | 8/2010 | Sloan et al. |
| 2010/0213057 A1 | 8/2010 | Feldman et al. |
| 2010/0222648 A1 | 9/2010 | Tan |
| 2010/0230285 A1 | 9/2010 | Hoss et al. |
| 2010/0256047 A1 | 10/2010 | Sieh et al. |
| 2010/0274592 A1 | 10/2010 | Nitzan et al. |
| 2010/0312577 A1 | 12/2010 | Goodnow et al. |
| 2010/0313105 A1 | 12/2010 | Nekoomaram et al. |
| 2010/0324392 A1 | 12/2010 | Yee et al. |
| 2010/0325868 A1 | 12/2010 | Wang et al. |
| 2010/0326842 A1 | 12/2010 | Mazza et al. |
| 2011/0015511 A1 | 1/2011 | Bousamra et al. |
| 2011/0021889 A1 | 1/2011 | Hoss et al. |
| 2011/0082484 A1 | 4/2011 | Saravia et al. |
| 2011/0098548 A1 | 4/2011 | Budiman et al. |
| 2011/0106126 A1 | 5/2011 | Love et al. |
| 2011/0119080 A1 | 5/2011 | Hayter et al. |
| 2011/0125530 A1 | 5/2011 | Drucker et al. |
| 2011/0160544 A1 | 6/2011 | Hayter |
| 2011/0184264 A1 | 7/2011 | Galasso et al. |
| 2011/0190603 A1 | 8/2011 | Stafford |
| 2011/0191044 A1 | 8/2011 | Stafford |
| 2011/0213225 A1 | 9/2011 | Bernstein et al. |
| 2011/0256024 A1 | 10/2011 | Cole et al. |
| 2011/0319729 A1 | 12/2011 | Donnay et al. |
| 2012/0157801 A1 | 6/2012 | Hoss et al. |
| 2014/0088392 A1 | 3/2014 | Bernstein et al. |
| 2014/0142981 A1 | 5/2014 | Gopal et al. |

OTHER PUBLICATIONS

Clarke, W., et al., "Statistical Tools to Analyze Continuous Glucose Monitor Data", Diabetes Technology & Therapeutics, 2009, vol. 11, Supplement 1, pp. S45-S54.

Nathan, D. M., et al., "Translating the A1C Assay Into Estimated Average Glucose Values", Diabetes Care, 2008, vol. 31, No. 8, pp. 1473-1478.

Rodbard, D., "Interpretation of Continuous Glucose Monitoring Date: Glycemic Variability and Quality of Glycemic Control", Diabetes Technology & Therapeutics, 2009, vol. 11, Supplement 1, pp. S55-S67.

The Diabetes Control and Complications Trial Research Group, "The Effect of Intensive Treatment of Diabetes on the Development and Progression of Long-Term Complications in Insulin-Dependent Diabetes Mellitus", The New England Journal od Medicine, 1993, vol. 329, No. 14, pp. 977-986.

| 4 | Glucose control targets achieved for hypoglycemia, variability and mean glucose exposure. | |
|---|---|---|
| 3 | Reduce mean glucose exposure. | A. Both Day and Night above target.<br>　i. Day = Night<br>　ii. Night > Day<br>　iii. Day > Night |
| | | B. Night only above target. |
| | | C. Day only above target. |
| 2 | Reduce glucose volatility. | A. Both Day and Night above target. |
| | | B. Night only above target. |
| | | C. Day only above target. |
| 1 | Reduce hypoglycemia. | A. Both Day and Night above target. |
| | | B. Night only above target. |
| | | C. Day only above target. |
| 0 | Increase glucose monitoring. | Insufficient monitoring is available to assess control level. |

FIG. 2

| Assessment Schedule | Early Sleep 11pm-3am | Late Sleep 3am-7am | Morning 7am-11am | Midday 11am-4pm | Evening 4pm-11pm |
|---|---|---|---|---|---|
| Hypoglycemia | X | XX | | X | |
| Volatility | X | XX | | | XX |
| Excess Exposure | | X | XX | | XX |

X = Collect a measurement on 5 of 14 days.
XX = Collect a measurement on 10 of 14 days.

FIG. 15

Contingency Table
Day By Hypo

| Count<br>Total %<br>Col %<br>Row%<br>Expected<br>Deviation<br>Cell Chi^2 | 1_Y | 2_N | 3_unk | |
|---|---|---|---|---|
| 1_Sun | 54<br>2.05<br>25.84<br>14.06<br>30.4<br>23.6<br>18.3211 | 224<br>8.48<br>12.90<br>58.33<br>252.655<br>-28.655<br>3.2498 | 106<br>4.02<br>15.27<br>27.60<br>100.945<br>5.05455<br>0.2531 | 384<br>14.55 |
| 2_Mon | 18<br>0.068<br>8.61<br>4.69<br>30.4<br>-12.4<br>5.05749 | 235<br>8.90<br>13.53<br>61.20<br>252.655<br>-17.655<br>1.2336 | 131<br>4.96<br>18.88<br>34.11<br>100.945<br>30.0545<br>8.9482 | 384<br>14.55 |
| 3_Tue | 19<br>0.72<br>9.09<br>5.28<br>28.5<br>-9.5<br>3.1667 | 257<br>9.73<br>14.80<br>71.39<br>236.864<br>20.1364<br>1.7118 | 84<br>3.18<br>12.10<br>23.33<br>94.6364<br>-10.636<br>1.1954 | 360<br>13.64 |
| 4_Wed | 24<br>0.91<br>11.48<br>6.67<br>28.5<br>-4.5<br>0.7105 | 254<br>9.62<br>14.62<br>70.56<br>236.864<br>17.1364<br>1.2398 | 85<br>3.11<br>11.82<br>22.78<br>94.6364<br>-12.636<br>1.6873 | 360<br>13.64 |
| 5_Thu | 20<br>0.76<br>9.57<br>5.21<br>30.4<br>-10.4<br>3.5579 | 256<br>9.70<br>14.74<br>6.667<br>252.655<br>3.34545<br>0.0443 | 108<br>4.09<br>15.56<br>28.13<br>100.945<br>7.05455<br>0.4930 | 384<br>14.55 |
| 6_Fri | 26<br>0.98<br>12.44<br>6.77<br>30.4<br>-4.4<br>0.6368 | 276<br>10.45<br>15.89<br>71.88<br>252.655<br>23.3455<br>2.1571 | 82<br>3.11<br>11.82<br>21.35<br>100.945<br>-18.945<br>3.5557 | 384<br>14.55 |
| 7_Sat | 48<br>1.82<br>22.97<br>12.50<br>30.4<br>17.6<br>10.1895 | 235<br>8.90<br>13.53<br>61.20<br>252.655<br>-17.655<br>1.2336 | 101<br>3.83<br>14.55<br>26.30<br>100.945<br>0.05455<br>0.0000 | 384<br>14.55 |
| | 209<br>7.92 | 1737<br>65.80 | 694<br>26.29 | 2640 |

Tests

| Source | DF | -LogLike | Rsquare (U) |
|---|---|---|---|
| Model | 12 | 32.5673 | 0.0149 |
| Error | 2626 | 2151.8676 | |
| C. Total | 2638 | 2184.4349 | |
| N | 2640 | | |

| Test | ChiSquare | Prob>ChiSq |
|---|---|---|
| Likelihood Ratio | 65.135 | <.0001 |
| Pearson | 68.643 | <.0001 |

FIG. 19

(sorting is based 1st of Deviation, then on chi-squared)

| Day | Expect Hypo Rate (count) | Observed Hypo Rate (count) | Deviation | Chi-squared |
|---|---|---|---|---|
| 1_Sun | 30.4 | 54 | 23.6 | 18.3211 |
| 7_Sat | 30.4 | 48 | 17.6 | 10.1895 |
| 6_Fri | 30.4 | 26 | -4.4 | 0.6368 |
| 4_Wed | 28.5 | 24 | -4.5 | 0.7105 |
| 3_Tue | 28.5 | 19 | -9.5 | 3.1667 |
| 5_Thu | 30.4 | 20 | -10.4 | 3.5579 |
| 2_Mon | 30.4 | 18 | -12.4 | 5.0579 |

FIG. 20

Contingency Table
Day By Hypo

| Count<br>Total %<br>Col %<br>Row%<br>Expected<br>Deviation<br>Cell Chi^2 | 1_Y | 2_N | 3_unk | |
|---|---|---|---|---|
| 1 Sunday | 13<br>0.49<br>26.53<br>3.39<br>7.12727<br>5.87273<br>4.8390 | 43<br>1.63<br>13.61<br>11.20<br>45.9636<br>-2.9636<br>0.1911 | 328<br>12.42<br>14.42<br>85.42<br>330.909<br>-2.9091<br>0.0256 | 384<br>14.55 |
| 2 Monday | 4<br>0.15<br>8.16<br>1.04<br>7.12727<br>-3.1273<br>1.3722 | 48<br>1.82<br>15.19<br>12.50<br>45.9636<br>2.03636<br>0.0902 | 332<br>12.58<br>14.59<br>86.46<br>330.909<br>1.09091<br>0.0036 | 384<br>14.55 |
| 3 Tuesday | 6<br>0.23<br>12.24<br>1.67<br>6.68182<br>-0.6818<br>0.0696 | 41<br>1.55<br>12.97<br>11.39<br>43.0909<br>-2.0909<br>0.1015 | 313<br>11.86<br>13.76<br>86.94<br>310.227<br>2.77273<br>0.0248 | 360<br>13.64 |
| 4 Wednesday | 7<br>0.27<br>14.29<br>1.94<br>6.68182<br>0.31818<br>0.0152 | 49<br>1.86<br>15.51<br>13.61<br>43.0909<br>5.90909<br>0.8103 | 304<br>11.52<br>13.36<br>84.44<br>310.227<br>-6.2273<br>0.1250 | 360<br>13.64 |
| 5 Thursday | 3<br>0.11<br>6.12<br>0.78<br>7.12727<br>-4.1273<br>2.3900 | 47<br>1.78<br>14.87<br>12.24<br>45.9636<br>1.03636<br>0.0234 | 334<br>12.65<br>14.68<br>86.98<br>330.909<br>3.09091<br>0.0289 | 384<br>14.55 |
| 6 Friday | 5<br>0.19<br>10.20<br>1.30<br>7.12727<br>-2.1273<br>0.6349 | 39<br>1.48<br>12.34<br>10.16<br>45.9636<br>-6.9636<br>1.0550 | 340<br>12.88<br>14.95<br>88.54<br>330.909<br>9.09091<br>0.2498 | 384<br>14.55 |
| 7 Saturday | 11<br>0.42<br>22.45<br>2.86<br>7.12727<br>3.87273<br>2.1043 | 49<br>1.86<br>15.51<br>12.76<br>459636<br>3.03636<br>0.2006 | 324<br>12.27<br>14.24<br>84.38<br>330.909<br>-6.9091<br>0.1443 | 384<br>14.55 |
|  | 49<br>1.86 | 316<br>11.97 | 2275<br>86.17 | 2640 |

Tests

| Source | DF | -LogLike | Rsquare (U) |
|---|---|---|---|
| Model | 12 | 7.1361 | 0.0059 |
| Error | 2626 | 1197.5325 | |
| C. Total | 2638 | 1204.6687 | |
| N | 2640 | | |

| Test | ChiSquare | Prob>ChiSq |
|---|---|---|
| Likelihood Ratio | 14.272 | 0.2837 |
| Pearson | 14.499 | 0.2700 |

FIG. 22

Table 1: Episodes detected for a patient for 4 calendar days.

| Episode Type | Day | Start | End | Lowest Value | Duration | CGM Alarm? | Source |
|---|---|---|---|---|---|---|---|
| Rise | Saturday | 11/04/2006 08:56 | 11/04/2006 09:26 | 118 | 30 | Yes | CGM |
| Fall | Saturday | 11/04/2006 09:56 | 11/04/2006 10:36 | 173 | 40 | Yes | CGM |
| Rise | Saturday | 11/04/2006 10:36 | 11/04/2006 12:06 | 68 | 90 | Yes | CGM |
| High | Saturday | 11/04/2006 11:41 | 11/04/2006 11:41 | 223 | 0 | Yes | SMBG |
| Fall | Saturday | 11/04/2006 12:06 | 11/04/2006 13:26 | 218 | 80 | Yes | CGM |
| Rise | Saturday | 11/04/2006 13:26 | 11/04/2006 14:06 | 54 | 40 | Yes | CGM |
| Fall | Saturday | 11/04/2006 14:06 | 11/04/2006 15:06 | 153 | 60 | Yes | CGM |
| Rise | Saturday | 11/04/2006 15:06 | 11/04/2006 16:26 | 74 | 80 | Yes | CGM |
| Rise | Sunday | 11/05/2006 06:57 | 11/05/2006 08:37 | 106 | 100 | Yes | CGM |
| Fall | Sunday | 11/05/2006 10:27 | 11/05/2006 11:57 | 184 | 90 | Yes | CGM |
| Rise | Sunday | 11/05/2006 11:57 | 11/05/2006 12:27 | 85 | 30 | Yes | CGM |
| Rise | Sunday | 11/05/2006 14:57 | 11/05/2006 16:07 | 125 | 70 | Yes | CGM |
| Fall | Sunday | 11/05/2006 17:27 | 11/05/2006 18:28 | 178 | 60 | Yes | CGM |
| Rise | Monday | 11/13/2006 21:16 | 11/13/2006 22:26 | 54 | 70 | Yes | CGM |
| Low | Tuesday | 11/14/2006 02:56 | 11/14/2006 04:46 | 46 | 110 | Yes | CGM |
| Low | Tuesday | 11/14/2006 05:56 | 11/14/2006 06:26 | 57 | 30 | Yes | CGM |
| Low | Tuesday | 11/14/2006 07:04 | 11/14/2006 07:04 | 60 | 0 | Yes | SMBG |
| Rise | Tuesday | 11/14/2006 07:16 | 11/14/2006 08:17 | 64 | 60 | Yes | CGM |
| Rise | Tuesday | 11/14/2006 12:57 | 11/14/2006 13:57 | 65 | 60 | No | CGM |

FIG. 23

Table 1: Episodes detected and allocated for a patient for 4 calendar days.

| Episode Type | Allocation | Day | Start | End | Lowest Value | Duration | CGM Alarm? | Source |
|---|---|---|---|---|---|---|---|---|
| Rise | Initiator | Saturday | 11/04/2006 08:56 | 11/04/2006 09:26 | 118 | 30 | Yes | CGM |
| Fall | Follow-on | Saturday | 11/04/2006 09:56 | 11/04/2006 10:36 | 173 | 40 | Yes | CGM |
| Rise | Follow-on | Saturday | 11/04/2006 10:36 | 11/04/2006 12:06 | 68 | 90 | Yes | CGM |
| High | Follow-on | Saturday | 11/04/2006 11:41 | 11/04/2006 11:41 | 223 | 0 | Yes | SMBG |
| Fall | Follow-on | Saturday | 11/04/2006 12:06 | 11/04/2006 13:26 | 218 | 80 | Yes | CGM |
| Rise | Follow-on | Saturday | 11/04/2006 13:26 | 11/04/2006 14:06 | 54 | 40 | Yes | CGM |
| Fall | Follow-on | Saturday | 11/04/2006 14:06 | 11/04/2006 15:06 | 153 | 60 | Yes | CGM |
| Rise | Follow-on | Saturday | 11/04/2006 15:06 | 11/04/2006 16:26 | 74 | 80 | Yes | CGM |
| Rise | Initiator | Sunday | 11/05/2006 06:57 | 11/05/2006 08:37 | 106 | 100 | Yes | CGM |
| Fall | Follow-on | Sunday | 11/05/2006 10:27 | 11/05/2006 11:57 | 184 | 90 | Yes | CGM |
| Rise | Follow-on | Sunday | 11/05/2006 11:57 | 11/05/2006 12:27 | 85 | 30 | Yes | CGM |
| Fall | Follow-on | Sunday | 11/05/2006 14:57 | 11/05/2006 16:07 | 125 | 70 | Yes | CGM |
| Rise | Follow-on | Sunday | 11/05/2006 17:27 | 11/05/2006 18:28 | 178 | 60 | Yes | CGM |
| Fall | Initiator | Monday | 11/13/2006 21:16 | 11/13/2006 22:26 | 54 | 70 | Yes | CGM |
| Low | Follow-on | Tuesday | 11/14/2006 02:56 | 11/14/2006 04:46 | 46 | 110 | Yes | CGM |
| Low | Follow-on | Tuesday | 11/14/2006 05:56 | 11/14/2006 06:26 | 57 | 30 | Yes | CGM |
| Low | Follow-on | Tuesday | 11/14/2006 07:04 | 11/14/2006 07:04 | 60 | 0 | Yes | SMBG |
| Rise | Follow-on | Tuesday | 11/14/2006 07:16 | 11/14/2006 08:17 | 64 | 60 | Yes | CGM |
| Rise | Follow-on | Tuesday | 11/14/2006 12:57 | 11/14/2006 13:57 | 65 | 60 | No | CGM |

FIG. 24

| Stage | Treatments | Control Grid Zone (INPUT) | Recommendation Text (OUTPUTS) | Guide Link (OUTPUTS) | Q Link (OUTPUTS) |
|---|---|---|---|---|---|
| Metformin | Metformin | Hypo Risk Zone | NA | NA | (TBD) |
| | | Buffer Zone | Decrease variability<br>Go to next treatment stage | MNT<br>2Drug Start | (TBD) |
| | | "Safe to Titrate" Zone | Increase Met dose<br>At max Met dose | Met Adj<br>2Drug Start | (TBD) |
| | | Target Zone | You're on target! | | |
| Two-Drug Therapy | Metformin + SU | Hypo Risk Zone | Decrease SU dose<br>Decrease Variability | SU Adj<br>MNT | (TBD) |
| | | Buffer Zone | Decrease Variability<br>Out of target for 3 mos? | MNT<br>3Drug Start | (TBD) |
| | | "Safe to Titrate" Zone | Increase SU dose<br>At max SU dose | SU Adj<br>3Drug Start | (TBD) |
| | | Target Zone | You're on target! | | |
| | Metformin + DPP-4 | Hypo Risk Zone | Decrease DPP-4 dose<br>Decrease Variability | DPP-4 Adj<br>MNT | (TBD) |
| | | Buffer Zone | Decrease Variability<br>Out of target for 3 mos? | MNT<br>3Drug Start | (TBD) |
| | | "Safe to Titrate" Zone | Increase DPP-4 dose<br>At max DPP-4 dose | DPP-4 Adj<br>3Drug Start | (TBD) |
| | | Target Zone | You're on target! | | |
| | etc... | | | | |
| Three-Drug Therapy | Met + SU + Basal Ins | Hypo Risk Zone | Decrease Basal dose<br>Decrease Variability | Basal Adj<br>MNT(*) | (TBD) |
| | | Buffer Zone | Decrease Variability<br>Out of target for 3 mos? | MNT(*)<br>T2 MDI Start | (TBD) |
| | | "Safe to Titrate" Zone | Increase Basal dose | SU Adj | (TBD) |
| | | Target Zone | You're on target! | | |
| | etc... | | | | |

FIG. 36

METHOD OF HYPOGLYCEMIA RISK DETERMINATION

CROSS-REFERENCE TO RELATED APPLICATIONS

This application is a continuation of U.S. application Ser. No. 13/984,806, filed Nov. 21, 2013, which is a national phase application of PCT Application No. PCT/US11/66610, filed Dec. 21, 2011, which claims the benefit of U.S. Provisional Application No. 61/486,117, filed May 13, 2011, and U.S. Provisional Application No. 61/442,085, filed Feb. 11, 2011. Provisional Application Nos. 61/486,117 and 61/442,085 are incorporated by reference herein in their entireties and for all purposes.

This application is related to U.S. Provisional Patent Application No. 61/442,063 filed on Feb. 11, 2011; U.S. Provisional Application No. 61/442,092 filed on Feb. 11, 2011; U.S. Provisional Application No. 61/485,840 filed on May 13, 2011; U.S. Provisional Application No. 61/442,093 filed on Feb. 11, 2011, and U.S. Provisional Application No. 61/442,097 filed on Feb. 11, 2011, the disclosures of all Provisional Applications recited in this paragraph are incorporated by reference herein in their entireties and for all purposes.

BACKGROUND OF THE INVENTION

The Field of the Invention

The present invention relates to analyte measurement systems. More specifically, the present invention relates to a diabetes management system.

Background

One tool used in diabetes management is an analyte meter. An analyte meter is typically used to measure the blood glucose level of a user based on a sample of blood. The process of using an analyte meter is not complicated, and is often performed several times a day. First, the user inserts an analyte test strip into a test strip port of the meter. The user then lances her finger to obtain a small sample of blood. The blood sample is then placed onto the analyte test strip, and the meter analyzes the blood sample. The meter then typically displays a blood glucose level from the analysis.

Continuous Glucose Monitoring (CGM) systems are also used to manage diabetes and to collect data. A CGM system consists of a glucose-detecting sensor embedded in the interstitial layer beneath the epidermis, and an apparatus to receive and store glucose values. CGM systems have the advantage of collecting data on a regular basis, every 10 minutes for example, continuously for the lifetime of the sensor. This typically ranges from several days to one week. Much more data is collected, and there is 24-hour coverage.

The conventional method for providing analysis tools to help health care providers (HCPs) and patients absorb and understand glucose and other diabetes data has been to provide software that generates different graphs for HCPs and patients to review and consider. Unfortunately, the providing of graphs is lacking in that it is time consuming and requires a high level of expertise to be effective. What is needed is a system that processes data based on clinical standards and provides expert therapy decisions and support guidance.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the present invention.

FIG. 2 illustrates a glucose control level triage scale.

FIG. 15 provides an example of self-monitoring schedules according to the dimension of concern.

FIG. 19 illustrates an example of a Contingency Analysis for the occurrence of hypoglycemic episodes (dependent variable) changing with respect to the day of the week (independent variable) from continuous glucose monitoring.

FIG. 20 shows the rank-order of days of the week by being most different in terms of rate of hypoglycemia from what would be expected (that is, expected if there was no pattern across the days of the week).

FIG. 22 illustrates an example of a Contingency Analysis.

FIG. 23 is a table illustrating episodes detected for a patient for four calendar days.

FIG. 24 is a table illustrating episodes detected and allocated for a patient for four calendar days.

FIG. 36 illustrates an example of a treatment recommendation lookup table, according to certain embodiments.

BRIEF SUMMARY

Presented herein are one or more software applications to help a user manager their diabetes. Embodiments and descriptions of the various applications are provided below in conjunction with an analyte measurement device.

DETAILED DESCRIPTION OF THE INVENTION

Before the embodiments of the present invention are described, it is to be understood that this invention is not limited to particular embodiments described, and as such may, of course, vary. It is also to be understood that the terminology used herein is for the purpose of describing particular embodiments only, and is not intended to be limiting, since the scope of the embodiments of the invention will be limited only by the appended claims.

Figure 1:
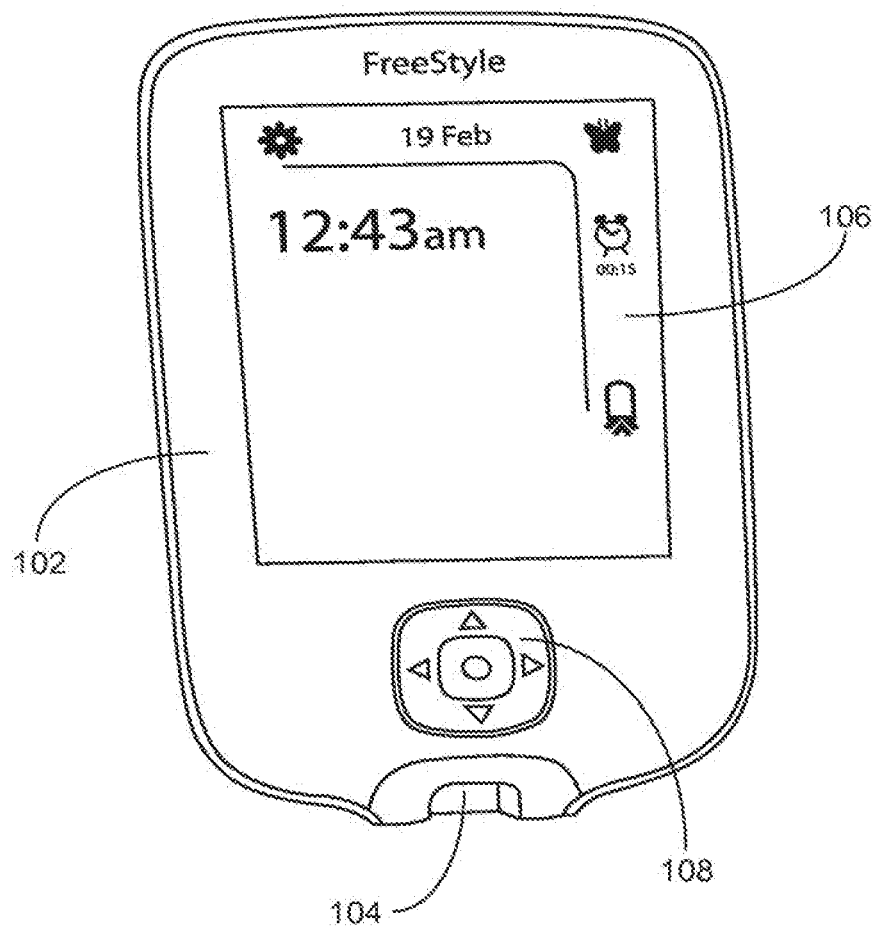
FIG. 1 provides a front-side view of handheld analyte measurement device in accordance with certain embodiments presented herein.

FIG. 1 provides a front-side view of handheld analyte measurement device, such as an analyte meter 102, in accordance with certain embodiments presented herein. In certain embodiments, analyte meter 102 includes a test strip port 104, a display unit 106, and at least one control button 108. In practice, an analyte test strip (or sensor) is inserted into test strip port 104 in order to conduct an analyte test; for example, a blood glucose reading or a blood ketone reading. Meter 102 includes software to analyze the sample placed on the test strip, and the results of the analysis are typically displayed to the user via display unit 106. The user may also use control button 108 to provide appropriate instructions to meter 102.

In certain embodiments, meter 102 includes one or more diabetes management software applications. The integration of software applications with meter 102 provides an opportunity to augment traditional glucose and/or ketone readings to provide more useful information and feedback to patients and HCPs. As such, meter 102, with loaded software applications, can be part of a robust therapy management system. The software applications can be factory pre-loaded, or installed by the user or health care provider after first use by the user. In addition to the software applications discussed below, meter 102 may include one or more of the software applications described in U.S. Pat. No. 7,766,829; and U.S. Provisional Patent Application Nos. 61/015,185; 61/262, 849; 61/290,841; 61/254,156; and 61/325,155; the disclosures of which are incorporated herein by reference in their entirety. As such, in certain embodiments, the analytics described herein may be located on the patient's personal device.

In certain embodiments, software applications are licensed, acquired, or otherwise built by third-parties to be incorporated into meter 102, or other biometric devices. Examples of the types of software that may be incorporated include: (a) behavioral engagement software; (b) therapy recommendation algorithms; (c) survey applications; (d) report-generating software; etc. A means may be provided to prevent unauthorized software from being executed by the device. A number of methods may be used to prevent such unauthorized execution. For example, the operating system on the device may require a code imbedded in the software before it would allow the software to be executed. The code may be provided by the meter manufacturer to trusted third-party vendors. Furthermore, the code may be generated from information provided regarding the application, to prevent the code from being publicized. In other words, a generation algorithm code may be provided. The information used to generate the code may be, for example, the company name or product name or another code. Also, time based information may be used, such as the earliest date that the application may be installed. Further, actual loading of the software on the device may be prevented, using the same techniques. For example, the installation driver located on the device may require authorization before it proceeds with installation.

Analyte meter 102 may further include one or more internal or external communication modules. The communication module(s) may be used to receive and/or transmit data and/or program instructions. The communication module(s) may also download software applications from one or more servers. In certain embodiments, the communication module is used to communicate with one or more external devices; such as, for example, a medication (drug) deliver device; a cellular phone; a laptop computer; a mobile device, such as a PDA, iPhone, iPad, tablet computer, etc.; a desktop computer; an analyte meter; and/or another analyte measurement system. In certain embodiments, the communication module can be configured for wired or wireless communication to an external device. Wireless communication may be provided by, for example, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In another embodiment, the patient's analyte meter 102 may include a communication module to connect to one or more servers (e.g., networked to a "cloud"). Data obtained from an analyte test can then be uploaded to the cloud, analyzed (automatically or semi-automatically) in the cloud, and results of the analysis can be downloaded to the patient's local device for review by the patient or an HCP. As such, the patient's local device can have limited processing capabilities because the bulk of the processing and analysis will be performed in the cloud. Further, such a system can allow a diabetes management company to control, manage, and/or update software in the cloud, without having to control, manage, and/or update software on the local devices of a large pool of patients. As such, in certain embodiments, the analytics described herein may be located on one or more centralized servers (i.e., "cloud").

Further, such system provides an opportunity to employ systems and methods for analyzing patient analyte data based on clinical standards, and provide expert therapy decision and support guidance, even if the patient or her local care provider lacks the expertise for sophisticated analyte analysis. For example, presented herein are systems and methods that can be widely utilized by non-diabetes expert primary caretakers. Achieving this goal will generally improve the health of people with diabetes and ultimately reduce health care payor costs.

In certain embodiments, the systems and methods presented herein are applicable under the preferred architecture of a web-based system (e.g., centralized server, cloud, centralized database, etc.) which includes connectivity to personal devices used by the patients. Patient devices include glucose meters, insulin pumps, cellular phones, PDA's, mobile devices, and/or personal computers. Intermediate connectivity devices may be included, such as a repeater which acquires the glucose data periodically from a glucose meter via wired or wireless communication (e.g., Bluetooth, WiFi, cellular, etc.) and transfers the data to a server (or intermediate server) via a standard pager communication network. In addition, a health care provider (HCP), or health care payor, may use a secondary device (e.g., a personal computer, web terminal, cellular phone, etc.) to access information from the server.

In another embodiment, the analytics described herein may be located on an HCP's device/system. In addition, the analytics described herein may be distributed across all the nodes of the diabetes management system.

Provided below are exemplary analytic systems and programs, in the form of software applications or otherwise, for use in the diabetes management system described herein.

Software Application for Triaging Glucose Control Assessment and Adapting Self-Monitoring Intervention For people with diabetes who are not taking multiple daily injections of insulin, the utility of self-monitored glucose measurements has not been well established. The current standard of care is to use the long-term biomarker of average glucose control A1C to assess and titrate diabetes therapies, with little or no regard to self-monitored glucose acquired using strips and sensors by patients in everyday settings. However, the failure of this approach is evident in that less than half of patients with diabetes in the U.S. meet control targets, putting them at higher risk for diabetes-related complications. The opportunity exists to create a software application which is capable of identifying underlying glucose control defects made apparent by self-monitored glucose that are not identifiable from long-term biomarkers such A1C.

Furthermore, for patients who do take insulin, identification of clinically-important patterns in their self-monitored glucose is extremely unstructured, and generally inefficient and time-consuming for care providers. The effect is such that the vast majority of care providers of insulin-using patients do not even bother creating computer-generated summary reports of downloaded self-monitored blood glucose (SHBG) values.

Further, A1C, as a long-term biomarker of excess glucose exposure, falls short of being able to monitor and assess important dimensions of glucose control. Such dimensions include overall hypoglycemia and glucose volatility, as well as periods of the day with excess hypoglycemia, glucose volatility, and glucose exposure. Therapeutic interventions to achieve target glucose control must recognize the trade-off between long-term risk of complications and acute risk of low glucose (hypoglycemia). If therapy is added improperly, there is the possibility of causing more harm (hypoglycemia) than good (reduction of long-term complication risk). To mitigate this situation, self-monitored glucose measurements may provide the necessary dimensions of control assessment, such that therapy can be adjusted in a progressively safe manner. Furthermore, since the physiologic defects in type-2 diabetes progress over time, there is a need to maintain monitoring of control even once targets have been met.

In certain embodiments, there is provided a software application that uses a clinically-rational scale of glucose control; i.e. a "triage" scale, and associated logic for selecting self-monitoring schedules (when and how often to measure) that are optimized to provide assessment of the main control defect identified on that scale. This logic is envisioned to be therapy-dependent in that the times of day posing control risk are expected to vary according to the type of diabetes therapy (e.g., single oral agent, combination therapy, background insulin only, background insulin with other agents, pre-mixed insulin, basal and bolus insulin, etc.) that is being utilized by the patient.

The first aspect of this application provides a rational priority to addressing out-of-target dimensions of glucose control provided by self-monitored glucose, as shown in FIG. 2, where the priorities are numbered (beginning with zero) in the order that they should be addressed. Within the categories it is proposed that problems identified during the night take priority over those during the day due to the increased risk of acute problems (low glucose) being unrecognized by the patient or others while sleeping. When self-monitored glucose data is analyzed (either on a meter or external to a meter), this scale helps focus clinicians on therapy adjustments which address the triaged levels of control in a safe manner. While the general categories are fixed, the criteria for satisfying each level may vary according to individual patient differences or class of patient (e.g., age, therapy used, duration of disease, diabetes type). In any case, the goal of the software application is to focus on the optimally addressing a single aspect of glucose control while keeping other dimensions of glucose control in proper and safe context.

Figure 3:
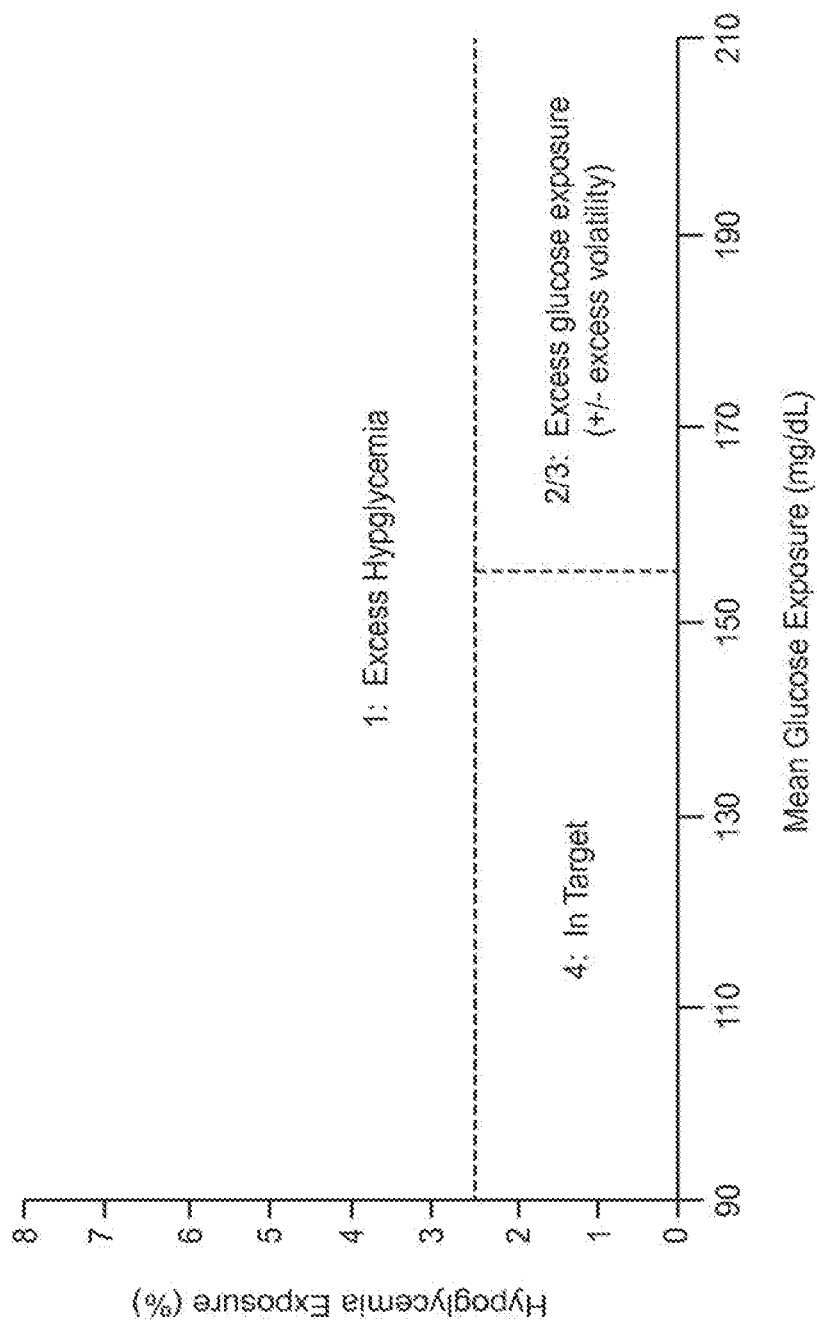
FIG. 3 shows a glucose control grid: Hypoglycemia vs. Mean Glucose Exposure.
Figure 4:
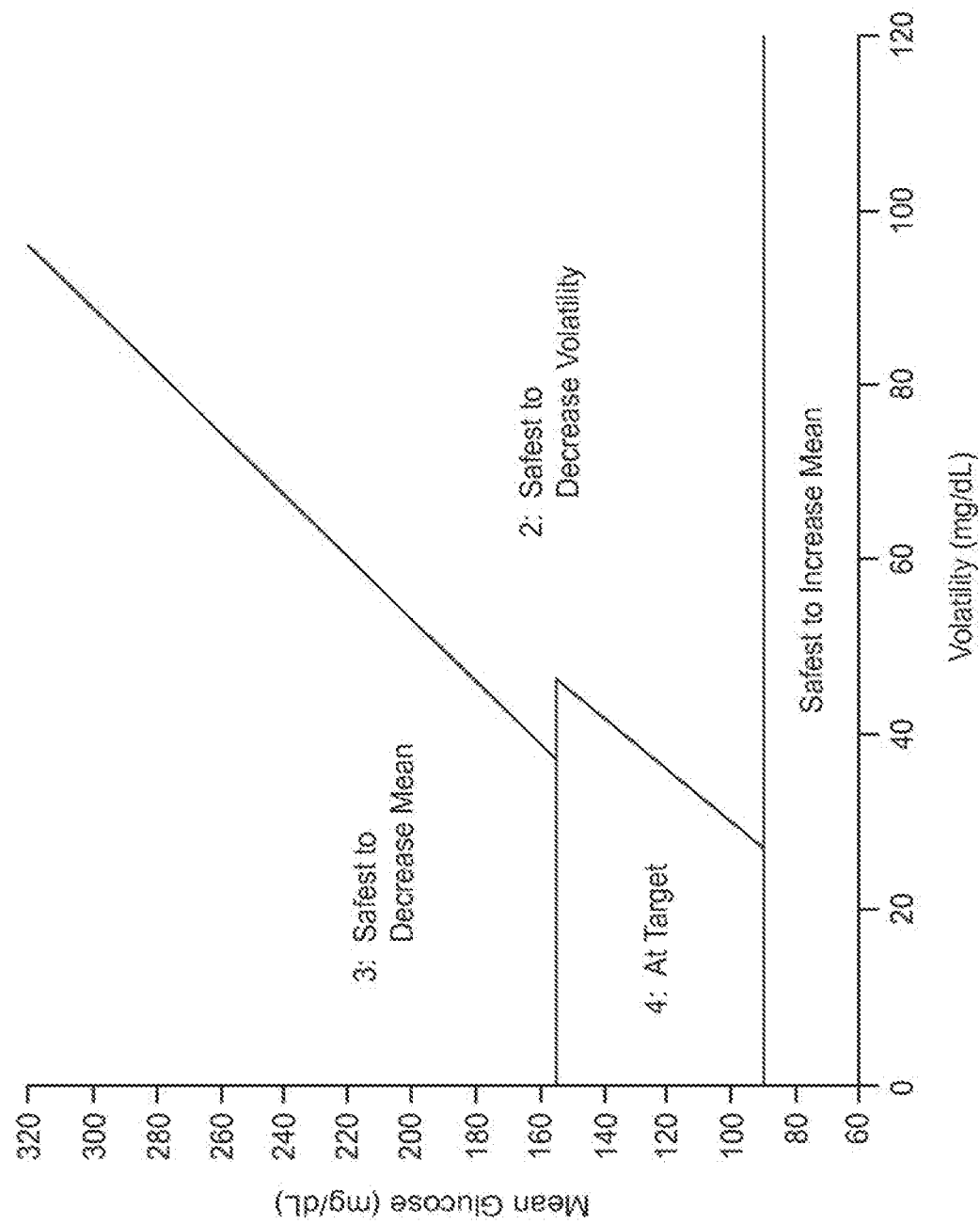
FIG. 4 shows a glucose control grid: Mean Glucose Exposure vs. Volatility.

Progress along this glucose control scale can be represented along the dimensions of interest. For example, FIG. 3 shows how the scale maps to a grid of hypoglycemia versus glucose exposure. This representation emphasizes that hypoglycemia needs to be addressed first, even if it results in an increase in glucose exposure to get control levels 2 or 3. In another example, FIG. 4 shows a grid of glucose exposure versus glucose volatility. This representation is more effective at contrasting control levels 2 and 3.

In another aspect of the present inventions, the software application proposes how to allocate discrete self-monitored glucose measurements according to glucose control level. This aspect is intended to guide how to allocate a relatively small number of glucose measurements per day (e.g., 1-12) over a number of days such that the dimension(s) of glucose control of interest is optimally measured. At minimum, the software application proposes that there are optimal "schedules" to discrete the self-monitoring of glucose for each glucose control levels (1-4). The schedules are likely to be further refined according to diabetes therapy type being used or other patient characteristics. Furthermore, algorithms may be developed which automatically shift between schedules as each dimension of control is assessed and surpasses thresholds. In some cases, prior knowledge of the initial condition of the patient, such as non-insulin-using type-2, may be used to modify the testing schedule to reduce testing for hypoglycemia.

Figure 5:
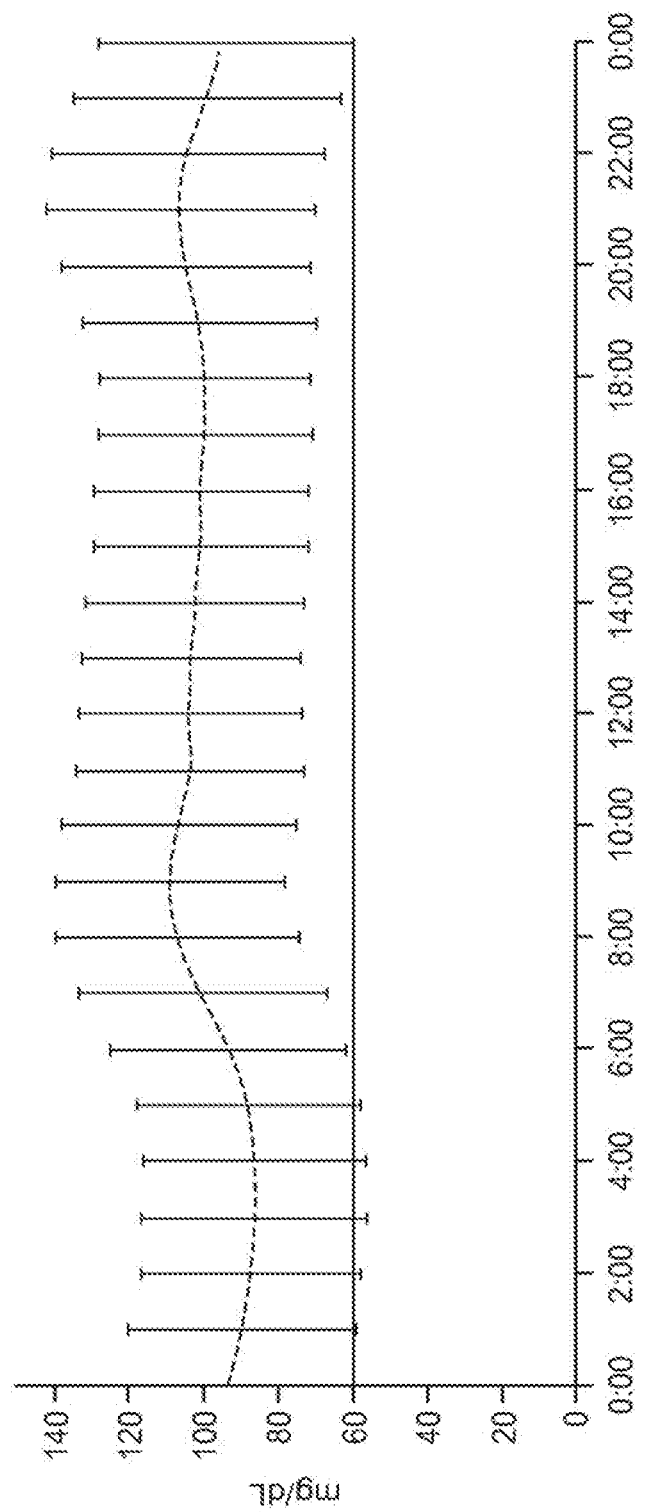
FIG. 5 provides a mean and standard deviation graph of hourly 10th percentile of glucose values for 80 patients on multiple daily injections of insulin.
Figure 6:
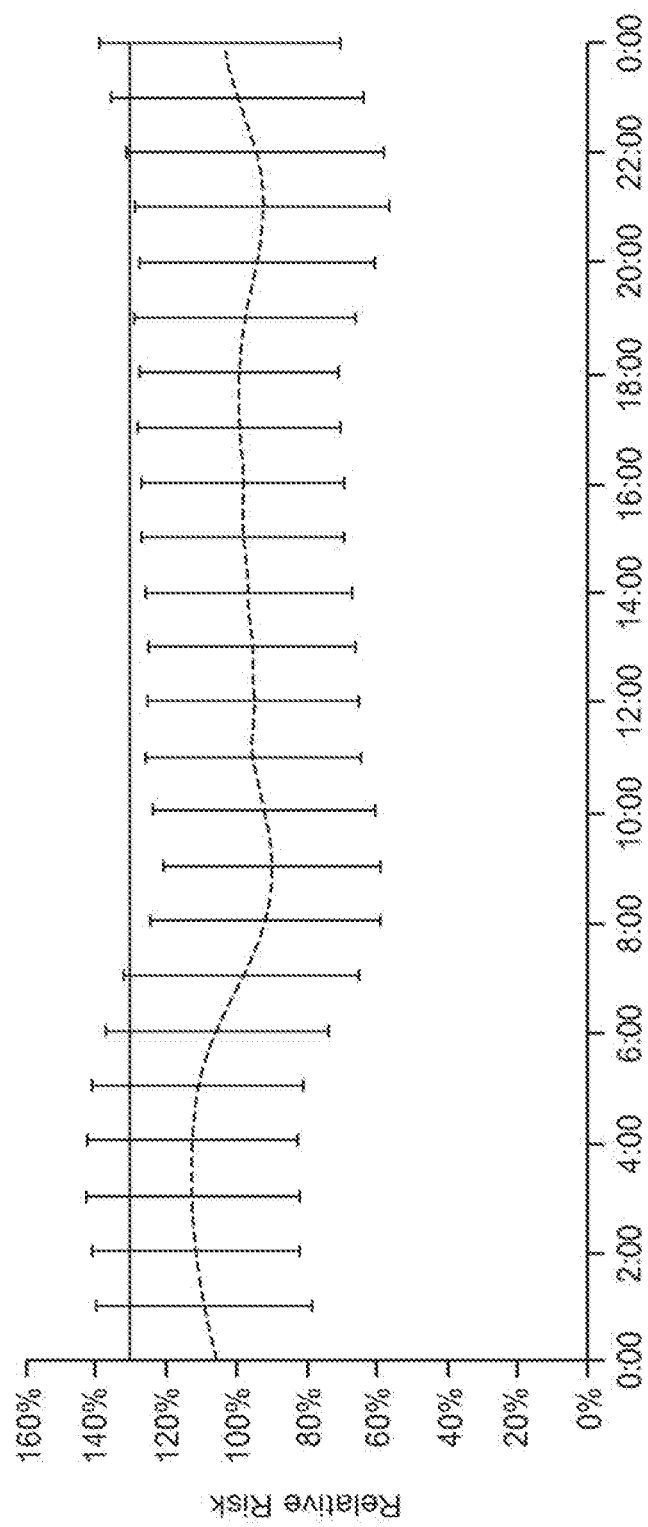
FIG. 6 provides hourly hypoglycemia risk: hourly mean and standard deviation of 10th percentile adjusted for 24-hour mean (80 patients on multiple daily injections of insulin), 100% set to mean hourly hypoglycemic risk.
Figure 7:
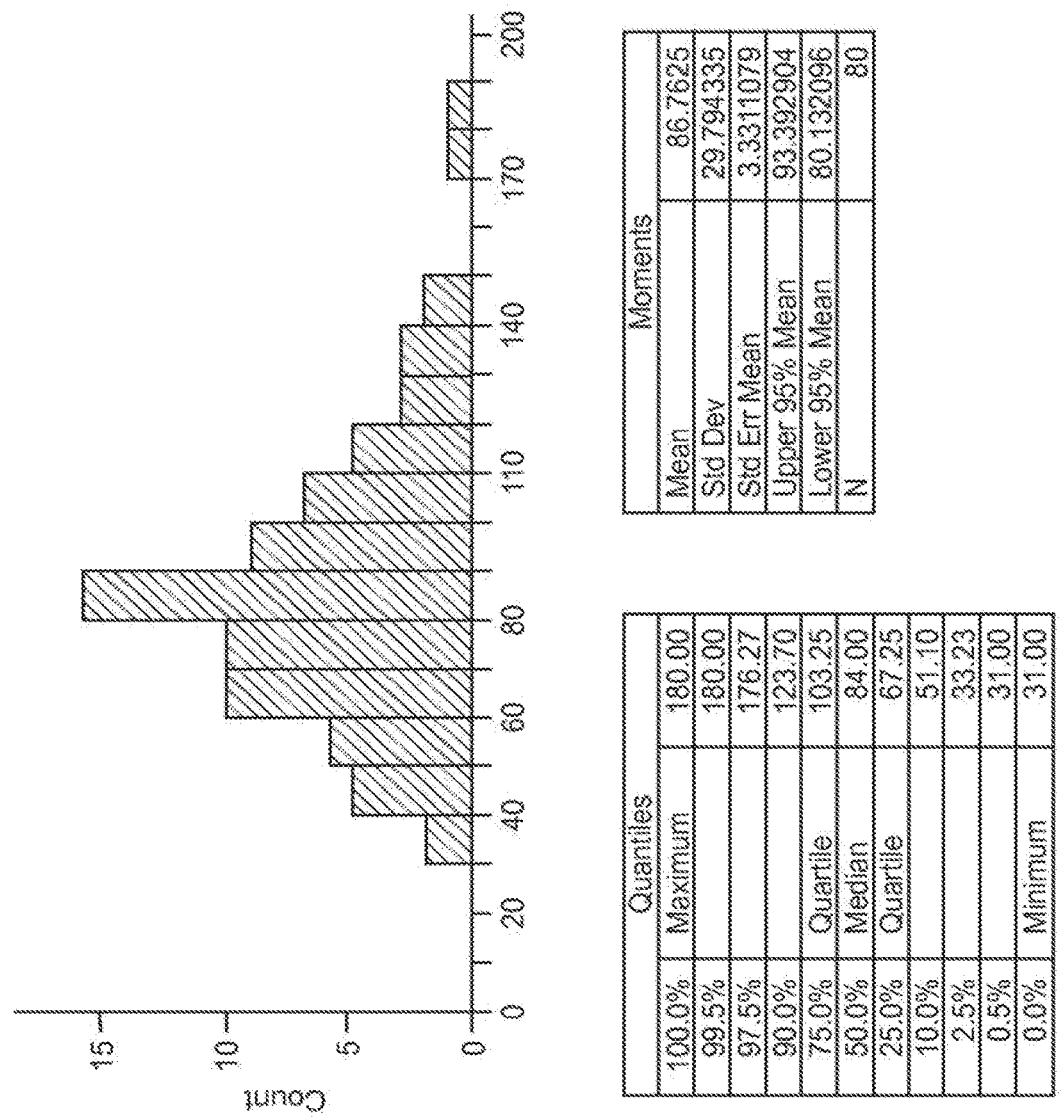
FIG. 7 provides 10th percentile of glucose values at 4 AM for 80 patients on multiple daily injections of insulin.
Figure 8:
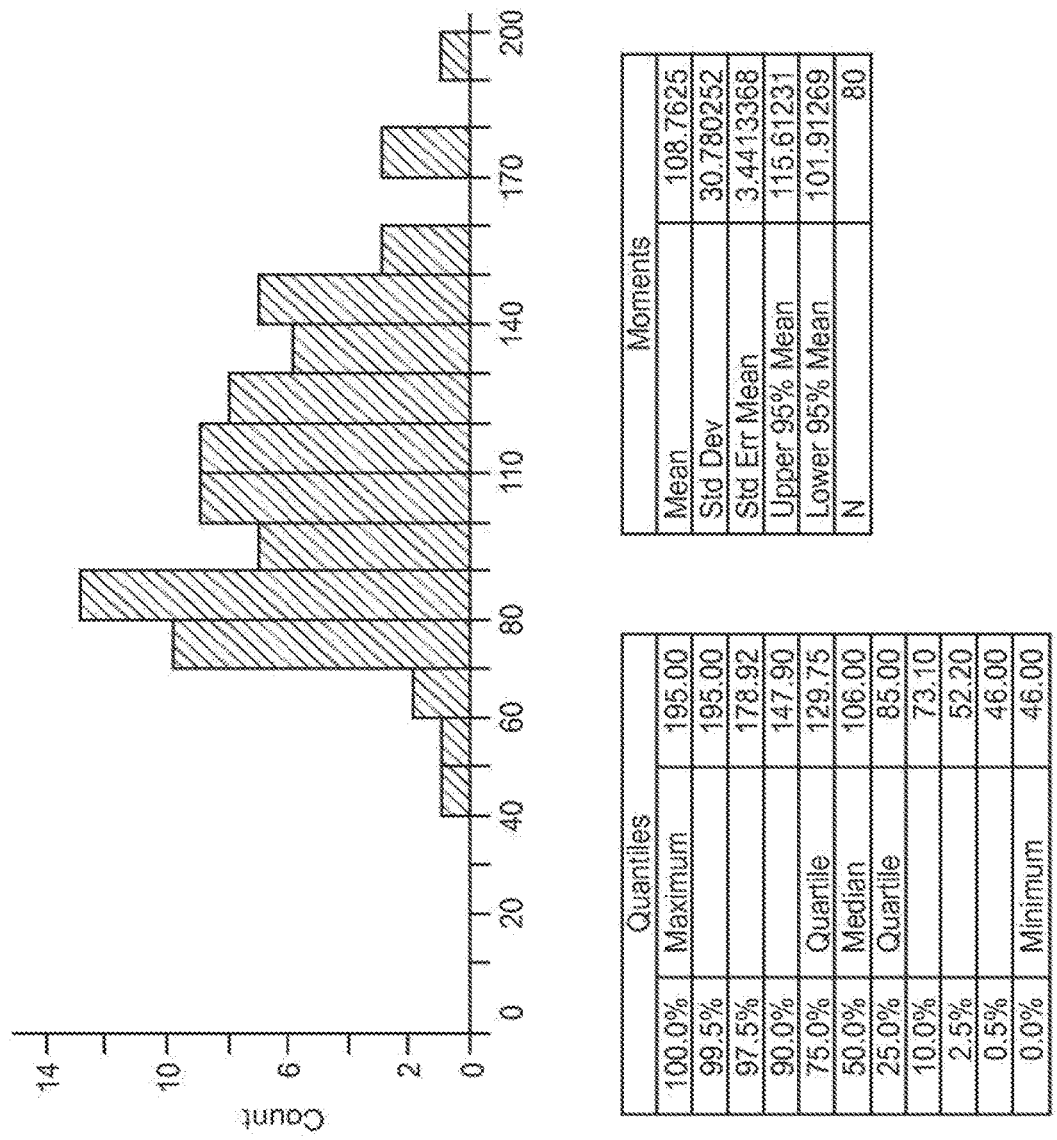
FIG. 8 provides 10th percentile of glucose values at 9 AM for 80 patients on multiple daily injections of insulin.

To demonstrate this aspect of the invention, it is applied to a group of patients on multiple daily injections of insulin (MDI). Each patient had continuous glucose monitoring every 10 minutes for 14 days. Within each hour of the day, the 10th percentile value was found. Typically this means there were 6 measurements per hour over 14 days for a total of 84 values within each hour. These values are sorted, highest to lowest, and one method to define the 10th percentile value is to do a linear interpolation between the 8th and 9th lowest values (since the 84/100=“$8.4^{th}$” value doesn't exist). In this way, a glucose value is found for each hour where 90% of the glucose measurements in this hour of the day are higher than that value, and 10% are lower. Combining all the patients, the mean and standard deviation of their hourly 10th percentile glucose values are shown in FIG. 5. These values are transformed into hourly hypoglycemia risk by scaling to the 24-hour mean of the 10th percentile values by: [1-(24-hr mean-x-hr)/24-hr mean] *100, where x is each hour of the day, shown in FIG. 6. This shows that for this class of patients the highest hypoglycemia risk is between 11 PM and 7 AM, shown by having the error bars exceed the selective threshold of 130%. Two hours of the day are compared in FIG. 7 and FIG. 8. At 4 AM, 25% of the patients have 10% of their glucose values below 67.25 mg/dL, representing more hypoglycemia during that hour of the day then at 9 AM (less than 10% of the patients have 10% of their glucose values below 67.25 mg/dL). This indicates that self-monitoring schedule to assess hypoglycemia risk should be more comprehensive during the night then during the day.

Figure 9:
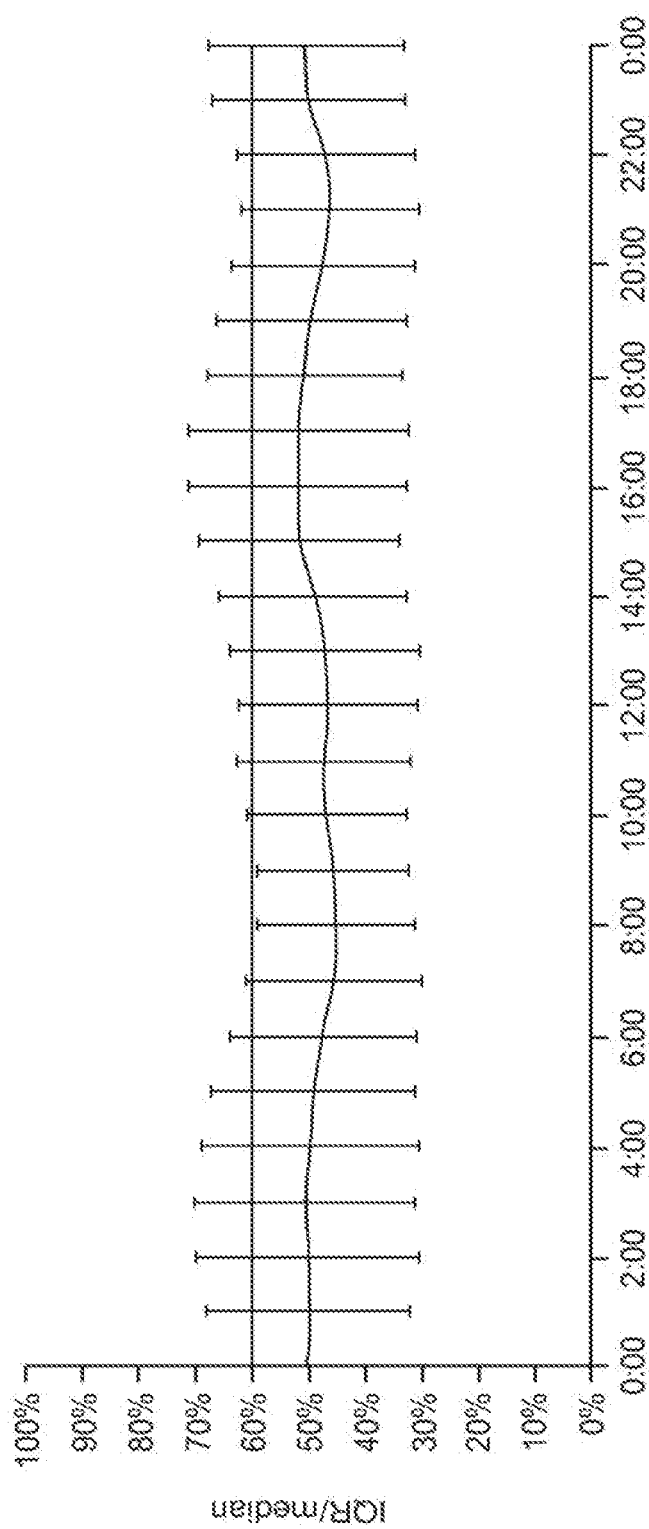
FIG. 9 provides hourly volatility risk: mean and standard deviation of hourly (interquartile range/median) of glucose values for 80 patients on multiple daily injections of insulin.
Figure 10:
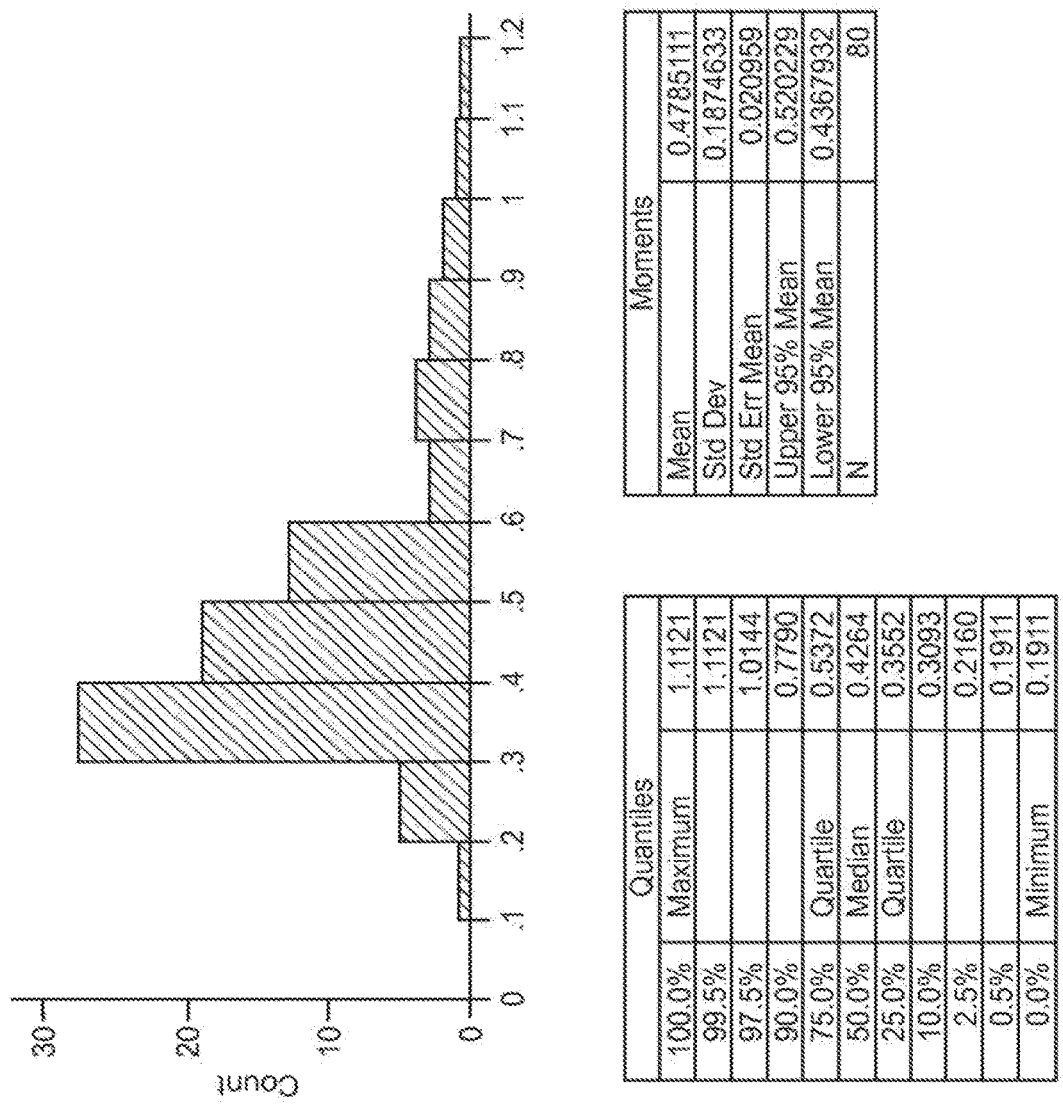
FIG. 10 provides relatively interquartile range (IQR/median) of glucose values at 9 AM for 80 patients on multiple daily injections of insulin.
Figure 11:
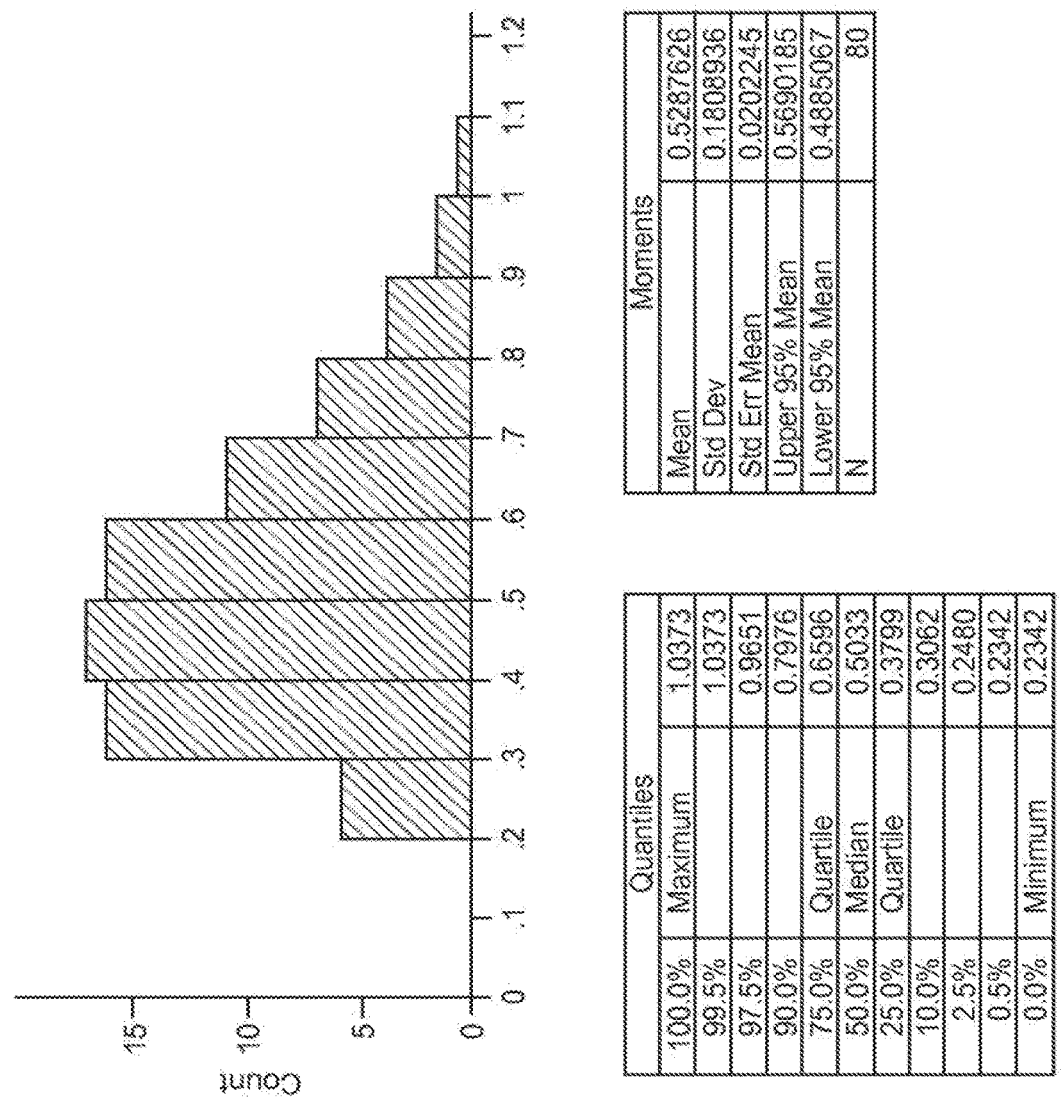
FIG. 11 provides relative interquartile range (IQR/median) of glucose values at 4 PM for 80 patients on multiple daily injections of insulin.

It is important to manage glucose volatility, since excess volatility may result in increased hypoglycemia when therapies are adjusted to reduce overall glycemia. FIG. 9 shows the volatility per hour of this group of MDI patients, indicating that a self-monitoring schedule to assess volatility should be more comprehensive during the hours of 10 PM-7 AM and 2 PM-8 PM. FIG. 10 and FIG. 11 compare the volatility of two different hours of the day, one with the main time of concern (4 PM) and one outside the time period of concern (9 AM).

Figure 12:
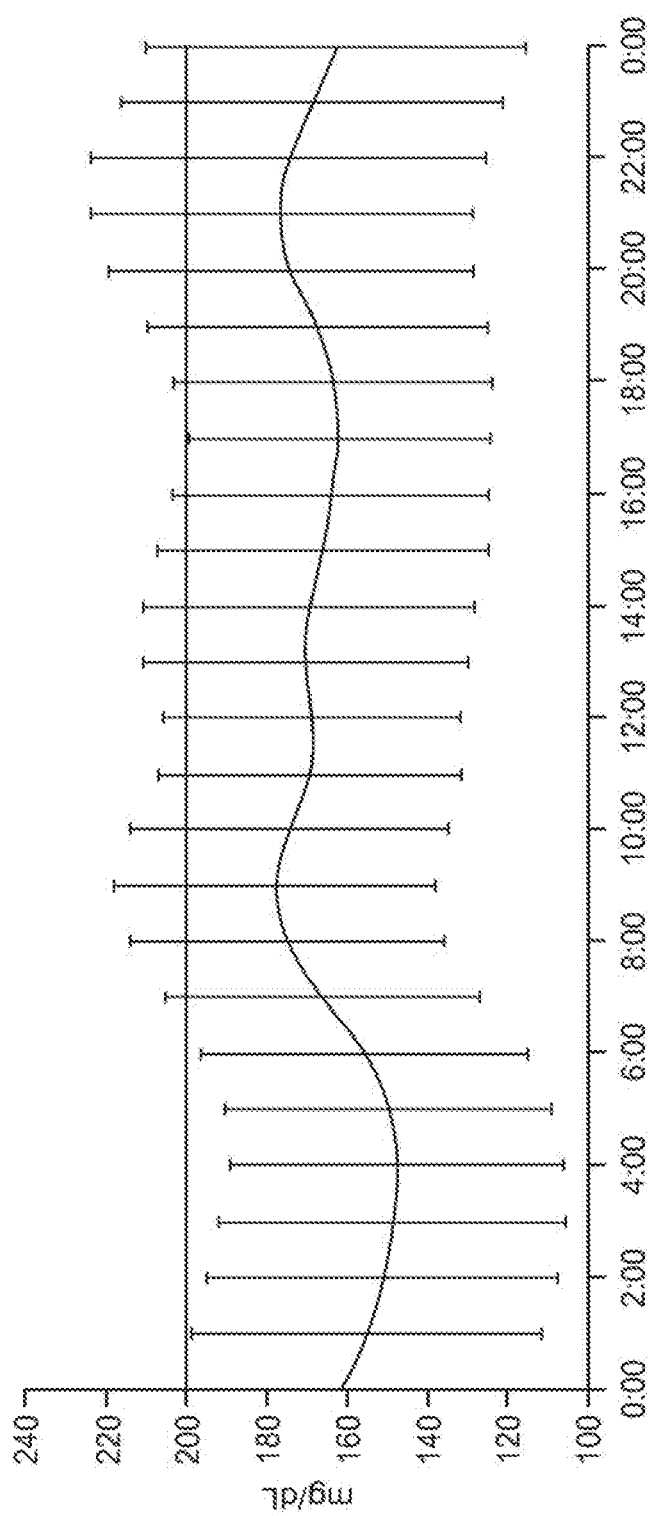
FIG. 12 provides hourly excess glucose risk exposure: mean and standard deviation of hourly median of glucose values for 80 patients on multiple daily injections of insulin.
Figure 13:
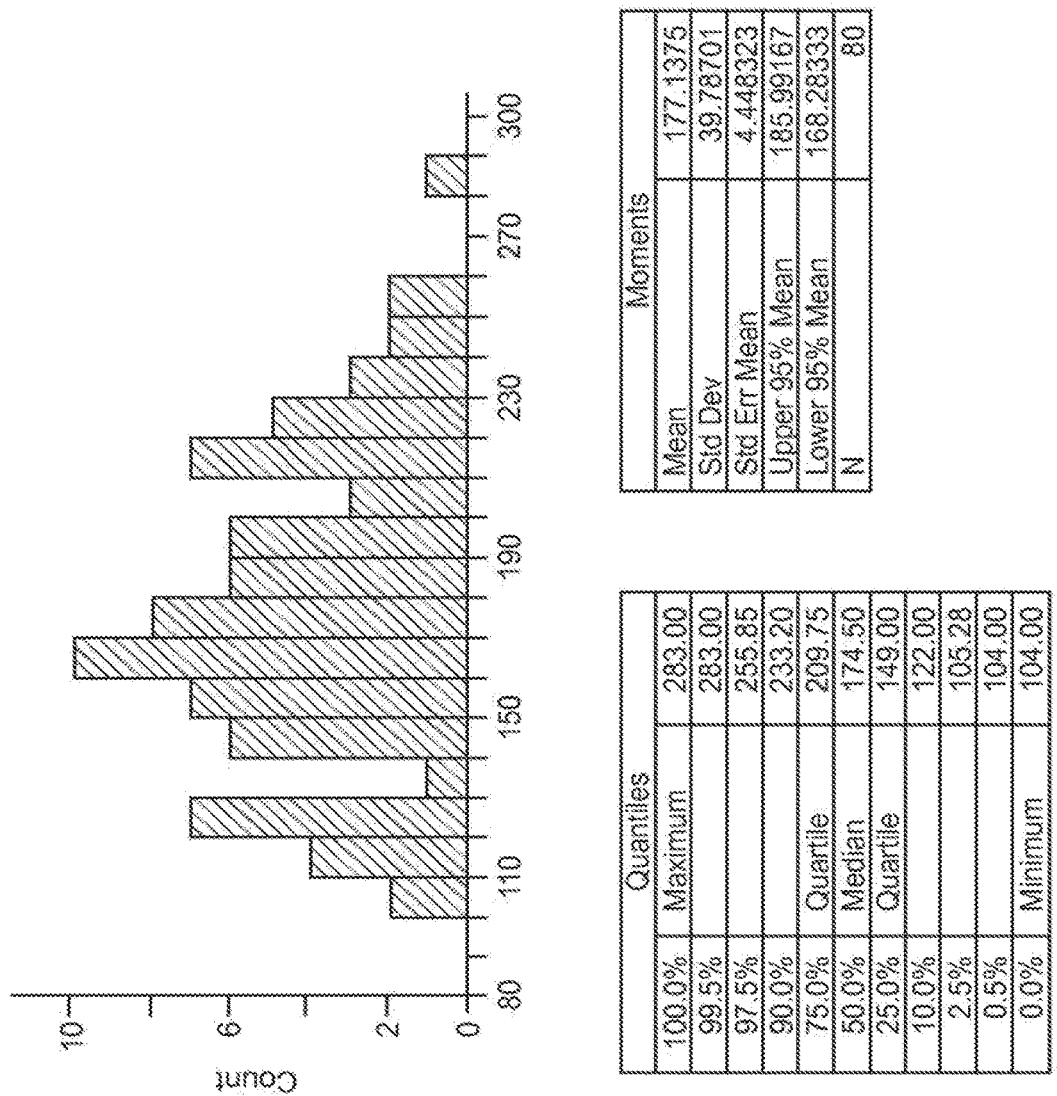
FIG. 13 provides median of glucose values at 9 AM for 80 patients on multiple daily injections of insulin.
Figure 14:
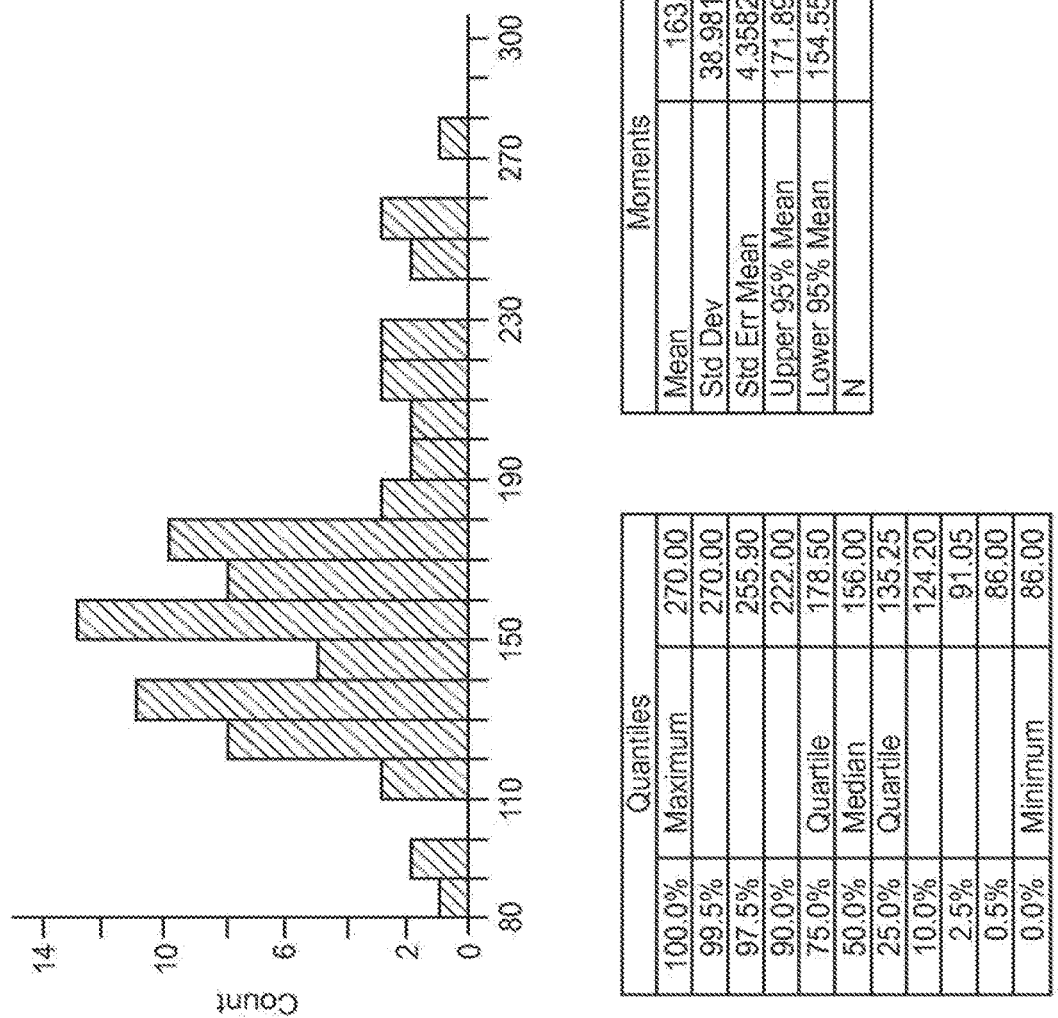
FIG. 14 provides median of glucose values at 4 PM for 80 patients of multiple daily injections of insulin.

In order to assess excess glucose exposure, FIG. 12 shows the exposure per hour for this group of MDI patients, indicating that a self-monitoring schedule to assess excess glucose exposure should be more comprehensive during the hours of 7 AM-3 PM and 7 PM-12 AM. FIG. 13 and FIG. 14 compare the excess glucose exposure of two different hours of the day, one with the main time of concern (9 AM) and one outside the time period of concern (4 PM).

In summary, an example of self-monitoring schedules according to the dimension of concern is shown in FIG. 15.

In another embodiment, the software application associates specific therapies with optimal SMBG test schedules, which can be downloaded to a glucose meter. The software application also analyzes diabetes data based on median glucose and glucose variability to prioritize the displayed findings. As such, the recommended treatment will ultimately reduce median glucose without causing hypoglycemia.

Software Application for Workflow Automation

Therapy modifications for diabetes patients have been traditionally made based on PC software that provides HCP's with reports that illustrate glucose management. Utilization of these reports is time consuming and requires a high degree of expertise by the HCP. In certain embodiments provided herein, there is provided a method and system to automate analysis of diabetes data, which generates treatment recommendations and relevant reports that illustrate problems. In another embodiment, there is provided a method and system for workflow automation. Specifically, there is provided an optimal workflow order presented where automatic treatment recommendations are presented and utilized as part of the HCP's visit workflow.

In certain embodiments, there is provided a workflow that has two phases—one targeted for clinical assistant activities (e.g., "waiting room" workflow), and a second for the HCP (e.g., "exam room" workflow). The first phase involves uploading the device data and entering data into a PC application based on a preliminary interview with the patient. This activity can be done by the clinical assistant. The second phase is where the application provides a summary of the analysis to the HCP and provides a means for the HCP to determine and record treatment modifications, all provided in an interactive display. The HCP can review these results, which would provide detailed findings, reports associated with these detailed findings, questions to the patient associated with the findings, and treatment recommendations from which to select. Answers to questions, selected treatment recommendations, and selected reports to illustrate findings and treatment decisions, or to educate the patient, would be recorded.

Figure 16:
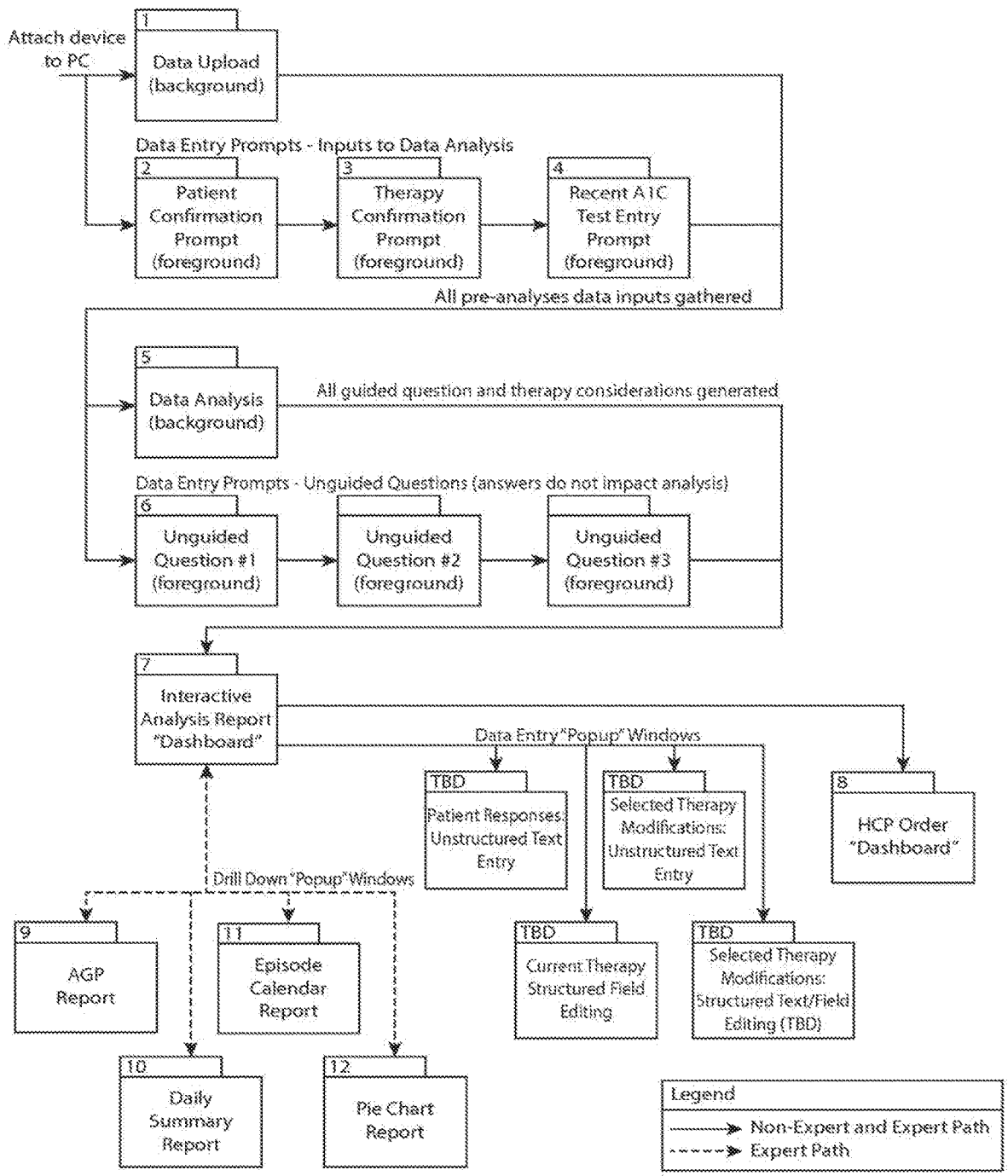
FIG. 16 is a flowchart in accordance with certain embodiments of the present invention.

FIG. 16 is a flowchart in accordance with certain embodiments of the present invention. In FIG. 16, the boxes noted 1-6 generally correlate with the above-described "Phase 1." Boxes noted 7-12 (and TBD) generally correlate with the above-described "Phase 2."

In certain embodiments, there is provided a workflow method as follows:

1) Phase 1
   i. Inputs to the automated logic are retrieved
      1. Glucose data and any other pertinent logged data are uploaded from the glucose measurement device.
      2. Patient identification and specific information is retrieved based on the uploaded device serial number and a prompt is presented to allow confirmation or correction.
      3. Current patient treatment is retrieved based on the uploaded device serial number, and a prompt is presented to allow confirmation or correction to this treatment.
      4. A prompt is presented for entry of any recent test information, such as A1C or blood pressure.
      5. A prompt is presented for entry of any other information that is required as an input to the analysis logic.
      6. A prompt (optional) is presented for patients to describe any conditions or problems they wish to discuss during the exam with the HCP. This may or may not impact the analysis logic. An example situation, which would impact the analysis, would be if the patient selects a specific time period(s) that was difficult to manage and wishes to discuss/review with the HCP. Such prompts are provided for the patient to enter additional information that is not typically used as an input to the analysis logic (e.g., "unguided" or open-ended questions that can be answered by the patient).
   ii. Analysis logic process is performed using the above inputs 2) Phase 2
   i. An interactive display (e.g., Box 7 in FIG. 16) is presented that includes:
      a. results of the analysis ("Findings" and "Actions to Consider"), structured by the important periods of the day for diabetes management: "Fasting" and "Post-Meal", and (optionally) a standardized report;
      b. findings may be color-coded, or otherwise annotated, to indicate negative and positive findings;
      c. means to expand and collapse Findings, where Findings can be expanded to detail findings and actions to consider, questions to ask the patient, and treatment recommendations (e.g., results from the analysis);
      d. means to navigate to a report pertinent to a particular finding;
      e. means to navigate to HCP-oriented reference materials pertinent to a particular finding and/or action to consider;
      f. means to navigate to patient-oriented diabetes self-care education materials pertinent to a particular finding and/or action to consider
      g. means to select or deselect the patient-oriented diabetes self-care education materials pertinent to a particular finding and/or action to consider for printing or electronic delivery to the patient
      h. means to add HCP-selected detailed reports to a summary report for long-term storage (e.g., "journal" specific reports of value for medical charting or patient education);
      i. means to navigate to entry screen pertinent to a particular question or treatment recommendation;
      j. a displays of entry screen inputs for questions answered;
      k. a displays of entry screen inputs for selected treatment recommendations; and/or
      l. a displays entry screen for ad hoc questions answered and treatment recommendations.
   ii. A treatment order is prepared based on the selected treatment recommendations and the results of the analysis and HCP input (e.g., Box 8 in FIG. 16).

The selected treatment recommendations may be text fields and may include modification of treatment fields. The interactive display may present this information in a dashboard format, a tab format, an icon based format or some other means. Other interactive fields may be added to this interactive display, such as means to compare treatments and treatment results from prior clinical visits.

The described workflow may be extended to include two or more analysis stages. For instance, the first analysis stage may be as described above, but may generate additional questions to be asked of the patient that may form inputs to a second analysis stage (along with inputs to the first analysis stage and outputs from the first analysis stage).

Software Application for Identifying Episodes

Figure 17:
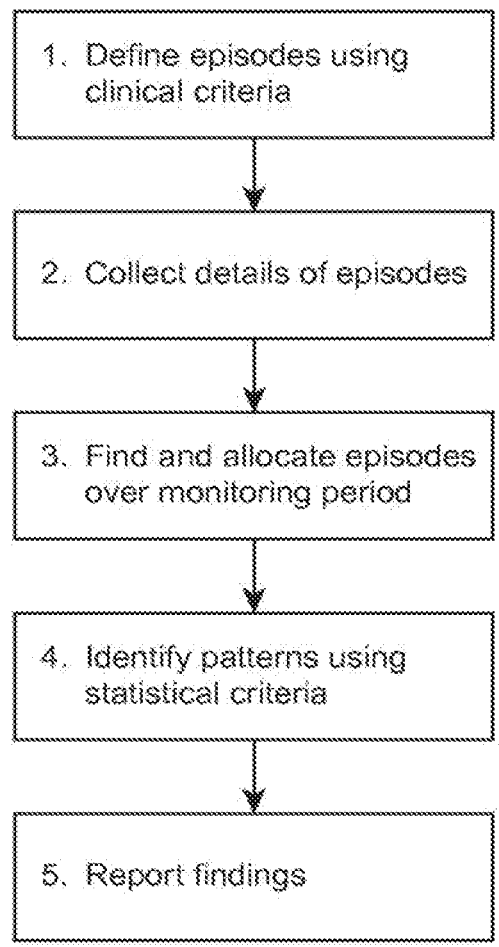
FIG. 17 is a flowchart in accordance with certain embodiments of the present invention.

In certain embodiments, there is provided a process for identifying features of glucose measurements (i.e., "episodes"), collecting supporting details about these episodes, using statistical methods to assess if any particular conditions or actions appear to influence the likelihood of these episodes occurring, and describing this analysis in a clinically-meaningful way to better inform health-care providers about the status of their patients and potential next steps in their treatment and disease management. FIG. 17 provides a flowchart in accordance with said process.

HCPs who use current systems of glucose data management and assessment still request further assistance from these systems to help answer basic questions of clinical relevance. For example, HCPs want to know if a patient is experiencing hypoglycemia more often on some days of the week compared to others. Provided herein is a method to address questions of this nature, with both statistical and clinical input, to arrive at answers and suggested clinical actions.

In certain embodiments, there is provided a method to define episodes using clinical criteria. The clinical criteria may be universally applied for many patients of similar disease state and therapy, or customized for individual patients. Episodes are generally a categorized period with the possible mutually exclusive values of "Yes," "No", or "unknown." The "unknown" category would apply if a period of time has no data to relate whether an episode may or may not have occurred.

Episodes are further generally categorized by clinically-relevant criteria. Examples may include episodes of hypoglycemia, hyperglycemia, rapid glucose increases, rapid glucose drops, etc. Examples here will focus on episodes determined from glucose monitoring, but may be extended to any other frequently monitored behavior, activity, or biological parameter.

In certain embodiments, there is provided a method to collect details of episodes. Details of episodes are collected for further analysis, such as: 1) when the episode started and ended; 2) the day of the week the episode occurred; 3) the week of the month the episode occurred; 4) how long before or after the episode an activity was performed; 5) the glucose levels or statistical summaries of the glucose levels before, during and after the episode; 6) the source of the glucose measurements (say "continuous glucose monitoring" or "self-monitored blood glucose").

The method further includes finding and allocating episodes over a monitoring period. Allocation may be assigned according to a number of possible clinically relevant reasons, such as: week of a month, day of the week, time period in a day, behavior or activities (taking medication, eating, sleeping, exercising, etc), glucose value, glucose rate of change, state of health of the patient, etc.

As one example, the allocation may be done over each hour of the monitoring period being evaluated. For example, if three months have elapsed since monitoring has been initiated by the patient, there may be approximately 90*24=2160 hours of monitoring where an episode can be allocated as "Yes," "No," or "No monitoring available (unknown)."

As another example, the allocation may be done according to the measured glucose value, and whether an episode occurs within some future time period. Alternatively, when an episode does occur, descriptive details of that episode can be allocated (such as the maximum glucose rate of change within 1 hour before the episode) and statistically and clinically relevant patterns can be investigated.

The method further includes identifying patterns using statistical criteria. Once allocated over the monitoring period of interest, statistical methods can be used to determine how likely occurrences of episodes (the "dependent variable") relative to any possible independent variable (i.e. "clinically relevant reason") is to be observed simply by mere coincidence. If the likelihood of coincidental observation, i.e. "by mere chance or luck," is low (say less than 1 in 20), then independent variables may be identified as having a strong association with the occurrence of episodes, and be deemed worthy of further investigation or discussion between the patient and healthcare provider, and interpretation by the healthcare provider to suggest therapy or behavior modifications.

Figure 18:
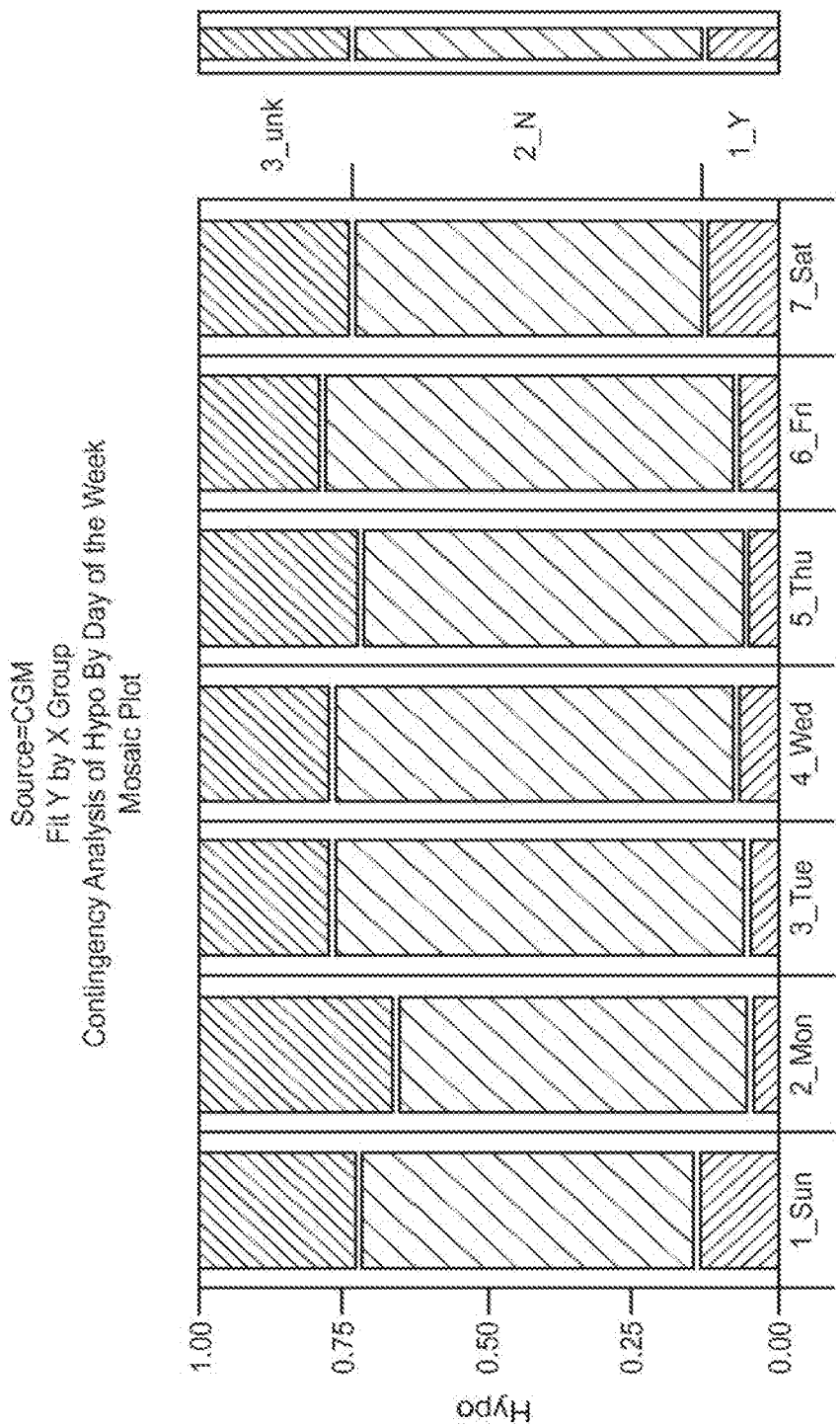
FIG. 18 illustrates an example of a Contingency Analysis for the occurrence of hypoglycemic episodes (dependent variable) changing with respect to the day of the week (independent variable) from continuous glucose monitoring.

A statistical method for this technique is the "Contingency Analysis." Shown FIGS. 18 and 19 are examples of a Contingency Analysis for the occurrence of hypoglycemic episodes (dependent variable) changing with respect to the day of the week (independent variable) from continuous glucose monitoring.

For the shown example, the statistical methods indicate a very low likelihood that the increased frequency of hypoglycemia on Sunday and Saturday is mere chance coincidence. In fact, the statistics indicate the likelihood of coincidentally seeing this pattern of hypoglycemia across the days of the week is smaller than 1 in 10,000. Therefore it's reasonable to assume that something about this patient's behavior or therapy on Saturday and Sunday is different from the rest of the week in regards to having hypoglycemic episodes. Therefore, a possible output of the system may be to summarize these findings: "Statistical analysis indicates the likelihood of coincidentally seeing this pattern of hypoglycemia across the days of the week is smaller than 1 in 10,000.

The rank-order of days of the week by being most different in terms of rate of hypoglycemia from what would be expected (that is, expected if there was no pattern across the days of the week), are shown in FIG. 20. Therefore, a possible output of the system may be to summarize these findings: "Consider evaluating therapy and/or behavior differences for those days that are at the extremes of being different from expected compared to those that are similar to expected." Or, "Consider ways to address the extremes and reduce hypoglycemic episode occurrence overall."

Figure 21:
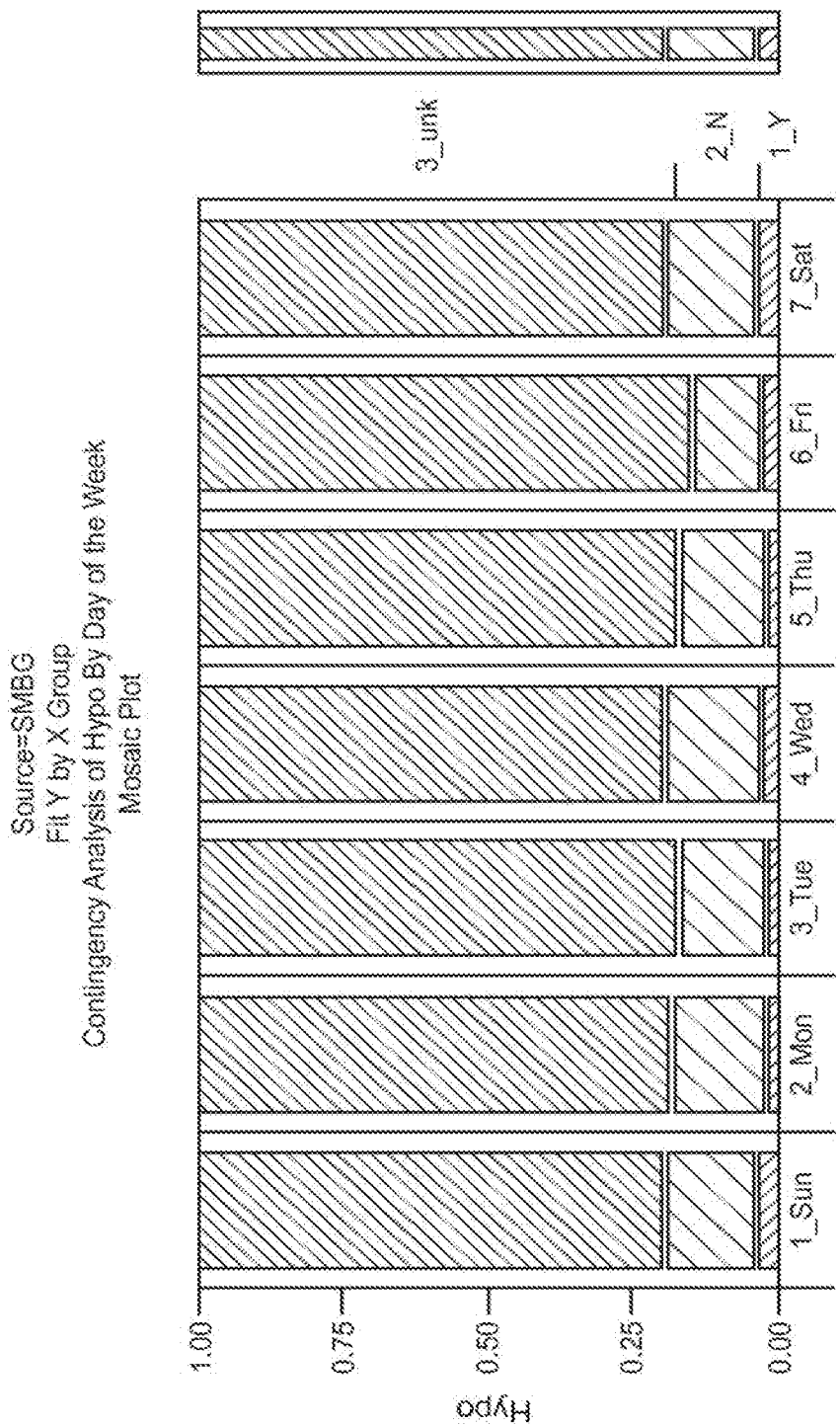
FIG. 21 illustrates an example of a Contingency Analysis.

Similar logic can be used for patterns related to hours of the day and patterns derived from SMBG. However, it is likely that with infrequent SMBG, the most likely outcome is to have too few monitoring periods to reach statistical significance, as shown in FIGS. 21 and 22. Therefore, a possible output of the system may be to summarize these findings: "The statistical analysis indicates the likelihood of coincidentally seeing this pattern of hypoglycemia across the days of the week is bigger than 1 in 4. Therefore no patterns of hypoglycemia across days of the week should be concluded, as they are too likely coincidental or 'mere chance' observations."

In addition, one output of the system may be to indicate that there are not enough measurements to execute the statistical analysis accurately. By convention, the rules are that the minimum expected number in any cell is 1 and that no more than 20% of the cells have an expected value of less than 5.

This invention would be incorporated into glucose data management software, either on a device or external to the glucose monitoring device. It would primarily be targeted to health care providers who guide therapy decisions to manage glucose levels. It would aid in investigating and relating clinically significant glucose measurements of interest with particular behaviors or therapy choices that their patient is performing. From there, the clinician may use his or her judgment to suggest effective actions for the patient to take in order to mitigate the observations and improve their disease control.

In certain embodiments, there is provided a process for creating summaries of patient-specific diabetes management information. Such information includes glucose (blood and interstitial), other analytes (e.g., blood lipids, albuminuria), markers of kidney (SrCr, eGFR) and liver (ALT, ULN) function, and daily activity information (meals, medication, exercise, disease symptoms). In certain embodiments, this information is used in an analytical tool that includes expert logic to drive automatic treatment recommendations. The information is used in a manner designed to make clinical review and therapeutic change decisions more rapid, consistent, and accurate.

Software Application for Providing Automatic Treatment Recommendations

Using glucose measurements to assess and determine changes to diabetes management and therapy intervention is a complicated process. HCPs in the field have repeatedly requested methods for "guidance" and "recommendations" for decisions that may help their patients better manage their disease. Historically, state-of-the-art methods for analyzing and summarizing glucose measurements have lacked clear links with therapy changes, and therefor automatically producing recommendations based on a priori logic has not be achieved in any broad sense.

Provided herein is a process for automatic and/or clinician-guided interpretation of extreme glycemic episodes for an individual with diabetes in order to improve selection of therapies and self-management intervention(s).

For example, in certain embodiments, there is provided a method for providing automated treatment recommendations by: (1) allocating episodes; (2) displaying patterns; and (3) allocating episode chains. A more specific description is provided below.

1. Allocating episodes in "initiators" and "follow-on" episodes, and linking episodes into "chains," that start with a single "initiator" and may or may not continue with one or more "follow-on" episodes. An initiator episode with no follow-on episodes is considered here to be a "single-link episode chain." An initiator episode with two follow-on episodes is considered a "3-link episode chain," and so on. All of these are considered "episode chains." This allocation of "chains" allows focusing on self-management problems that do or do not start a series of negative effects. Review of glucose measurements may reveal an episode was treated inappropriately, and thus initiated one or more additional episodes that the individual had to handle. A specific example would be a high glucose episode that is treated too aggressively, such that a rapid fall episode and a low glucose episode occur. This low glucose episode may also be treated inappropriately, and therefore a rise episode occurs, followed by another high glucose episode. This example shows the "roller-coaster" effect that can be the hallmark of difficult-to-manage diabetes. From a clinical perspective, however, the best place to intervene in self-management behavior is likely with the "initiating" episode. If the high glucose is treated differently, or is avoided altogether, then the train of episodes following may be reduced or removed effectively.

2. Displaying patterns of episodes relative both to time-of-day and time of initiation of a chain of episodes. Rather than a conventional 24-hour "modal day" plot, this invention plots additional "follow-on" episodes beyond the 24-hour time-axis if the chain extends past midnight of the day the chain initiated.

3. Allocating "episode chains" (defined here to minimally include a single "initiator" episode, and may have one or more "follow-on" episodes) into clinically relevant categories. This allocation is done according to the attributes of the chain, and may be done automatically to help frame the type of therapy interventions the clinician should likely consider for the individual under his or her care. Possible attributes of the chain are detailed more specifically below, but may be considered to include things such as: a) start time (or "time-of-day") of the chain; b) glucose value at the start of the chain; c) presence or absence of a continuous glucose monitoring threshold or projected glucose alarm; d) order of the types of episodes in the chain, e.g., a "High-High" chain would be allocated differently than an "High-Low" chain; and e) user actions (or inactions) before or during the chain. An "action" may be eating, taking medication, exercising, or other actions that may affect their diabetes management and glucose control.

An example patient may have glucose measurements that are summarized into a list of Low, High, Rise and Fall episodes, as shown in FIG. 23. These episodes are then allocated to "initiators" and "follow-on" episodes. Methods for determining initiator versus follow-on episodes may be based optimal selection of one or more of the following criteria: 1) time elapsed since previous episode, for example, if sufficient time has passed after an episode, the next episode may automatically be considered an "initiator," which would be based on the idea that therapeutic or other actions that affect glucose only have a finite period of influence on the glucose; 2) time of day of the episode; 3) the order or type of episodes, for example, all Rise episodes followed by a High episode may be considered "initiators;" and 4) type of actions the individual has recently performed, for example, rapid-acting insulin typically has about 3 to 6 hours of action, while long-acting insulin may be 12 to 24 hours of action. Some evidence suggests exercise may have 1 to 24 hours of action. Eating may have 1 to 8 hours of action, depending on the composition of the meal. Each of these actions, and their relevance to diabetes self-management, may suggest linking or unlinking (and therefore start a new initiating episode) episodes. Using a combination of these criteria, the example data is allocated, and shown in FIG. 24. This allocation establishes three "episode chains," all initiated, in this example, by Rise episodes (11/4/006, 8:56 AM; 11/5/06, 6:57 AM; 11/13/06, 9:16 PM).

Figure 25:
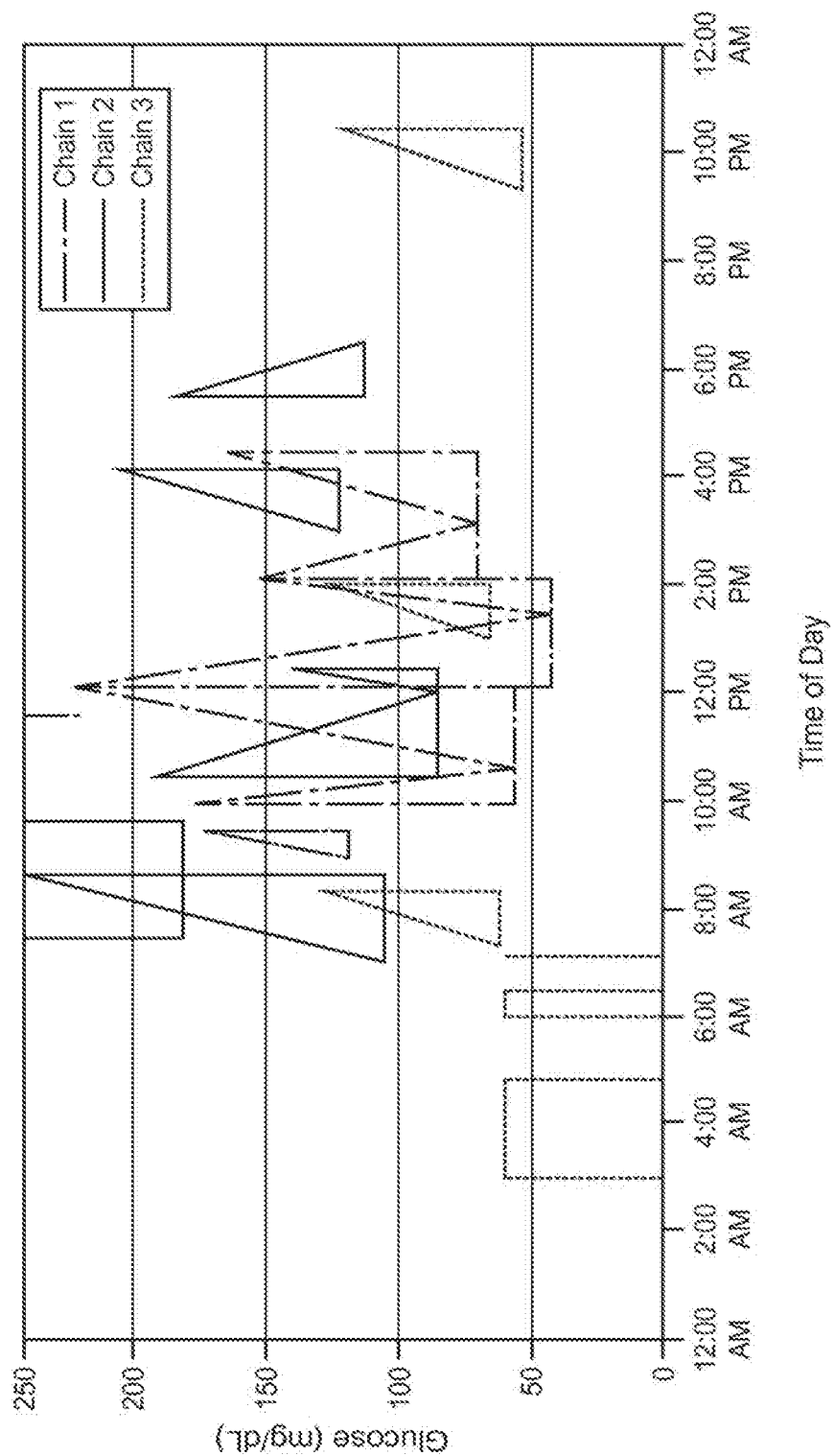
FIG. 25 is a chart illustrating glucose levels versus time of day.

For the purposes of reviewing and displaying episode chains, certain embodiments of the proposed invention is to display them relative to time of day, as shown in FIG. 25.

Figure 26:
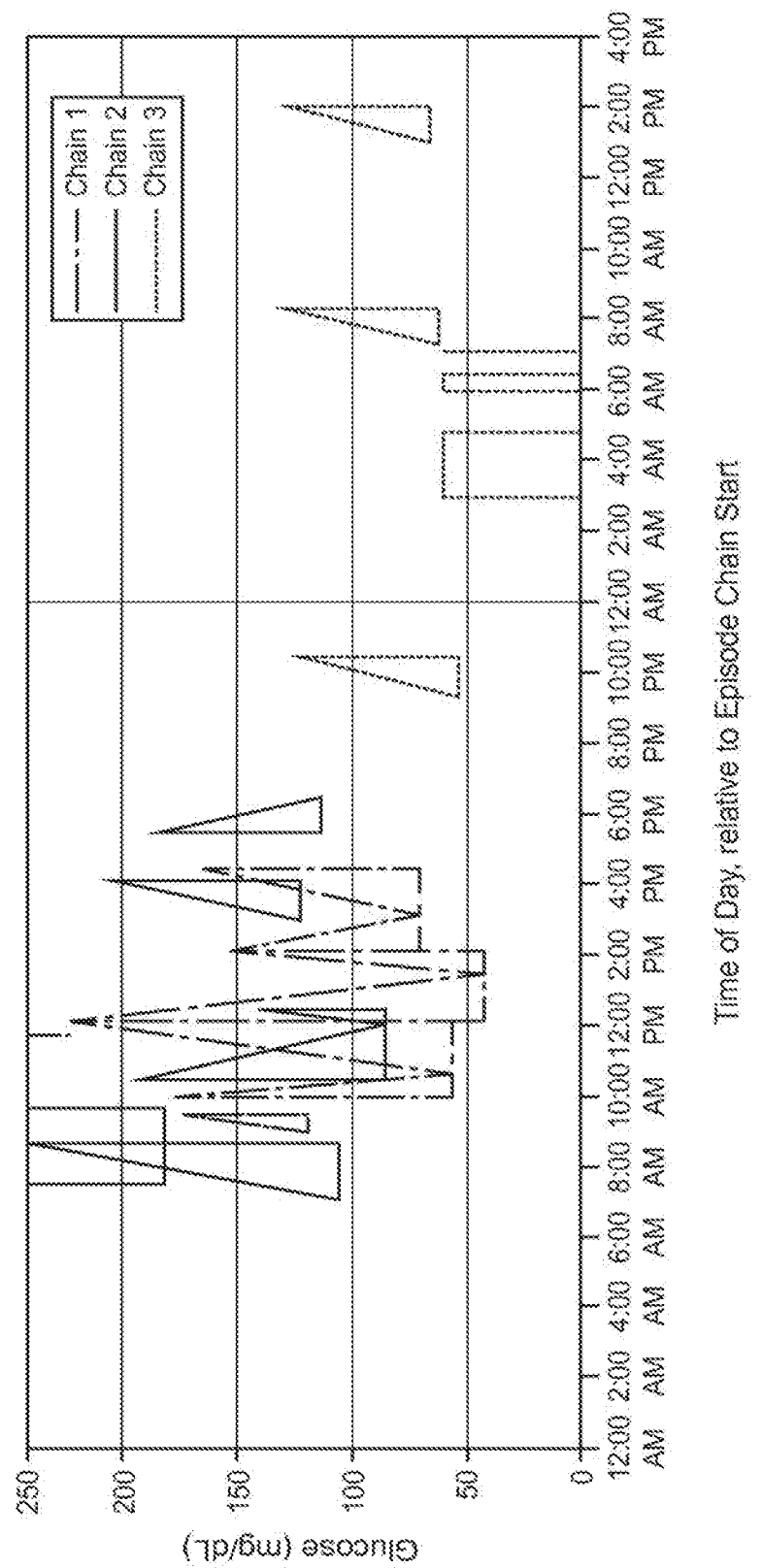
FIG. 26 is a chart illustrating glucose levels versus time of day.

For the purposes of reviewing and displaying episode chains, certain embodiments of the proposed invention is to display them relative to time of day and time of episode chain initiation. In this case, if a follow-on episode occurs after midnight of the chain initiation, it is shown on subsequent 24-hr periods, expanded to cover as many 24-hour periods as necessary to show the entire episode chain. An example is shown in FIG. 26.

Once episode chains have been identified and displayed, the chains can also be automatically, or with clinician guidance, be assigned to clinically relevant categories. This allocation is done according to the attributes of the chain, and may be done automatically to help frame the type of therapy interventions the clinician should likely consider for the individual under his or her care. Examples of possible attributes of the chain that may be considered to include: a) start time (or "time-of-day") of the chain initiator, wherein daytime episodes may have different interventions than nighttime episodes; b) time of day of the chain follow-on episodes, wherein episodes occurring during awake versus sleep periods may be managed differently; c) glucose value at the start of the chain, wherein, for example, Rises that start less than 80 mg/dL may be assumed to be a rapid correction of a low glucose, whereas a Rise that starts above 80 mg/dL may be assumed to be due only to a typical meal intake; d) presence or absence of a continuous glucose monitoring threshold or projected glucose alarm, wherein, for example, a Rise following a glucose alarm may indicate appropriate or inappropriate management of low glucose situations; e) order of the types of episodes in the chain, wherein, for example, a "High-High" chain would be allocated differently than a "High-Loud" chain; and f) user actions (or inactions) before or during the chain, wherein, for example, an action may be eating, taking medication, exercising, or other actions that may affect their diabetes management and glucose control.

This invention would be incorporated into glucose data management software, either "on device" or external to the glucose monitoring device. It would primarily be targeted to health care providers who guide therapy decisions to manage glucose levels. It would aid in investigating and relating clinically significant glucose measurements of interest with particular behaviors or therapy choices that their patient is performing. From there, the clinician may use his or her judgment to suggest effective actions for the patient to take to mitigate the observations and improve their disease control.

Software Application for Estimating Impact of Glucose Monitoring Alarm Adjustments In certain embodiments, there is provided a method for estimating the impact of glucose monitoring alarm adjustments on glycemic control.

People who monitor their glucose with continuous glucose monitoring systems that have real-time glucose alarms are faced with the trade-off of optimally setting the high glucose alarm to achieve glycemic control goals without being burdened by excessive alarms. Excessive alarms can lead to "alarm fatigue," or "nuisance alarms," whereby the alarms interfere with the patient's daily activities and can often lead to disuse of the monitor. Both patients and HCPs would benefit from a tool that helps establishes the trade-offs inherent in setting the high glucose alarm, sets expectations of the frequency of alarm while taking measures to improve glycemic control, and estimates potential benefits of improved glucose control.

Provided herein is a method for retrospectively analyzing glucose data to estimate the potential improvement in glucose control if the high glucose alarm were adjusted lower, while estimating the increased number of alarms that the patient may expect to have to manage. Given a set of continuous glucose measurements for a patient (typically 5 days or more), the method iteratively lowers a theoretical high glucose alarm threshold, for example from 240 to 160 mg/dL in 20 mg/dL steps. At each iteration, glucose values that exceed the high glucose alarm setting are replaced with the value of the high glucose alarm setting. Then, the overall average glucose is calculated to estimate the improvement in glucose control that may be expected at that high glucose alarm setting. Thus, at each iteration of the high glucose alarm setting, at least two values are output: 1) estimated average glucose; and 2) estimated number of high glucose alarms. The number of high glucose alarms may be normalized across time, for example, the number of high glucose alarms per day. More detailed summaries of the estimated glucose control may also be calculated. For example, the hourly average glucose across a "modal 24-hr day" may be calculated, to see how changes in the high glucose values will change the typical 24-hr profile of the glucose.

The patient and clinician can review the analysis and make a more informed decision of the value of activating the high glucose alarm at a lower value, both the potential benefits and burdens. Current glucose data management systems do not facilitate estimating the impact of changing the high glucose threshold on the overall glycemic exposure a patient may expect. This method improves the understanding of the trade-off of more vigilance towards treatment of high glucose and tolerance of increased high glucose alarm occurrences with expected long-term reduction in excessive glucose exposure.

Figure 27:
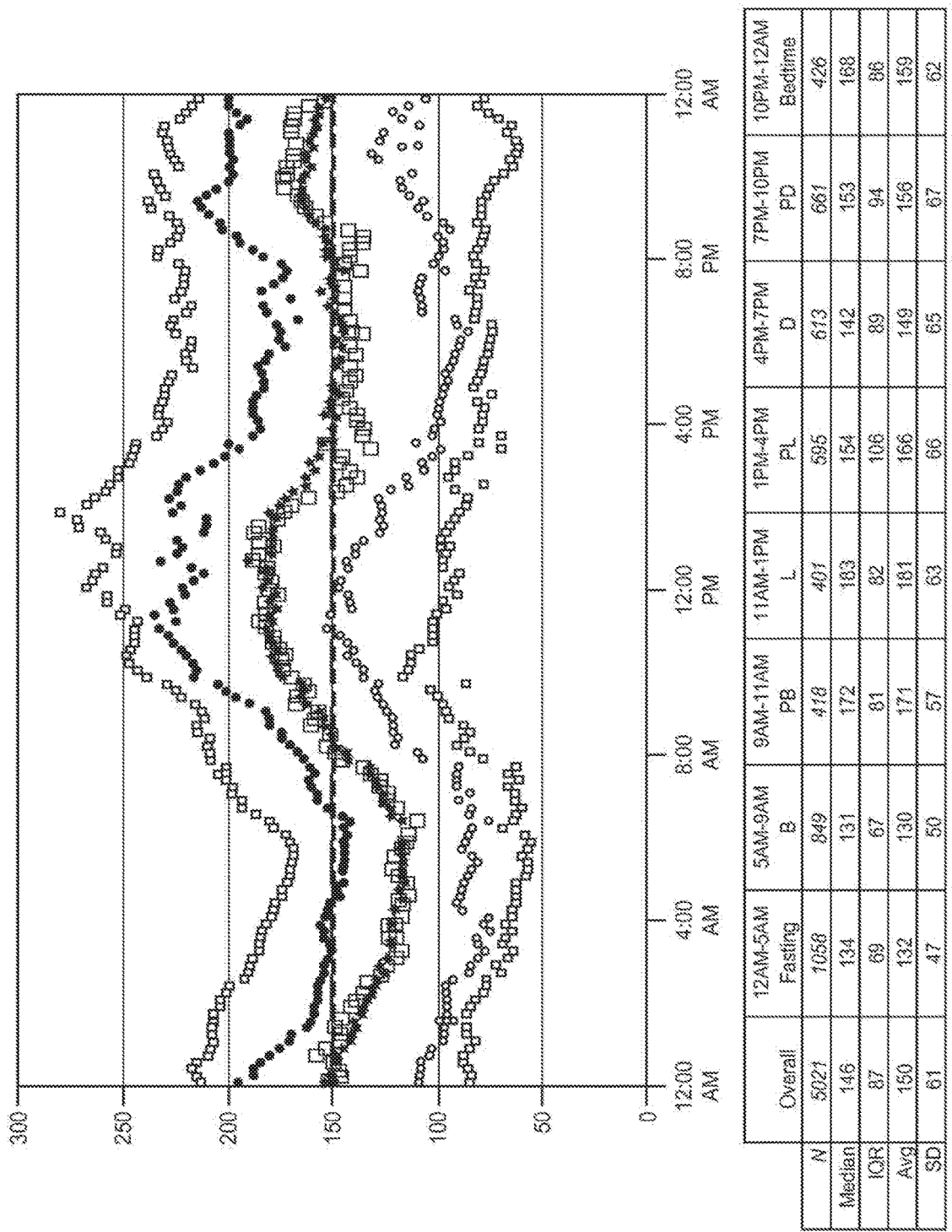
FIG. 27 exemplary data in accordance with one method presented herein.
Figure 28:
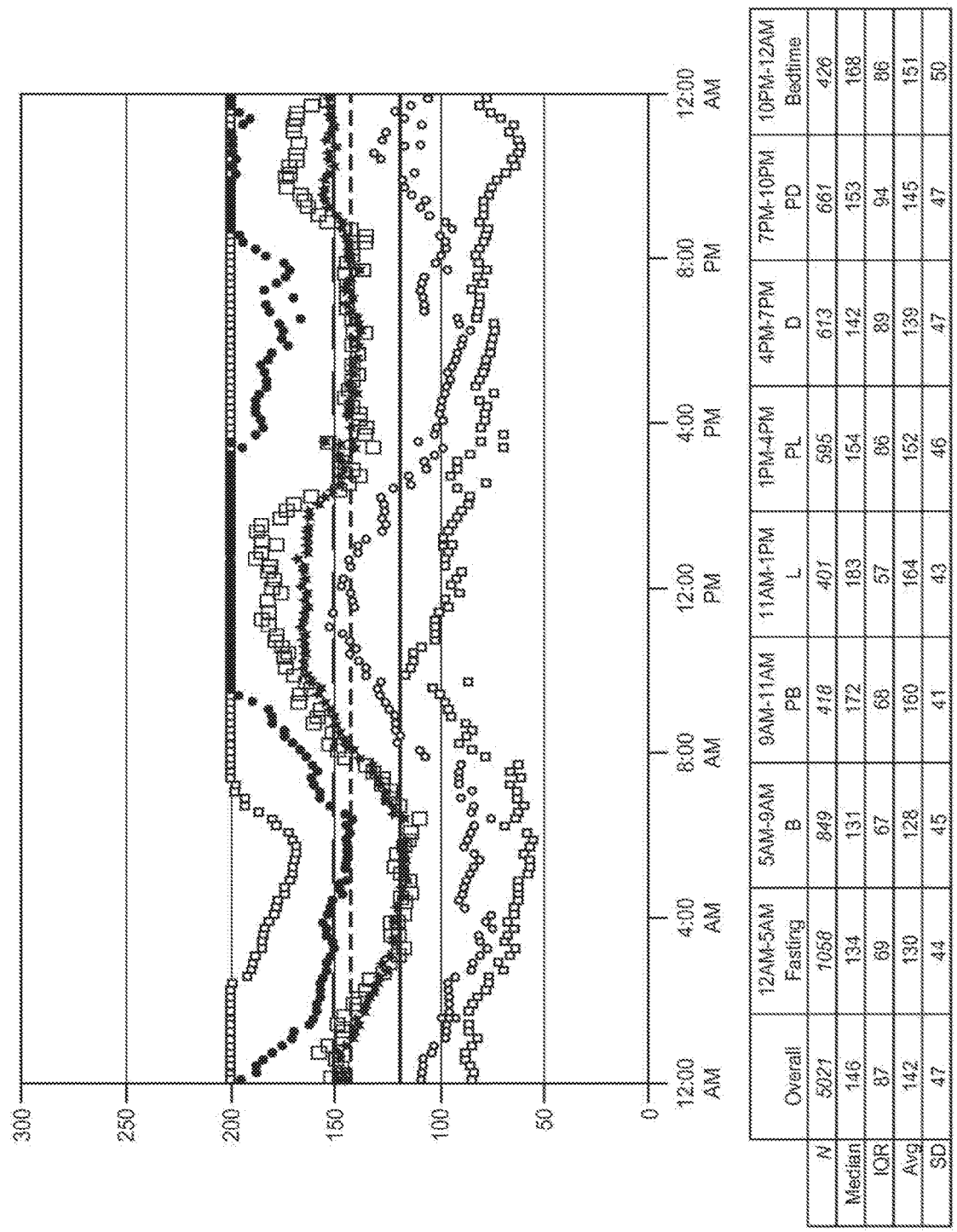
FIG. 28 exemplary data in accordance with one method presented herein.
Figure 29:
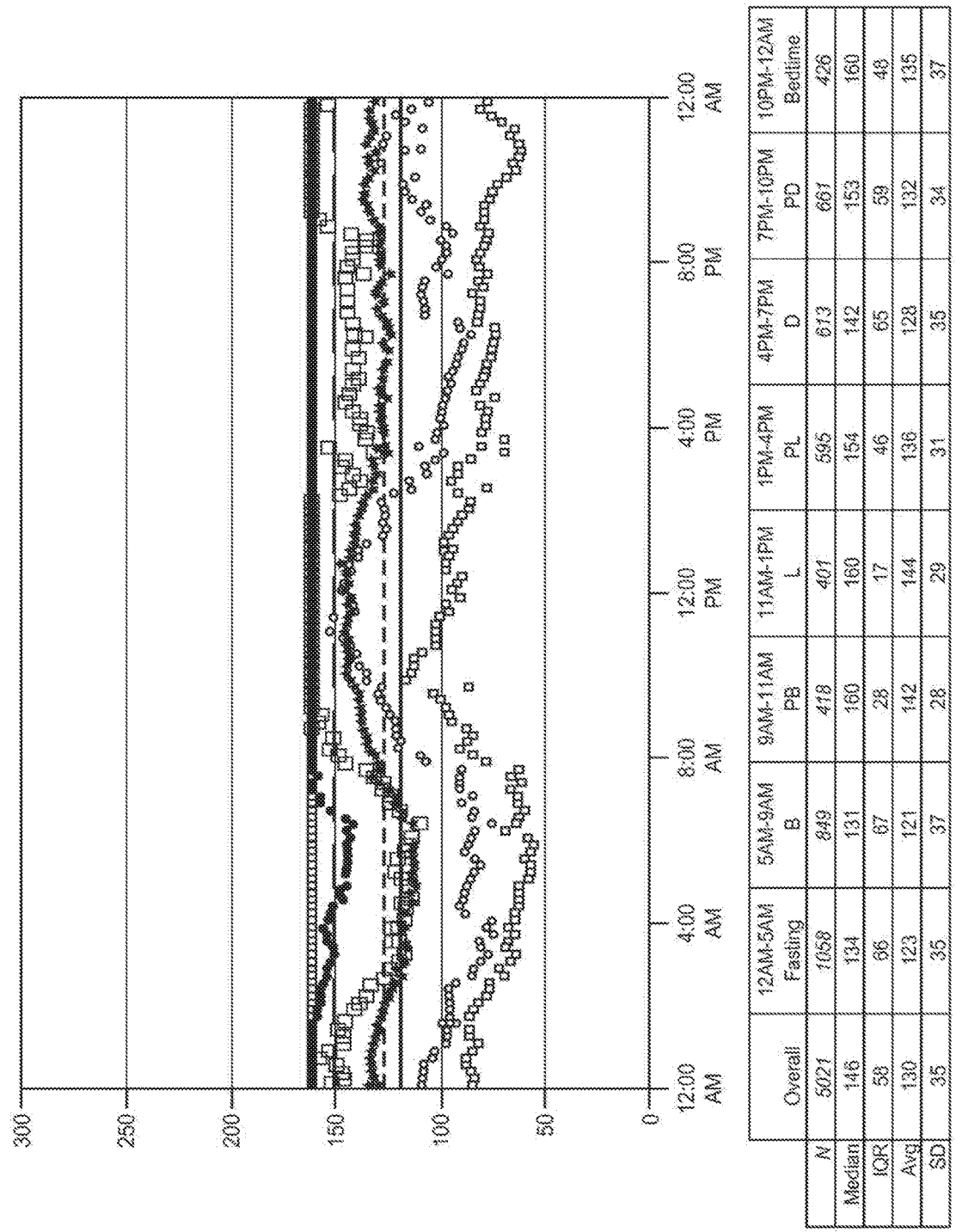
FIG. 29 exemplary data in accordance with one method presented herein.

FIGS. 27-29 show an example of three iterations of the method. FIG. 27 shows an example of "original" data, that is, no replacement of glucose values by the high glucose setting has occurred. This data may or may not have had the high glucose alarm activated. If it were, then the actual experience of glucose alarm activation may be summarized. FIG. 28 shows an example of the hourly glucose distribution after estimating the impact of setting the high glucose alarm to 200 mg/dL. The estimated overall average glucose is seen to move closer to the target average glucose. Also, the hourly average glucose is seen to be impacted during parts of the day when the glucose was elevated above the high glucose alarm setting. FIG. 29 extends the example for the setting of the high glucose alarm to 160 mg/dL.

More specifically, FIG. 27 is a modal plot of glucose, and summary statistics table, with original data (no estimation of alarm change). Plotted are the 90th (gray open squares), 75th (gray solid squares), 50th (black solid squares), 25th (gray solid squares) and 10th (gray open squares) percentile lines, the hourly average glucose (red dots), the overall average glucose (black horizontal dashed line), predicted average glucose (red horizontal dashed line), and target average glucose (green horizontal line), over the 24-hour period. FIG. 28 is a modal plot of glucose and summary statistics table, estimation of high glucose alarm change to 200 mg/dL. Plotted are the 90th (gray open squares), 75th (gray solid squares), 50th (black solid squares), 25th (gray solid squares) and 10th (gray open squares) percentile lines, the hourly average glucose (red dots), the overall average glucose (black horizontal dashed line), predicted average glucose (red horizontal dash line), and target average glucose (green horizontal line), over the 24-hour period. The predicted average glucose has been reduced by 8 mg/dL compared to the overall average glucose. FIG. 29 is a modal plot of glucose and summary statistics table, estimation of high glucose alarm change to 160 mg/dL. Plotted are the 90th (gray open squares), 75th (gray solid squares), 50th (black solid squares), 25th (gray solid squares) and 10th (gray open squares) percentile lines, the hourly average glucose (red dots), the overall average glucose (black horizontal dashed line), predicted average glucose (red horizontal dashed line), and target average glucose (green horizontal line), over the 24-hour period. The predicted average glucose has been reduced by 8 mg/dL compared to the overall average glucose.

Figure 30:
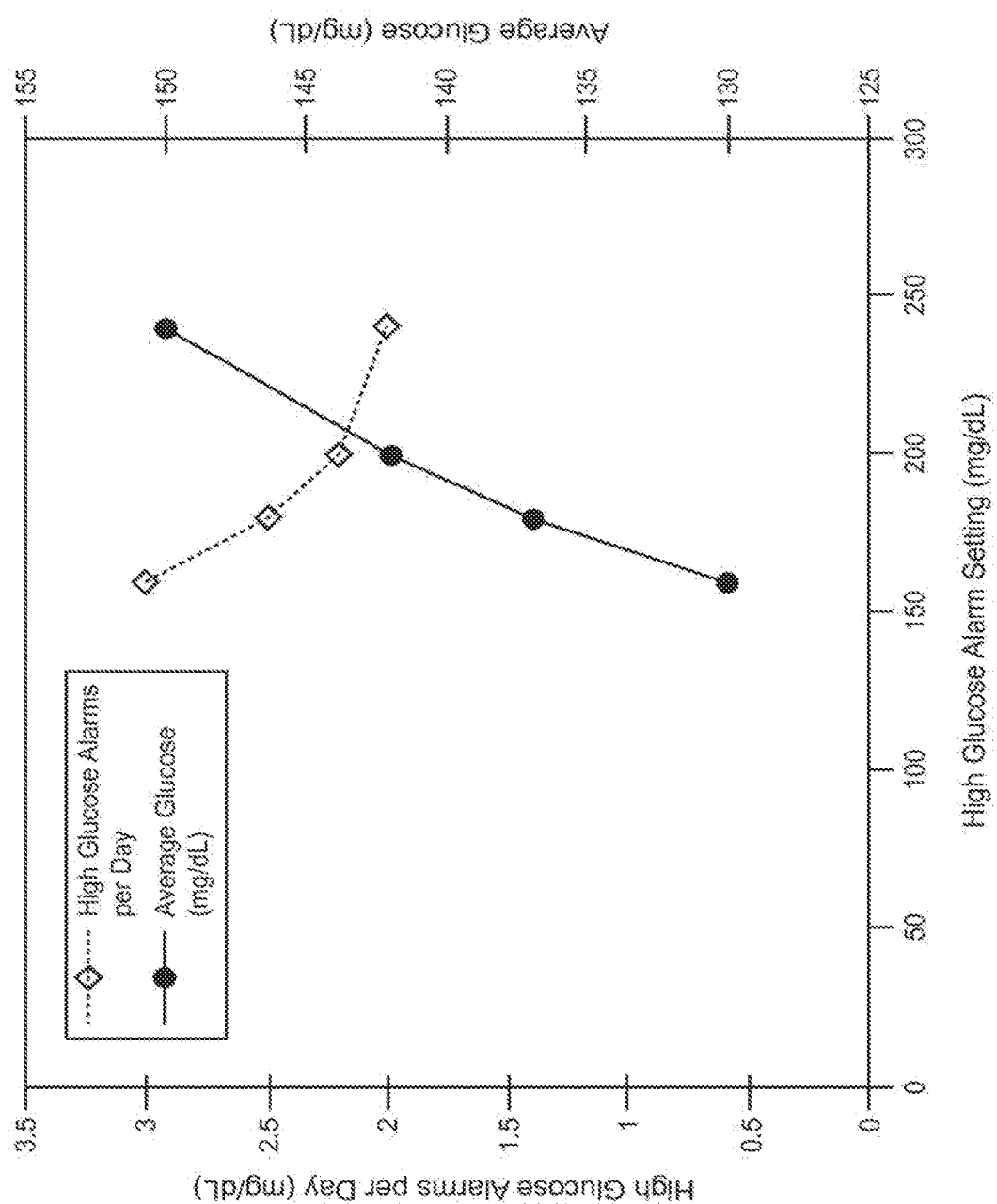
FIG. 30 is a plot of high glucose alarms per day versus high glucose alarm setting.

FIG. 30 shows a summary of estimated impact of high glucose alarm setting on high glucose alarms per day and average glucose. More specifically, FIG. 30 shows an example summary of iterations of estimating the impact on average glucose and number of high glucose alarms as the high glucose alarm setting is changed. It may be assumed that the right-most data point is either "actual" (experienced by the patient while wearing the device) or "simulated," for example if the patient has not activated the high glucose alarm during the monitoring period that is being reviewed. As the high glucose alarm setting is reduced, the overall average glucose is reduced, and the number of glucose alarms increases. However, the invention here proposes estimating these values from individual monitoring (e.g., CGM) data, and therefore is more personalized than population-based methods or other methods that summarize other patients high glucose alarm frequency.

Glucose Metric Mappings to Diabetes Treatment Recommendations

In some aspects of the present disclosure, there is provided a method of mapping metrics generated from glucose results in a manner for determination of an appropriate treatment recommendation or modification for a patient based on the glucose results. For example, the metrics are mapped and the appropriate treatment determined such that the risk of hypoglycemia is taken into account and minimized. Furthermore, in some aspects of the present disclosure, there is provided a device or system that implements such methods and/or displays such mapped metrics generated by such method. For example, such method may be implemented as software within a CGM or SMBG device or system that is executed by one or more processors in the device or system. It should be appreciated that the following discussion relating to the mapped metrics may apply to the method of mapping the metrics, as well as the device or system that implements such methods and/or displays such mapped metrics generated by such method.

In certain embodiments, the metrics used are glucose median and glucose variability, calculated for a specified period of time. Variability (or volatility) may be estimated using many different possible metrics. For following example, the lower 40% percentile is used to represent variability. Median is chosen as it is less sensitive to outliers than the mean. However, it should be appreciated that mean or other type of average, or other metric that represents central tendency of data, may be used in other embodiments.

The Glucose Control Grid

The glucose median and variability may be illustrated graphically where, for instance, the median is represented along the y-axis and the variability is represented along the x-axis. As described below, this graph is divided up into zones that represent possible treatment recommendations. This graph is referred to herein as the "control grid" or "control chart". These zones may be, for example, represented mathematically and implemented in software to provide automated therapy recommendations based on glucose data. In addition, the control grid itself may be displayed to the health care provider (HCP) and/or patient by the software.

Figure 31:
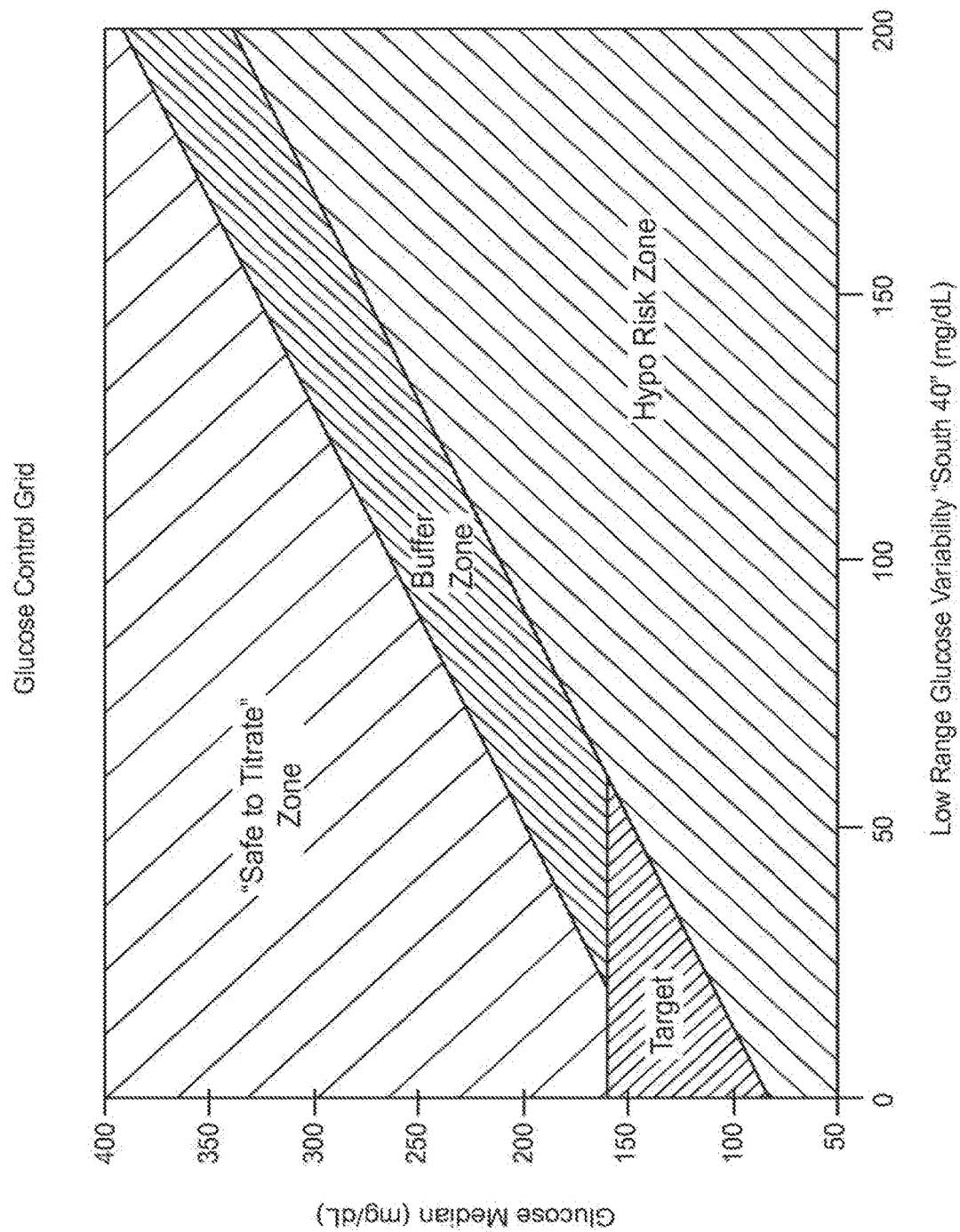
FIG. 31 illustrates a control grid, according to certain embodiments.
Figure 32:
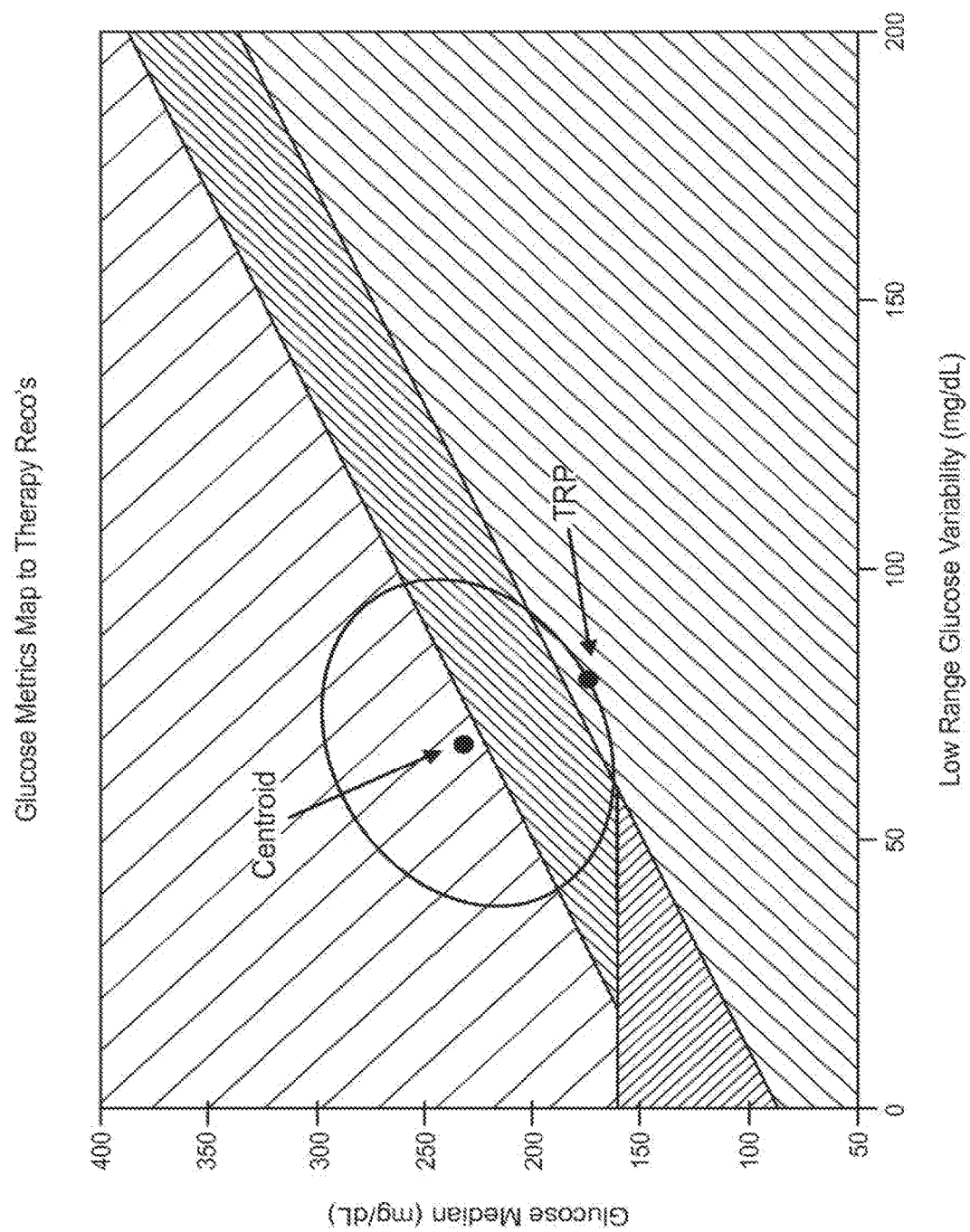
FIG. 32 illustrates a control grid displaying a centroid, according to certain embodiments.

FIG. 31 illustrates a control grid, according to certain embodiments. The control grid includes glucose median on one axis and variability on the other axis. A patient's glucose median and variability can be plotted as a point on the control grid. The uncertainty in the estimate of the median and variability may be plotted here, for instance, as represented by a cloud of points, or a "bubble", or some other representation, as described herein. For example, in some instances, a boundary line for the cloud of points may be displayed in place or in addition to the cloud of points. These metrics are compared to the lines defining the zones—e.g., the Hypoglycemia Risk Zone, Target Zone, Buffer Zone, and "Safe to Titrate" Zone, as described below. It is appreciated that there are many possible metrics that can be used for comparison, such as the centroid or "best estimate" of the metric, or the confidence point (e.g., 95% confidence point) of the metric (referred to as the Treatment Recommendation Point—TRP), as illustrated in FIG. 32. Other possible metrics can be readily contemplated.

On the control grid shown in FIG. 31 there are four zones defined. In certain embodiments, the Hypo Risk zone is defined as the region below the hypo risk line where it is determined that, if the TRP falls below, the patient is at an unacceptable risk of hypoglycemia. In this case, the displayed treatment recommendations would be related to reducing the patient's glucose variability and/or increasing the patient's glucose median. For instance, one specific recommendation related to reducing glucose variability would be for the patient to eat more regularly. A specific recommendation related to increasing glucose median may be to reduce the dose or dose rate of glucose-lowering medication, for example.

The Target zone is the ultimate goal for the patient and HCP (e.g., doctor or other health care professional). In certain embodiments, the Target zone is defined as being above the Hypo Risk line and below a Target line—the Target line can be adjusted by the HCP to provide an achievable treatment goal appropriate for a particular patient. For example, in certain embodiments, the patient is in the Target zone if a) the TRP is not below the Hypo Risk line and b) the metric centroid falls within the Target zone.

In certain embodiments, the Buffer zone is defined as the region above the Target zone and the Hypo Risk zone, but below a line defined as an offset above the Hypo Risk zone. This offset is representative of the possible or expected drop in median due to an increase in glucose-lowering mediation, for example. For instance, this zone may represent the region where, if the TRP was contained within it, it would be unsafe to recommend an increase in medication, since it may drive the patient into the Hypo Risk zone, assuming that glucose variability did not change. In such case, for example, the displayed recommendation may be related to reducing the patient's glucose variability.

In certain embodiments, the "Safe to Titrate" zone is defined as the region where the TRP is above the Buffer zone and above the Target zone. For example, here the recommendation may be related to increasing the patient's glucose-lowering medication dose in order to reduce their median glucose.

Figure 33:
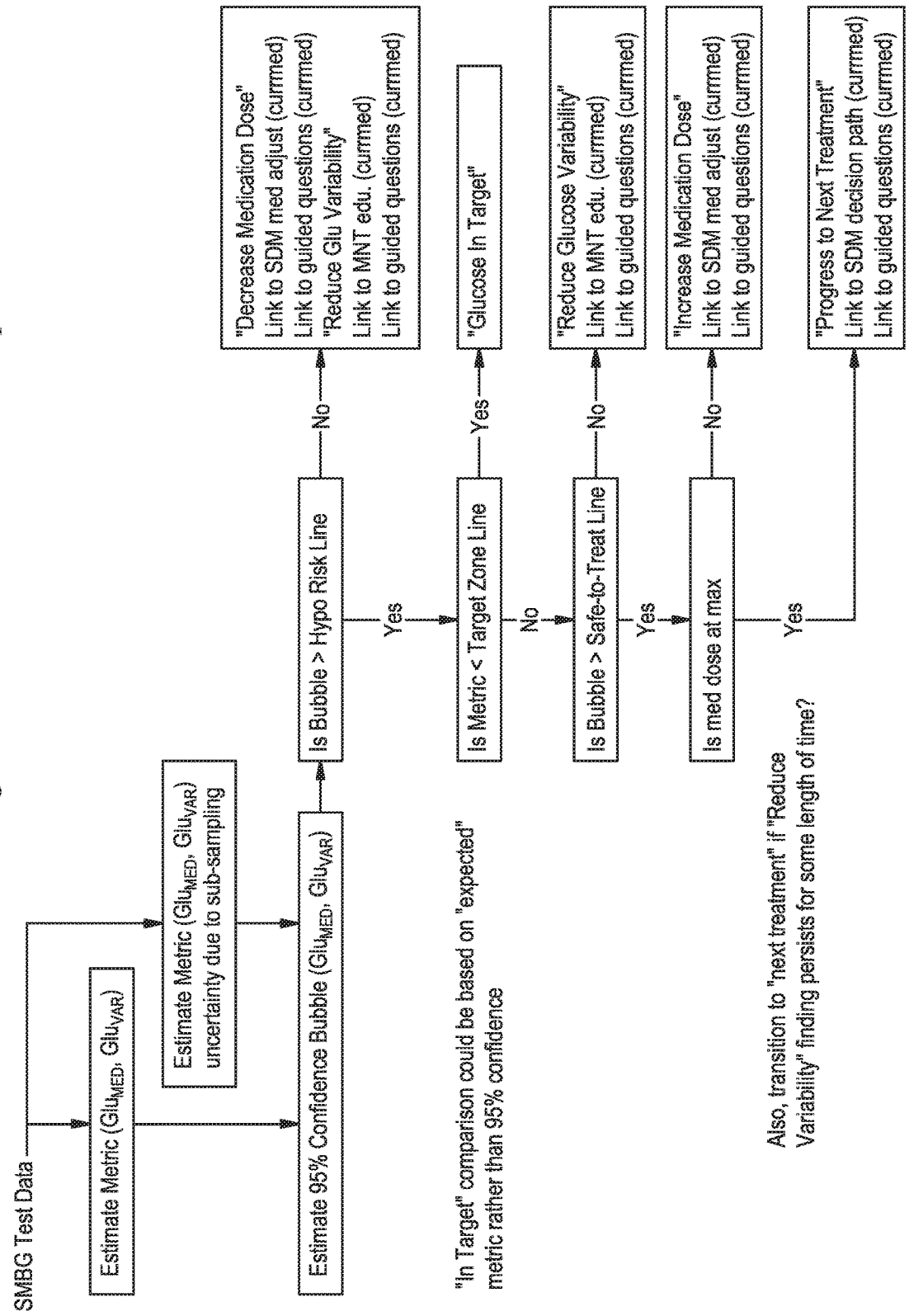
FIG. 33 illustrates a flowchart for a method of recommending treatment, according to certain embodiments.

FIG. 33 illustrates a flowchart for a method of recommending treatment using mapped metrics, according to certain embodiments. In the embodiment shown, SMBG test data is provided and a metric (e.g., glucose median and variability) is estimated as well as the metric uncertainty due to sub-sampling. A confidence bubble (e.g., 95% confidence bubble) is estimated and compared to the various zones (e.g., hypo risk zone, target zone, safe-to-treat zone) to determine an appropriate treatment recommendation. In some instances, the "in-target" comparison may be based on "expected" metric rather than 95% confidence. Further, the current medication dosage may be considered in determining the appropriate treatment recommended.

It should be appreciated that the embodiments shown are exemplary and that the control grid may be fashioned a number of different ways in other embodiments. For example, the straight lines in the embodiments shown may be curve—e.g., the Hypo Risk line.

Figure 34:
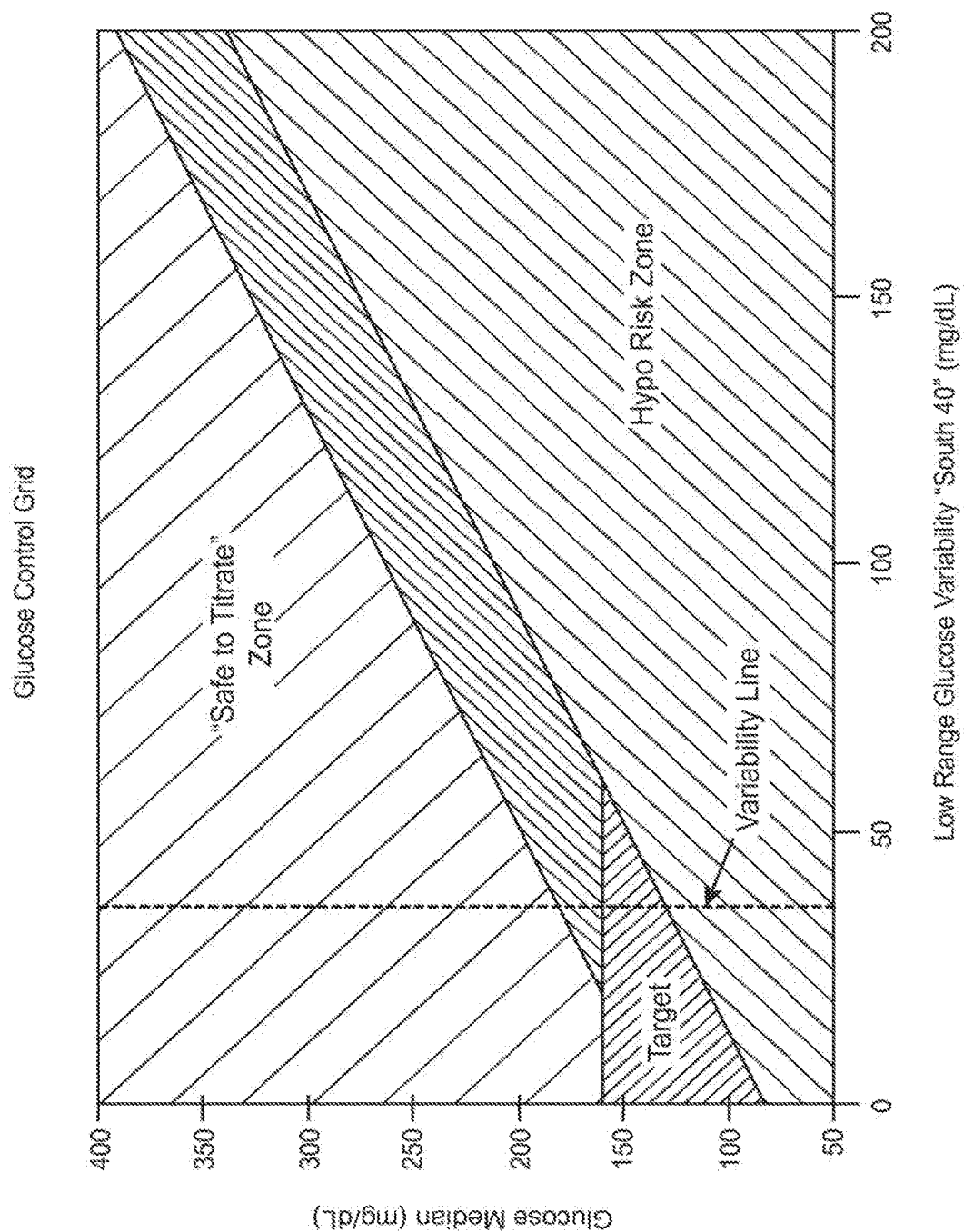
FIG. 34 illustrates a control grid, according to certain embodiments.

As another example, a control grid embodiment is shown in attached FIG. 34 which illustrates two modifications to the previous Control Grid embodiment shown in FIG. 31. The first modification is the removal of the Buffer zone and replacement with recommendations displayed that specifically indicate the distance from the Hypo Risk line. For instance, for a TRP that is located 30 mg/dL above the Hypo Risk line in the "Safe-to-Titrate" zone, the recommendation may read "Increase dose of glucose-lowering medication, margin to safely reduce median glucose is 30 mg/dL". The modified recommendations may indicate both the margin above and below the Hypo Risk line. For instance, for a TRP that is located 10 mg/dL below the Hypo Risk line, the recommendation may read "Decrease dose of glucose-lowering medication, a 10 mg/dL increase in median glucose is needed to reduce hypoglycemia risk to a safe level". Alternatively, the recommendation may indicate the positive or negative horizontal distance from the Hypo Risk line, in terms of variability reduction. Combinations of these are also contemplated. In some instances, one reason to eliminate the fixed buffer zone is that dose increments may achieve different glucose median reductions, depending on the medication used or the patient's physiology. Another embodiment is to provide a mechanism where the HCP can modify the Buffer zone depending on these factors that could impact glucose median reductions.

The second modification to the Control Grid shown in attached FIG. 34 is the addition of a vertical Variability line used to drive variability related recommendations. In the control grid shown, some or all of the zones are further divided into sub-zones. In the sub-zones where the centroid metric is to the right of the Variability line, variability related recommendations are provided. Where the centroid metric is to the left of the Variability line, variability related recommendations are not provided. The Variability line may be defined as fixed at a specific location on the x-axis; that is, at a specific variability value. In certain embodiments, the x-axis location of the Variability line depends on the Target line and/or the Hypo Risk line. For instance, the location may be determined by the intersection of the Target line and the line defined as 50 mg/dL above the Hypo Risk line. This provides for variability recommendations appropriate for the target set for a specific patient.

In some embodiments, a control grid includes a buffer zone at an offset above and/or below the Hypo Risk line. For instance, if the TRP is within this zone, then the recommendations does not include a recommendation for medication adjustment. Outside this zone, the recommendation includes a medication adjustment recommendation. In some embodiments, a control grid includes a zone defined by the Hypo Risk zone divided by the Target line. For example, for a centroid metric above this line, the recommendation does not include decreasing medication; but below the line, the recommendation includes decreasing medication. It should be appreciated that these embodiments are exemplary and demonstrate how alternative zones may be designed and utilized in various embodiments.

In some embodiments, zones may also indicate multiple recommendations at varying degrees of importance. The degree of importance may be indicated, for example, by the order in which they are listed, or by color coding the recommendations, or by any other appropriate means.

In some embodiments, recommendations may also include other factors not directly related to treatment. For example, the recommendations may pertain to the need to increase SMBG sampling frequency. Additional sub-zones may be included in the control grid, for instance, such that when the TRP is below the Hypo Risk line, but the centroid metric is above the Hypo Risk line, the recommendation includes reduction in variability and the need to increase sampling frequency in order to reduce uncertainty in the metric. The sampling frequency increase recommendation may also be generated by comparing the size of the "uncertainty bubble" to a predetermined size and if the bubble crosses one or more of the lines on the grid, then an increase in sampling frequency is recommended, for example. Various measures of "uncertainty bubble" size may be contemplated, including a figure of merit of the distance between the centroid and the TRP.

Configuration of Control Grid Logic

In some aspects of the present disclosure, the parameters of the control grid may be modified by the HCP. For example, the software that implements the automated therapy recommendation logic provides an interface, such as a popup screen or window, for the HCP to modify the control grid—e.g., alter the lines on the control grid, select certain features of the control grid, etc. For instance, in certain embodiments, the HCP may select from a list of possible Target levels and Hypo Risk levels. The Target levels on the list may be associated with various diabetes complication statistics such as corresponding A1c. For instance, it may be more acceptable for a patient with A1c of 10% to have a near-term target of 9% rather than 7% so as not to be discouraged. The Hypo Risk levels may be adjusted as necessary to tailor to a patient's tolerance of hypoglycemia. The Hypo Risk pick list labeling may be associated with expected frequency of hypoglycemia, a relative measure of hypoglycemia risk such as High, Medium, Low, or any other appropriate labeling.

In the software, the Recommendation algorithm may be initially run with default parameters (either predefined in the code or set to the last algorithm run for that patient from a previous doctor's visit). In some embodiments, a popup window or other interface may be provided to allow the HCP to alter one or more of these algorithm input parameters as needed, and the algorithm is rerun, generating new recommendations.

Control Grid by Time of Day

In some aspects of the present disclosure, the control grid based algorithm is used to process data for specific time periods of the day or relative time periods related to key events. For example, four key time periods may be defined as overnight/fasting (12 am-8 am), post breakfast (8 am-12 pm), post lunch (12 pm-6 pm), and post dinner (6 pm-12 am). Glucose data collected for multiple days can be grouped into these time periods and the control grid algorithm run for each group. In this way, recommendations that are specific to time periods may be generated. For instance, variability recommendations may be generated specific to meals or overnight. For patient's whose treatment is multiple daily injections (MDI) of insulin, the time-period targeted recommendations may be specific to insulin needs during these times of day. For instance, the control grid for the over-night/fasting period may indicate that medication dosage should be increased; the recommendation may indicate that the patient's long-acting insulin dose should be increased.

Figure 35:
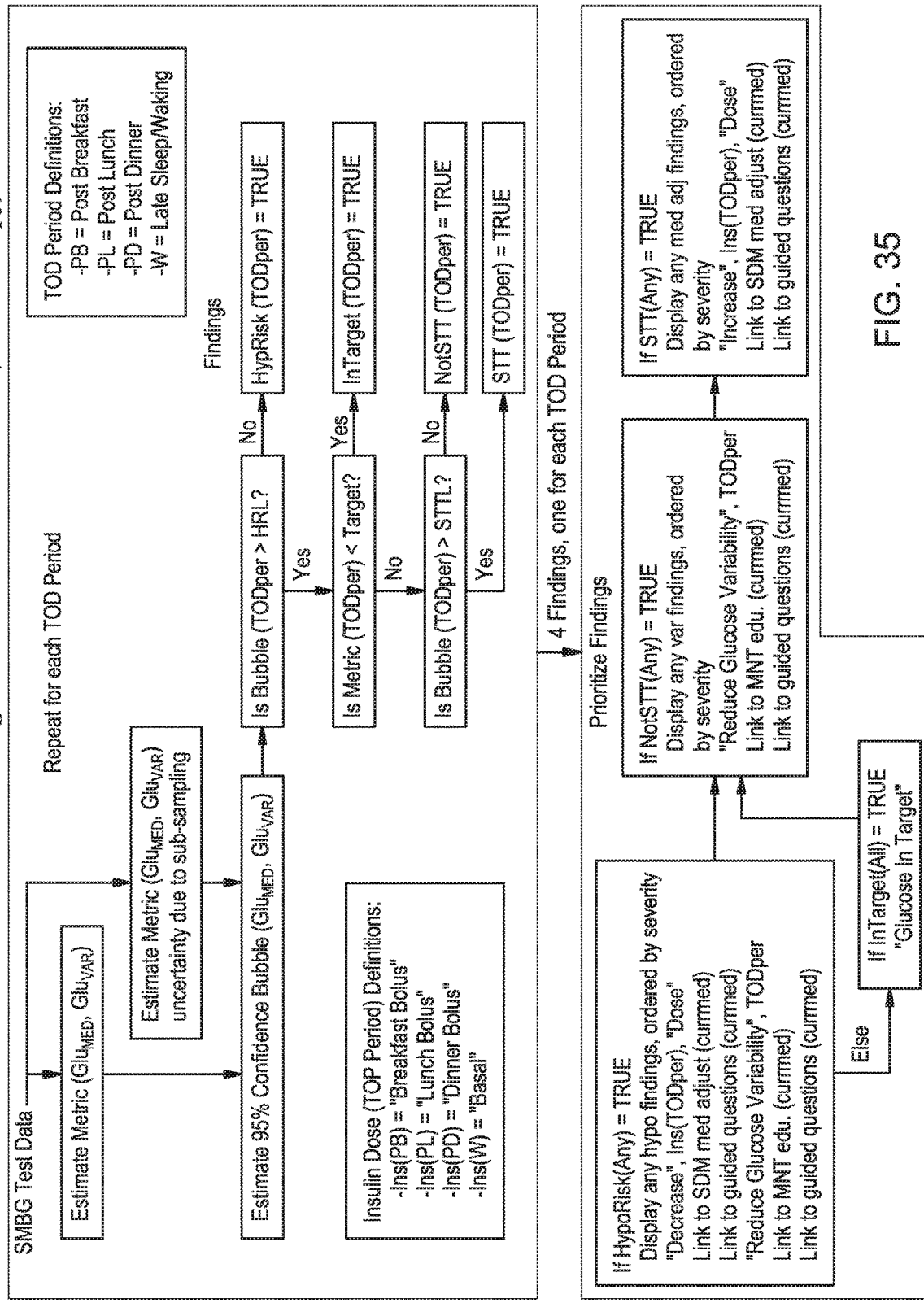
FIG. 35 illustrates a flowchart for a method of recommending treatment with multiple control grids, according to certain embodiments.

In some instances, multiple control grids may be used. The treatment recommendation logic may in some cases be more complicated when multiple control grids are used. An example of this logic is shown in the attached FIG. 35. In the embodiment shown in FIG. 35, the method is repeated for different time-of-day (TOD) periods—e.g., post breakfast (PB), post lunch (PL), post dinner/early sleep (PD) and late sleep/walking (W). The results from each time period analysis may be used to determine an appropriate treatment recommendation. For example, as shown, the results for each time-of-day period may be prioritize and/or weighed to determine the appropriate treatment recommendation.

In some aspects of the present disclosure, the control grid algorithm is applied to time periods defined relatively to events. For example, data grouping may be determined a) 4 hours past breakfast, b) 4 hours past lunch, c) 4 hours past dinner, and d) 4-10 hours past dinner. It should be appreciated that various permutations of this example may be implemented in other embodiments. The data groups may then be processed by the multiple control grid algorithm described above.

Second-Stage Logic to Drive Recommendations

In some aspects of the present disclosure, there is provided an additional logic process to narrow down possible recommendations. For example, the treatment recommendation described above using the control grid algorithm may be augmented to include a second-stage process to further narrow the possible recommendations that may be made. For instance, there are many different recommendations for reducing glucose variability, such as "stop snacking", "don't forget to take your medication", "don't miss meals", "adjust correction dose of insulin". A glucose control zone may be associated with a number of these recommendations. A second-stage process may be implemented to narrow down the list of recommendations. For example, this second-stage process may utilize detection of episodic patterns to narrow the list of recommendations. For instance, if an instance of low fasting glucose is detected preceded by a post-dinner high glucose, this may be an indication of occasional correction dosing to mitigate a high glucose value, and the logic could direct the recommendation to only include "adjust correction dose of insulin". In some instances, the process may require a certain frequency of occurrence of an episodic pattern.

Recommendation Structure and Logic Integrated with Treatment Stage

In some aspects of the present disclosure, the mapping of glucose data to treatment recommendations may be implemented with the use of a lookup table. For example, the inputs to the lookup table are the output of the control grid analysis and the current treatment and treatment stage. The outputs of the lookup table are recommendations of different types that are displayed. FIG. 36 illustrates an example of a treatment recommendation lookup table, according to certain embodiments. For the embodiment shown, multiple recommendations may be associated with a single input combination. It should be appreciated that while a lookup table has been used for exemplary purposes, the concept of a lookup table may easily be extended to more complex glucose metric to recommendation mappings.

In some instances, recommendations may comprise text that is directly displayed, as indicated in the column labeled "Recommended Text" in FIG. 36. In some embodiments, the recommendations may comprise links to source documents and specific pages of the source documents. The content of these source documents may provide more detailed instructions regarding treatment changes. For instance, for a recommendation to change dosage of a medication or a change in treatment, the source document may be published instructions for medication start and adjustment, and the link may be specified to present the appropriate page of these instructions. In some embodiments, recommendations may comprise questions that are displayed—e.g., questions displayed to guide or otherwise assist the HCP in interviewing their patient to uncover underlying issues in self-care management. These questions may be in the form of text to be directly displayed, or reference material. In some embodiments, recommendations may also comprise guidance about testing frequency or how to alter algorithm input parameters. Again, the information is targeted based on analysis of the patient's glucose tests. It should be appreciated that one or more of the various recommendations may be implemented. Further, as illustrated in FIG. 36, recommendations may be tailored to current treatment.

It is appreciated that additional types of recommendations or outputs associated with the inputs to the lookup table may be implemented, including for example: links to sources of definitions, links to appropriate pages of a user guide, links to graphical displays of the data appropriate to illustrate the glucose analysis finding and recommendation, etc. In some instances, for example, the links may be instantiated by the user via buttons (e.g., buttons associated with the recommendation and placed when needed), or they could be instantiated similarly with a hotspot, or could automatically present the linked information in a popup window or a window dedicated for this information.

In certain embodiments when recommendations are to be provided based on multiple time-of-day periods, the structure for the lookup table may be altered. For example, in some instances, this may be done using multiple tables or incorporating multiple algorithm result inputs and multiple associated groups of recommendations into a single table.

In certain embodiments, when a second stage process is employed, the lookup table is adjusted to accommodate the second stage process. For example, if hypoglycemic risk is detected in 3 of the 4 time-of-day periods, rather than display a separate recommendation related to reducing hypoglycemic risk for each time period, the second stage process comprises mapping these into a general recommendation and indicating that it applies to the three time periods.

Software Application for Representing Sample Data for Evaluation and Treatment Recommendation In some aspects, there is provided a method for representing the sample data comprises transforming glucose data from CGM or from SMBG into a location on a plane that measures (e.g., average) glucose level and the amount of variability in the glucose values. In certain embodiments, the method comprises defining the control grid, transforming the data into average glucose and glucose variability (e.g., estimating the average glucose and variability from sample data provided by, for instance, an SMBG device or system), and plotting the transformed data on the control grid.

The following paragraphs describe an example method for representing the sample data, according to certain embodiments. While some of the information describe may be duplicative to that described above; the following description and example embodiments provide further details describing for representing the sample data with, and mapping the metrics on, a control grid. The following example utilizes data derived using blinded CGM data from 66 subjects in a study. It should be appreciated that in other embodiments, a different sample grouping may be used for derivation purposes.

Figure 37:
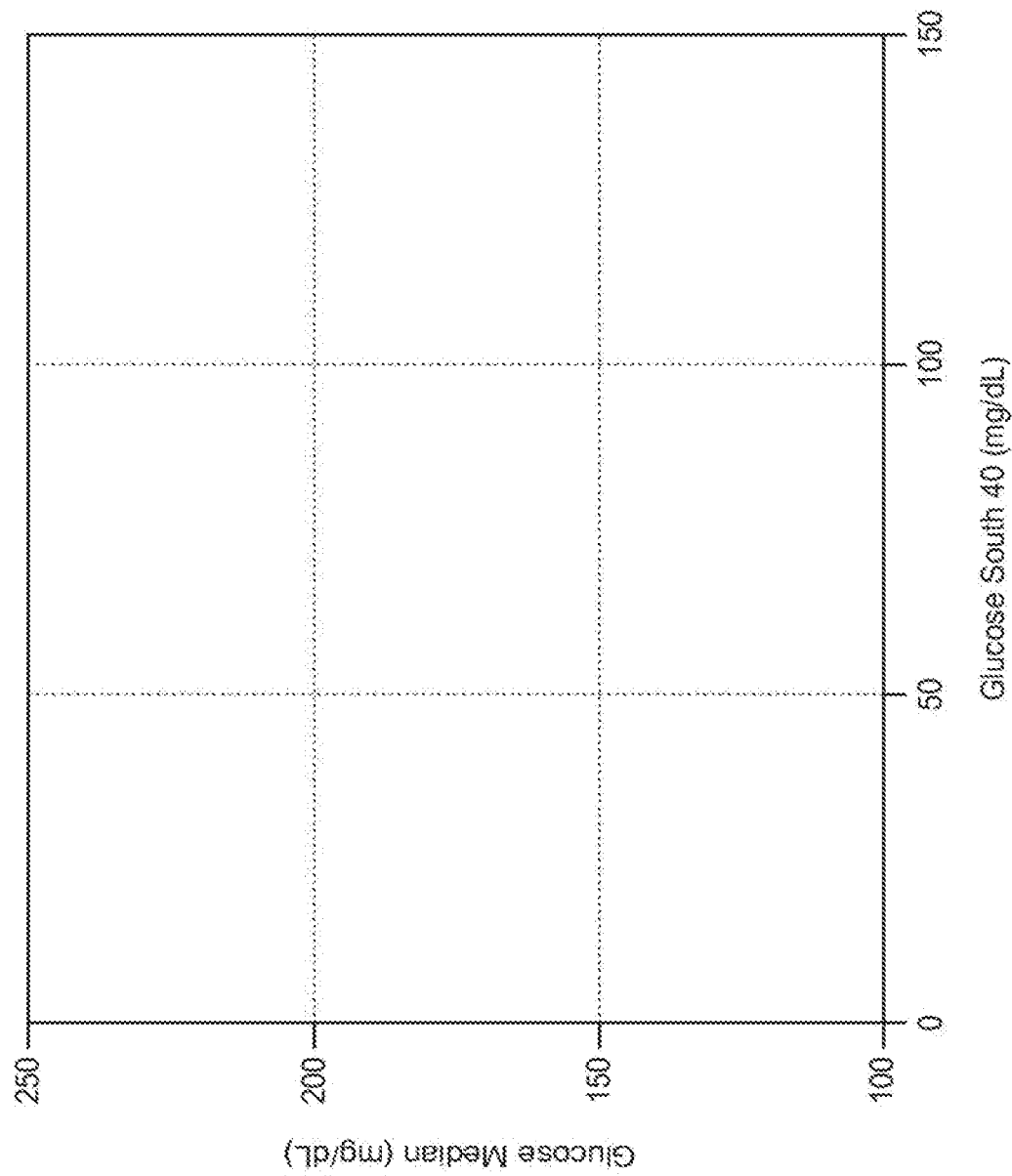
FIG. 37 illustrates a control grid, according to certain embodiments.

In certain embodiments, the method comprises defining a control grid. For example, the control grid is plane upon which glucose level and variability is charted. FIG. 37 illustrates a control grid, according to certain embodiments. In the embodiment shown, the ordinate of the control grid is median glucose. Median glucose is a measure of the glucose level. The abscissa of the control grid is the difference of the median glucose and the 10th percentile value of the glucose, known as the "south 40." This difference is a measure of the glucose variability. It should be appreciated that the ordinate and the abscissa may be different in other embodiments. For example, the abscissa may be the difference between the ordinate (e.g., median glucose) and another reference value for glucose (e.g., a different percentile value other than 10th).

In some aspects, one or more patient risks is represented. Example patient risks may include, but are not limited to, chronic clinical risks such as retinopathy risk, acute risks such as risk of hypoglycemia. For example, for this example, a patient's risk of hypoglycemia (also referred to herein as "hypo") is tracked. In certain embodiments, hypoglycemia is counted in terms of occurrences, rather than, for example, fraction of time spent below a threshold value of glucose. For example, one hypoglycemic occurrence may be defined by a predetermined amount of time below a threshold glucose value—e.g., at least 40 continuous minutes below 60 mg/dl, or at least 30 continuous minutes below 50 mg/dl, or at least 20 continuous minutes below 40 mg/dl; etc. In some instances, requirements may be imposed between two occurrences. For example, in certain embodiments, two occurrences of hypoglycemia are separated by a predetermined minimum amount of time of non-hypoglycemia (e.g., 20 continuous minutes, etc.).

Figure 38:
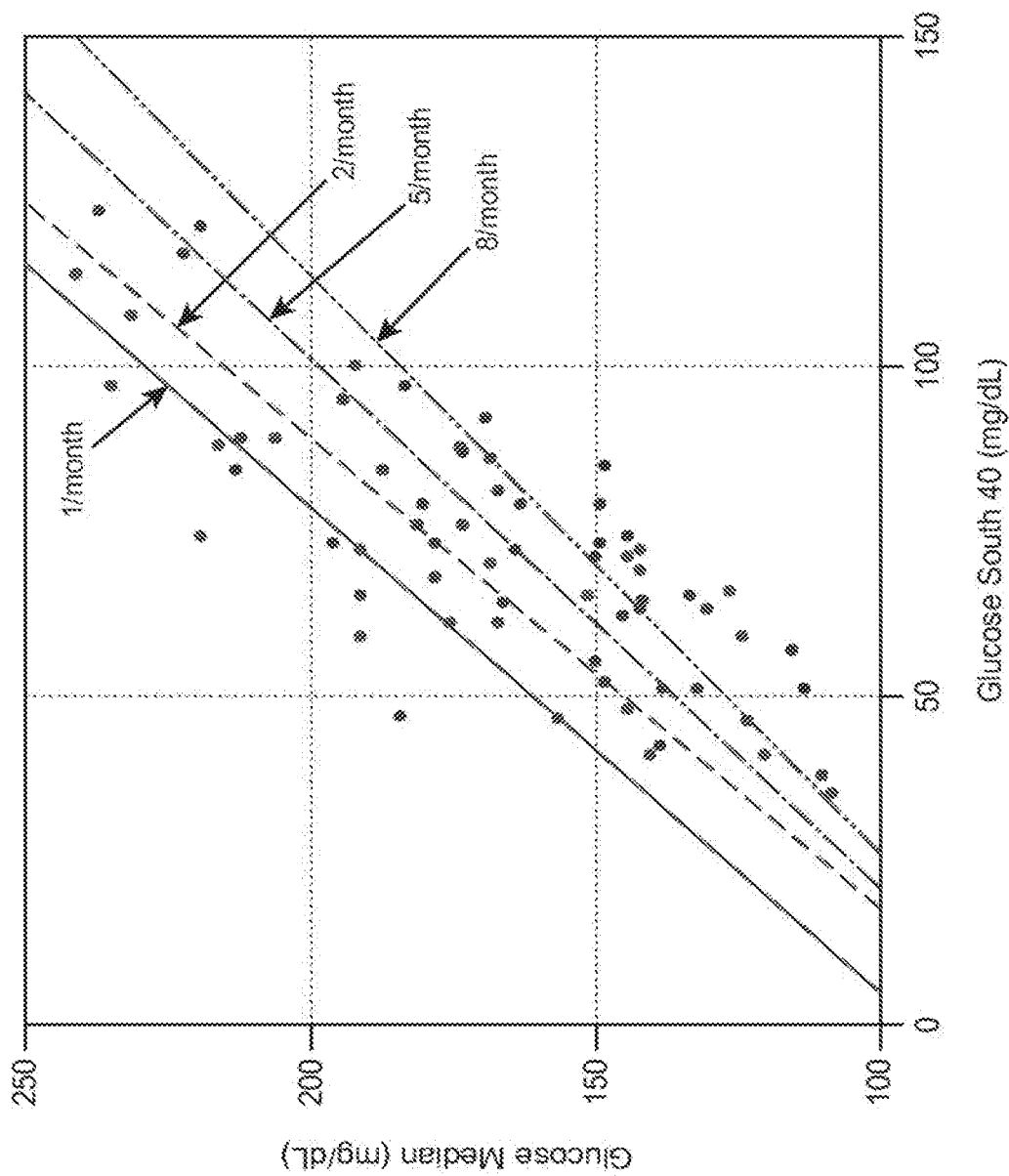
FIG. 38 illustrates a control grid with lines of constant hypoglycemia rate shown thereon, according to certain embodiments.

When occurrences of hypoglycemia are counted and divided by elapsed time to get the rate of hypo occurrences, lines of constant rate of hypo occurrence extend from the lower left of the Control Grid to the upper right. Low rates of occurrence are at the upper left of the grid, where average levels are high and the variability is low. High rates of occurrence are at the bottom right of the grid. Linear classification theory may be used to find straight lines that mark different rates of occurrence. Other methods, such as Support Vector Machines, can also be used. FIG. 38 illustrates a control grid with lines of constant hypoglycemia rate shown thereon, according to certain embodiments. The black dots shown on the control grid represent positions on the grid for the 66 subjects used to derive the lines. Constant lines are shown for 1 occurrence per month, 2 occurrences per month, 5 occurrences per month, and 8 occurrences per month. It should be appreciated that in some embodiments, the control grid may distinguish between different types of diabetes—e.g., one symbol used for Type 2 diabetes mellitus and another symbol for Type 1 diabetes mellitus.

Figure 39:
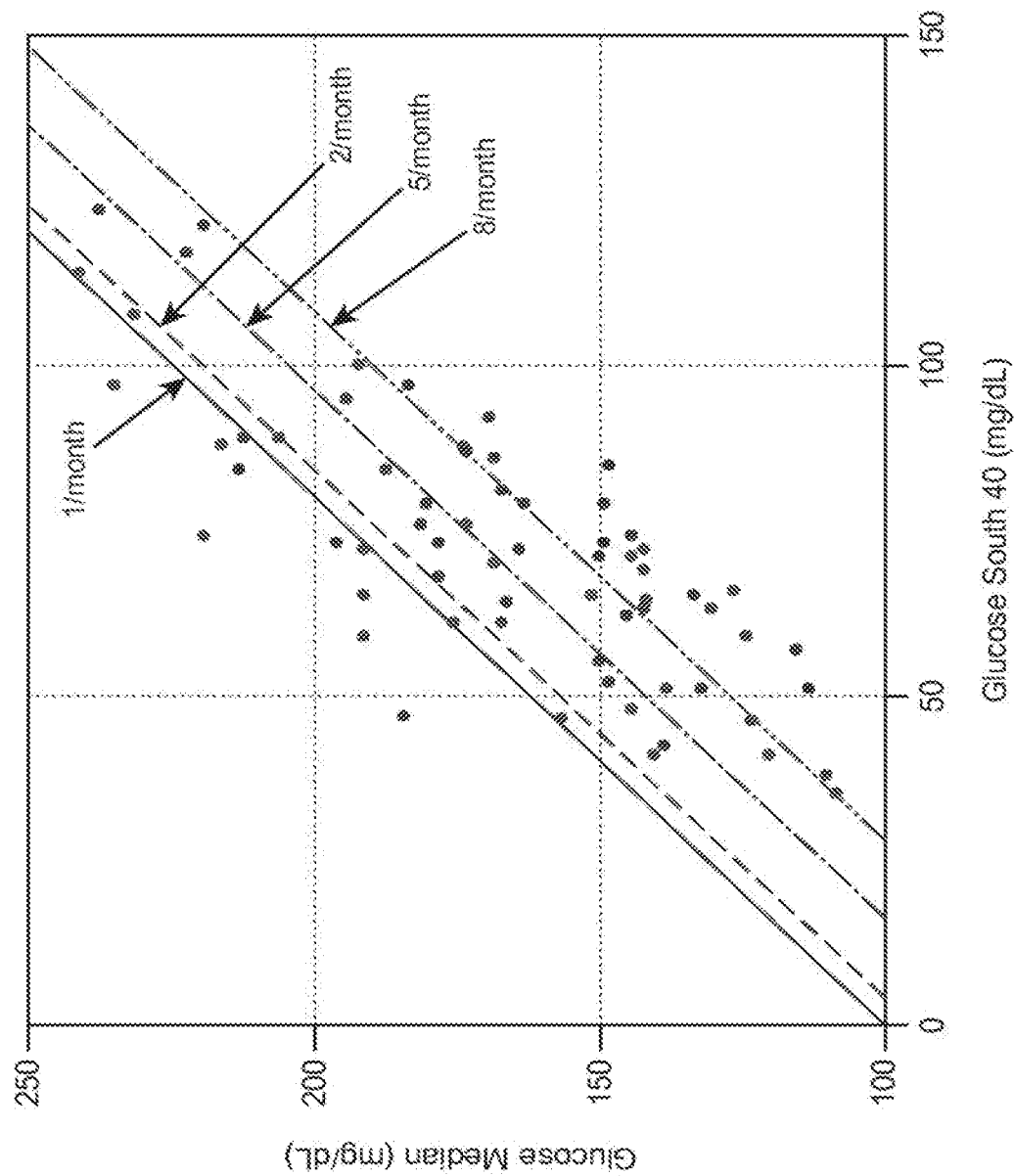
FIG. 39 illustrates the control grid shown in FIG. 32 with parallel approximations of the lines of constant hypoglycemia rate, according to certain embodiments.

In some instances, the lines of constant hypoglycemia rate are adjusted to provide parallel approximations that may be more useful in certain analysis applications. FIG. 39 illustrates the control grid shown in FIG. 38 with parallel approximations of the lines of constant hypoglycemia rate. As shown, the four constant lines are now parallel to one another. A formula may be derived, for instance, such that the lines may be defined according to the rate of hypoglycemia occurrence. For example, the following formula may be used to represent the values of glucose median at a given rate of hypo occurrence:

Glucose Median=104.25−5*(hypo rate)+1.25*(South 40)

where glucose median and south 40 are in mg/dL, and hypoglycemia rate is in occurrences per month.

Figure 40:
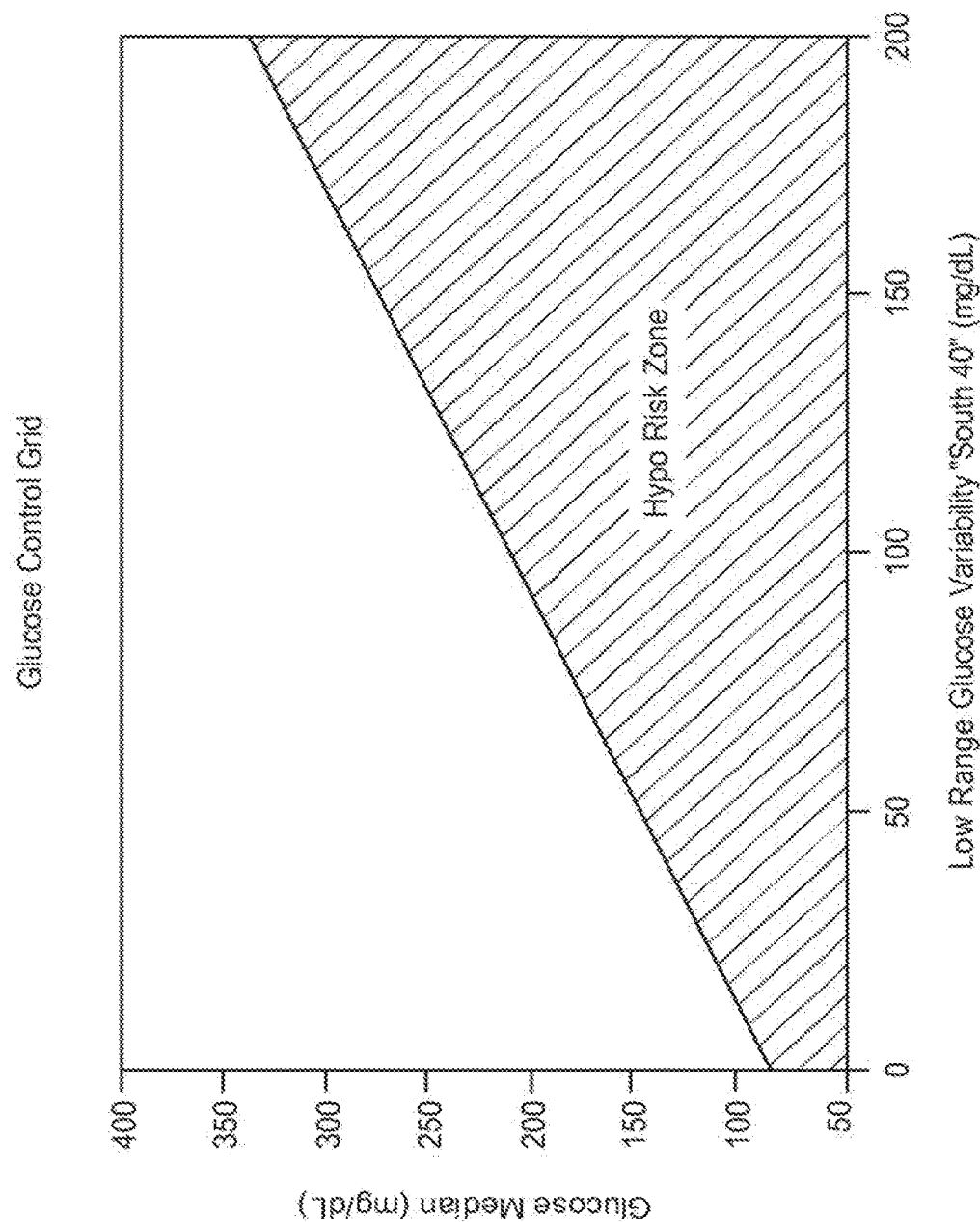
FIG. 40 illustrates a control grid showing a hypoglycemia risk zone (Hypo Risk Zone), according to certain embodiments.

In some aspects, a predetermined rate of hypoglycemia occurrence may be used to represent a danger to the patient. The predetermined rate may be based on a clinical decision, for example. Once a predetermined rate is determined, a control grid can be split into two parts using the predetermined rate. FIG. 40 illustrates a control grid showing a hypoglycemia risk zone (Hypo Risk Zone), according to certain embodiments. The border between the two sections is the line of predetermined hypoglycemia rate. The Hypo Risk Zone may be defined by the border, and patients in the hypo risk zone at the lower right may be determined to have an unacceptable risk of hypoglycemia. The first goal of treatment may be, for example, to get patients out of this area.

Figure 41:
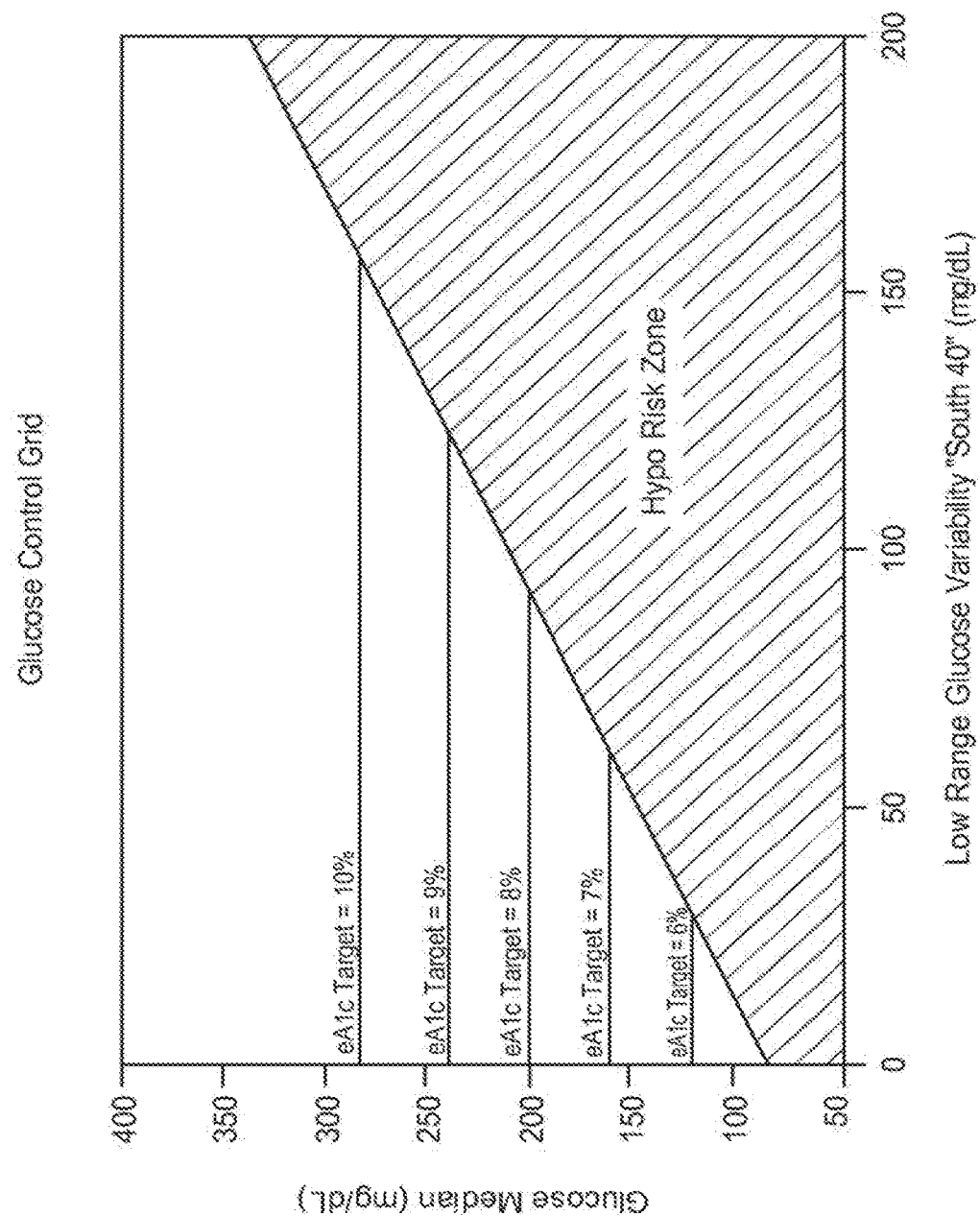
FIG. 41 illustrates possible A1c target values on the control grid of FIG. 34, according to certain embodiments.

In some aspects, a patient's target A1c level is determined and represented on the control grid to provide for a target zone. For example, after setting the Hypo Risk Zone boundary, a clinical decision may determine the patient's target A1c level. FIG. 41 illustrates possible A1c target values on the control grid of FIG. 40, according to certain embodiments. The A1c target value is directly related to the value of the glucose level, and not to the glucose variability, thus the lines are horizontal.

Figure 42:
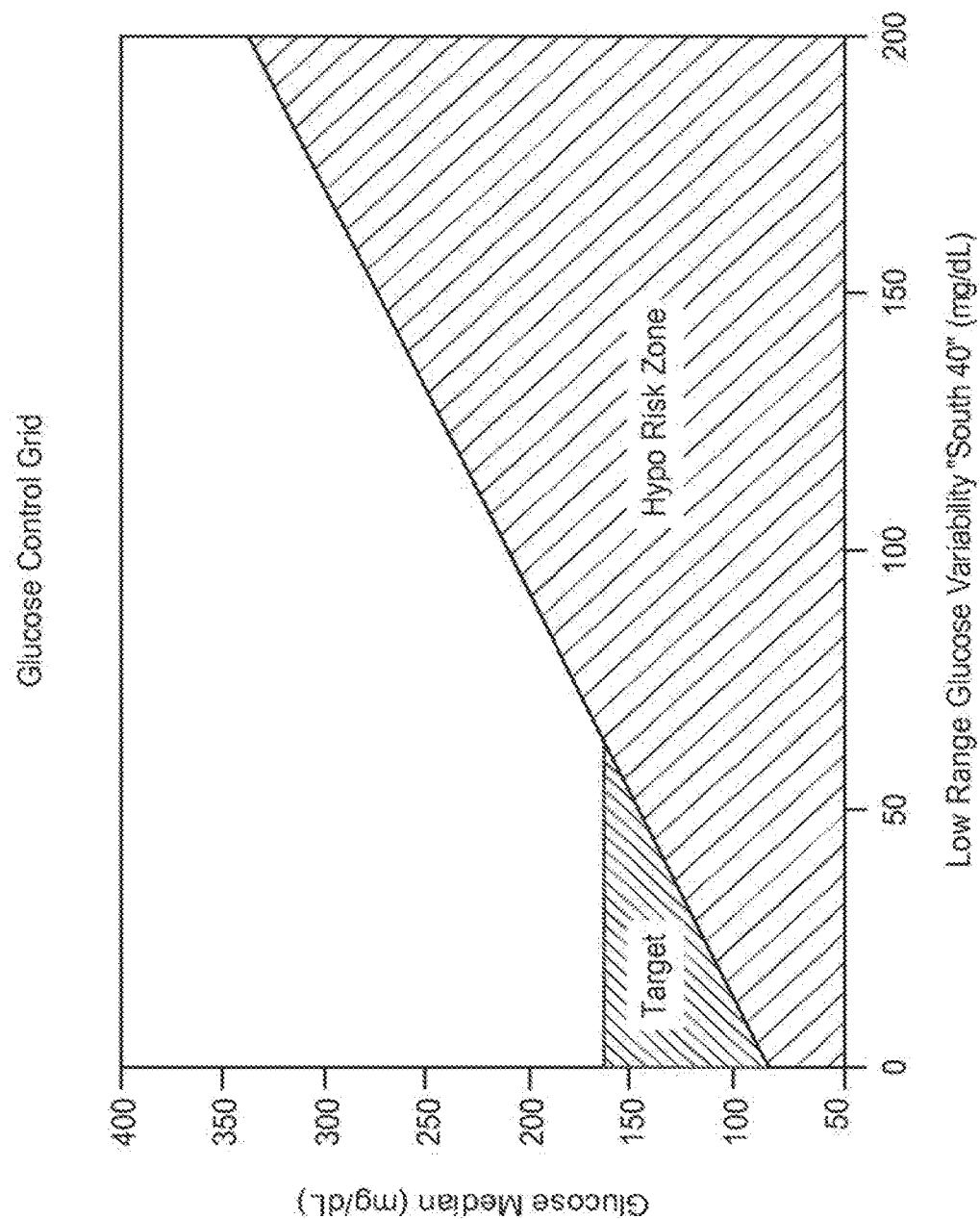
FIG. 42 illustrates the control grid shown in FIG. 35 with a defined target zone, according to certain embodiments.

The target A1c level chosen defines the Target Zone. The area of the control grid below the A1c target value that is not in the Hypo Risk Zone becomes the Target Zone. For example, FIG. 42 illustrates the control grid shown in FIG. 41 with a defined target zone, according to certain embodiments. As shown, an A1c target value of 7% is used and defines a Target Zone on the control grid that is below the horizontal line for a 7% A1c target value but not in the Hypo Risk Zone. In this way, for example, a treatment goal may comprise keeping patients in the Target Zone or moving patients into the Target Zone and keeping them there.

Figure 43:
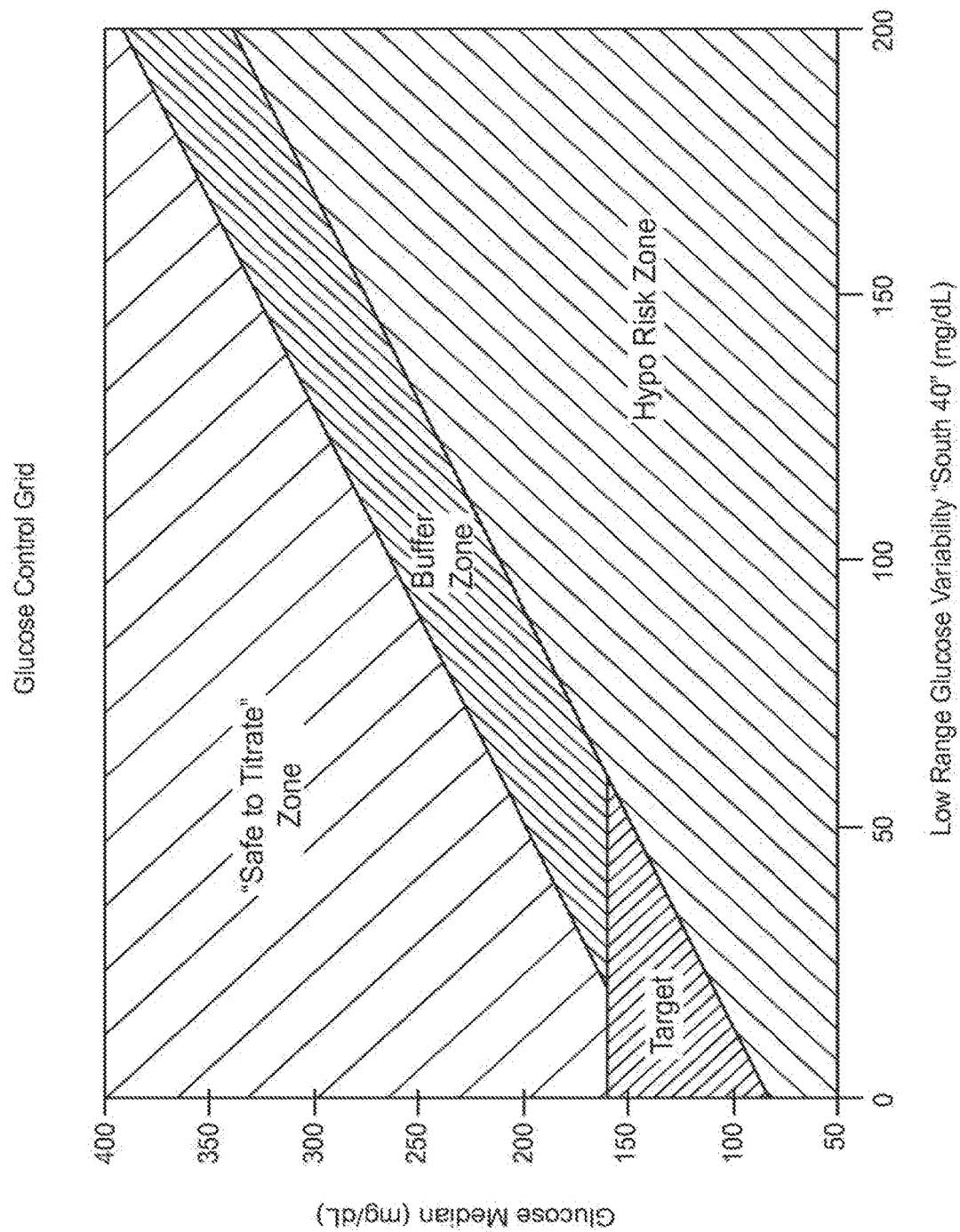
FIG. 43 illustrates the control grid of FIG. 36 with two additional zones, according to certain embodiments.

In some aspects, additional zones are added to the control grid. For example, FIG. 43 illustrates the control grid of FIG. 42 with two additional zones, according to certain embodiments. The control grid comprises a buffer zone and a "Safe to Titrate" Zone. The Buffer Zone includes the area along the border of the Hypo Risk Zone and separates the "Safe to Titrate" Zone and the Hypo Risk zone.

The slope of the Hypo Risk Zone border and the Buffer Zone, and the connection between A1c level and median glucose, may be determined based on, for example, data from CGM studies and journal articles. The actual positions of the boundaries may be determined by, for example, clinical judgment in setting the acceptable risk of hypoglycemia and the target A1c level. These positions may be known, or can be calculated.

In some aspects, the control grid may be used to direct treatment. For example, a strategy may be devised to direct treatment such that the patient avoids the Hypo Risk Zone. For instance, avoiding the Hypo Risk Zone may comprise reducing variability only (move to the left) when in the Buffer Zone, and reducing both variability and median when in the "Safe to Titrate" Zone.

In some aspects, sample data is incorporated within the control grid. For example, the sample data may be transformed or otherwise manipulated for representation on the control grid.

In certain embodiments, sample data is received for a patient. The sample data may originate from various methods, such as SMBG or CGM. The number of data points within the sample may vary. For example, the sample may originate using SMBG and include a small number of data points (e.g., 10 data points). Or, as another example, the sample may originate from CGM and include a larger number of data points (e.g., several thousand).

In certain embodiments, the median and south 40 is calculated from the sample data. The calculated median and south 40 is associated with a single point on the control grid. The calculated median and south 40 are only estimates, and there may be uncertainty as to their accuracy. For example, the south 40 is a difference of two uncertain numbers. Moreover, if the sample size is small, there may be very few values at the low end, and the 10th percentile value may be imprecise.

Figure 44:
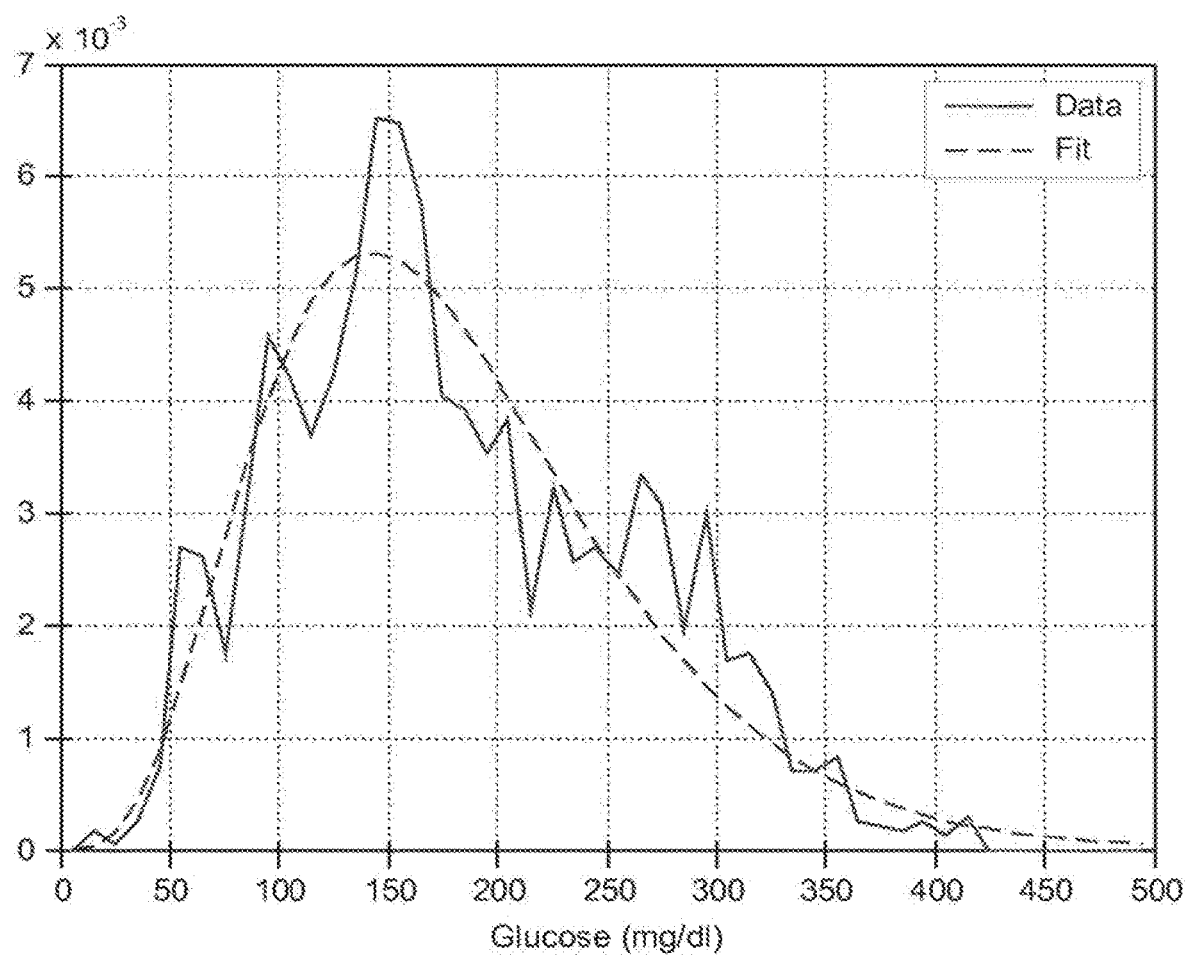
FIG. 44 illustrates a graph of sample data that has been fit to a probability distribution, according to certain embodiments.

In some instances, to reduce such imprecision, the sample data is "fit" to a probability distribution. For example, FIG. 44 illustrates a graph of sample data that has been fit to a probability distribution, according to certain embodiments. The jagged plot for the sample data is shown and follows the sample data points (e.g., CGM data). The plot for the sample data after being fit to a gamma probability distribution is also shown (the smoother plot on the graph). Once the fit has been made, the median and south 40 can be calculated from the distribution. In other instances, a fit is made to a different probability distribution, such as a lognormal or Weibull distribution. In yet other instances, no such fit is made. The median glucose and south 40 are determined directly from the data.

Figure 45:
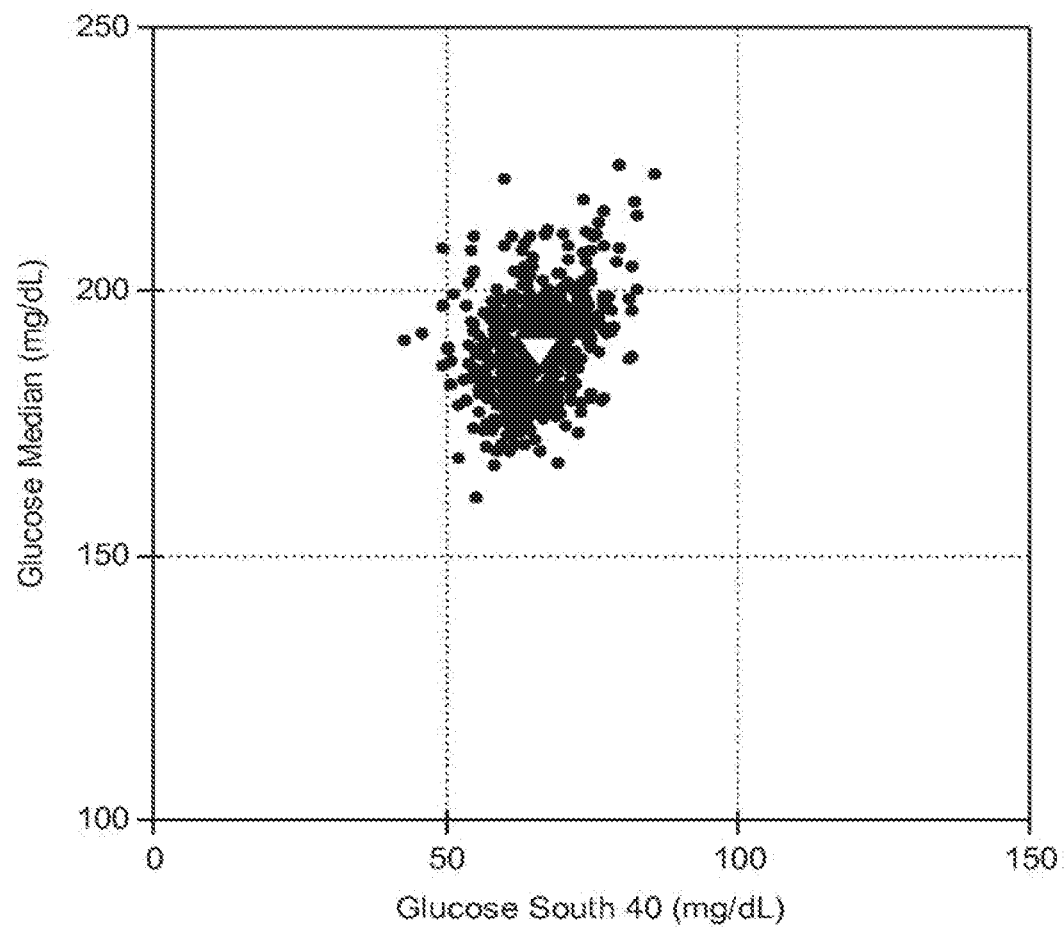
FIG. 45 illustrates a sample point shown on a control grid along with a cloud of points derived by using a bootstrap, according to certain embodiments.

In some aspects, uncertainty in the estimate is calculated. For example, in certain embodiments, uncertainty in the estimate is calculated by using a bootstrap to generate a "cloud" of points around the sample point. FIG. 45 illustrates a sample point shown on a control grid along with a cloud of points derived by using a bootstrap. The sample point is shown on the control grid as a triangle and the circular points surrounding the sample point are bootstrap points. The bootstrap points collectively form a "cloud" of points.

In certain embodiments, a parametric bootstrap is used. For example, the parametric bootstrap may include the following steps:
1. Fit the sample to a gamma distribution, G0.
2. Perform a bootstrap replication
  1. Take random points from G1. Same number of points as sample.
  2. Fit these points to a gamma distribution, G1.
  3. Calculate median and south 40 from G1.
3. Do many bootstrap replications.

Additional information regarding parametric bootstrap may be found in the article entitled, "Performance of the Parametric Bootstrap Method in Small Sample Interval Estimates", by D. Benton and K. Krishnamoorthy (Adv. & Appl. in Stat., 2(3) (2002), pp 269-285), the entirety of which is incorporated herein by reference. Other example ways to generate the point cloud include, but are not limited to, standard (nonparametric) bootstrap, and cross validation (CV) methods, including the jackknife.

In the example shown in FIG. 45, 56 data points make up the sample. Each bootstrap replication drew 56 random points from G0 (defined in step 1 "Fit the sample to a gamma distribution, G0" above). 500 replications were performed, resulting in 500 black dots shown in FIG. 45.

The sample point and bootstrap values represent probability density of patient positions on the Control Grid. Although the triangle is the most likely position, other positions are probable. For example, if the triangle were located on the border of the Hypo Risk Zone, there would be approximately a 50% chance that the patient was actually in the Hypo Risk Zone.

Figure 46:
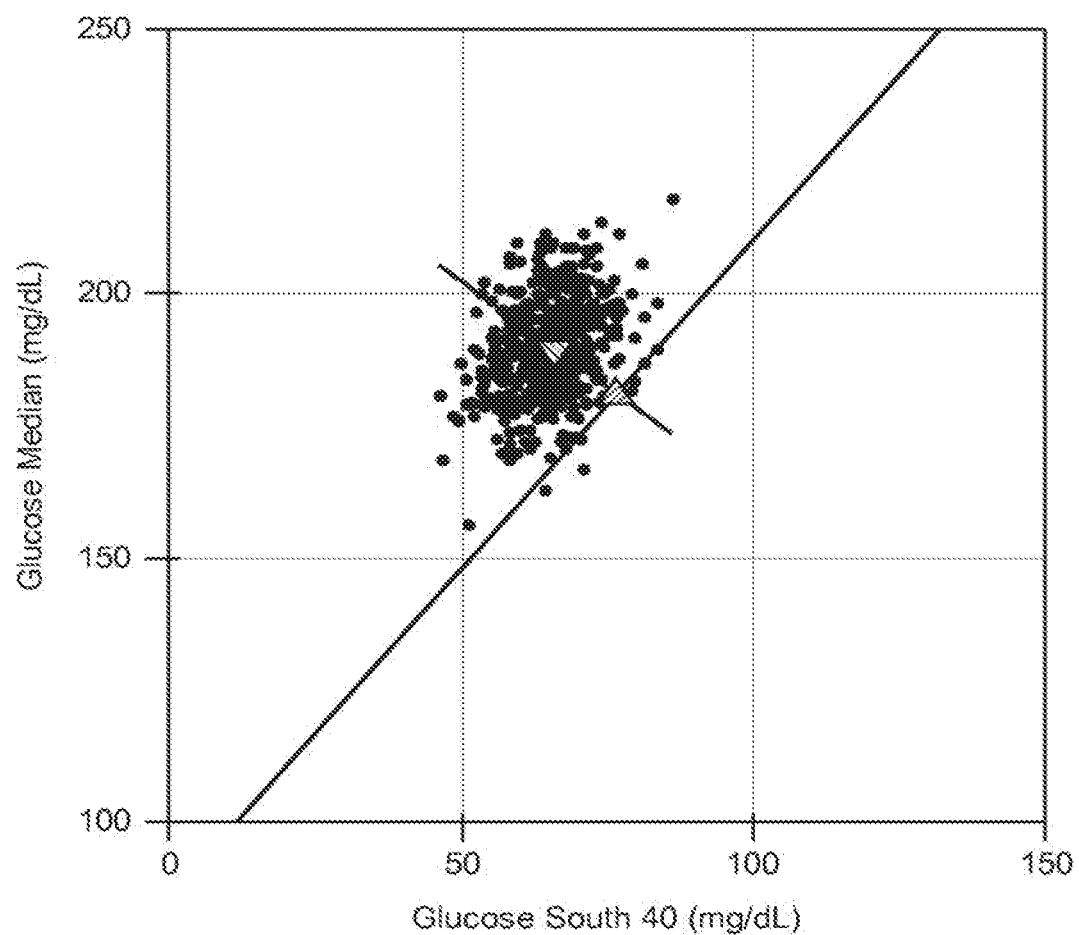
FIG. 46 illustrates the data shown in FIG. 41 with a line drawn parallel to the border of the Hypo Risk Zone such that only 5% of the bootstrap points are below the line, according to certain embodiments.

In some instances, however, a more conservative position may be desired. For example, it may be determined that the probability that the patient is in the Hypo Risk Zone should not be more than a specific percentage (e.g., 5%). Accordingly, a line may be drawn parallel to the border of the Hypo Risk Zone such that only that particular percentage (e.g., 5%) of the bootstrap points are below the line. For example, FIG. 46 illustrates the data shown in FIG. 45 with a line drawn parallel to the border of the Hypo Risk Zone such that only 5% of the bootstrap points are below the line. The line is shown extending from the bottom left of the figure to the top right of the figure. Furthermore, a second line perpendicular to this line and passing through the sample point may be used to define a Treatment Recommendation Point (TRP), as shown in FIG. 46. The intersection of these two lines defines the Treatment Recommendation Point (TRP) represented by the second triangle positioned at the intersection of the two lines. The TRP may then be moved by modifying the patient's treatment to the border of the Hypo Risk Zone to provide the 5% probability. It should be noted that 5% is an example, and any percentage may be used in other embodiments.

Figure 47:
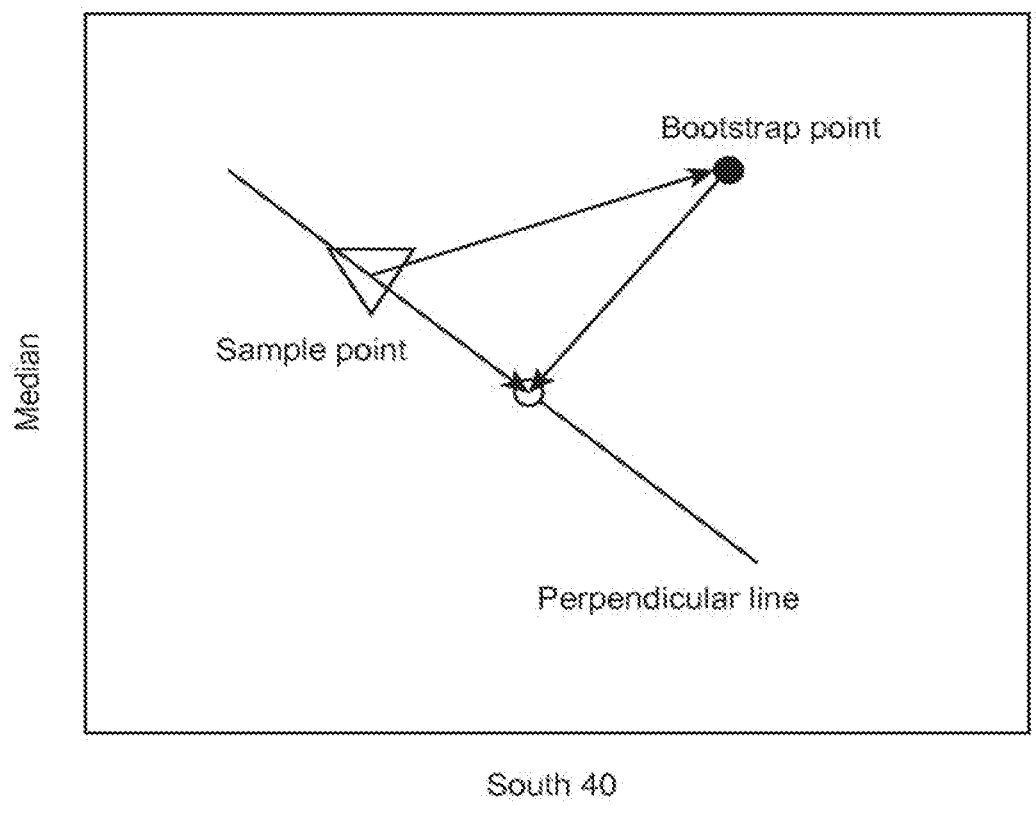
FIG. 47 illustrates a projection of one bootstrap point along a line perpendicular to the lines of constant hypoglycemia rate on a control grid, according to certain embodiments.

In certain embodiments, the TRP location is defined using projections of each bootstrap point. For example, defining the TRP location may comprise finding the projection of each bootstrap point along the perpendicular line pointing towards the Hypo Risk Zone. This may done, for example, by taking the dot product of each bootstrap point with the perpendicular line. FIG. 47 illustrates a projection of one bootstrap point along a line perpendicular to the lines of constant hypoglycemia rate on a control grid, according to certain embodiments. The sample point is shown as a triangle with the perpendicular line extending through the sample point. The bootstrap point is shown as the circular dot off to the right of the sample point, and its projected value on the perpendicular line is also shown (as the circular dot illustrated on the perpendicular line).

Defining the TRP location may also comprise determining a one-sided confidence limit of the resulting projected values. While various one-sided confidence limits may be used, a one-side confidence limit of 95% has been described for the given example. In certain embodiments, the confidence limit is determined by counting points. For example, the 95th percentile of the projected values may be determined Bootstrap-derived confidence limits may be undependable when sample sizes are small, and thus a more reliable method may be used. For example, in certain embodiments, the Bias Corrected and Accelerated method is used. Additional details regarding this method may be found in the article, "A Practical Introduction to the Bootstrap Using the SAS System", by N. Barker (SAS Conference Proceedings, Phuse 2005, paper PK02), the entirety of which is incorporated herein by reference.

For example, for the Bias Corrected and Accelerated method, the bias to be corrected is the difference between the sample point and the median of the bootstrap projected values. The bias correction may be represented by:

$$x_0 = \Phi^{-1}\left(\frac{\text{number of projected values} < \text{sample value}}{\text{number of projected values}}\right)$$

where $\Phi$ is the cumulative density of the normal probability distribution, and $\Phi-1$ is the inverse.

In some instances, additional calculations are needed for the acceleration part. For example, a jackknife is first performed on the sample as follows:
1. Leave out one data point from the sample.
2. Calculate south 40 and median from the reduced set.
3. Calculate the projected value, pi.
4. Repeat for every data point.

The jackknife yields as many estimates as there are sample values, and the mean value of estimates may be calculated, <p>. The acceleration factor may be defined as:

$$a = \frac{\sum_i (\langle p \rangle - p_i)^3}{6\left(\sum_i (\langle p \rangle - p_i)^2\right)^{3/2}}$$

The corrected percentile may be determined using the bias correction and the acceleration factor. For example, the following may be used to determine the corrected percentile:

$$\alpha_1 = 100\Phi\left(x_0 + \frac{x_0 + \Phi^{-1}(\alpha/100)}{1 - a(x_0 + \Phi^{-1}(\alpha/100))}\right)$$

where $\alpha$ is the desired percentile (e.g., 95).

Figure 48:
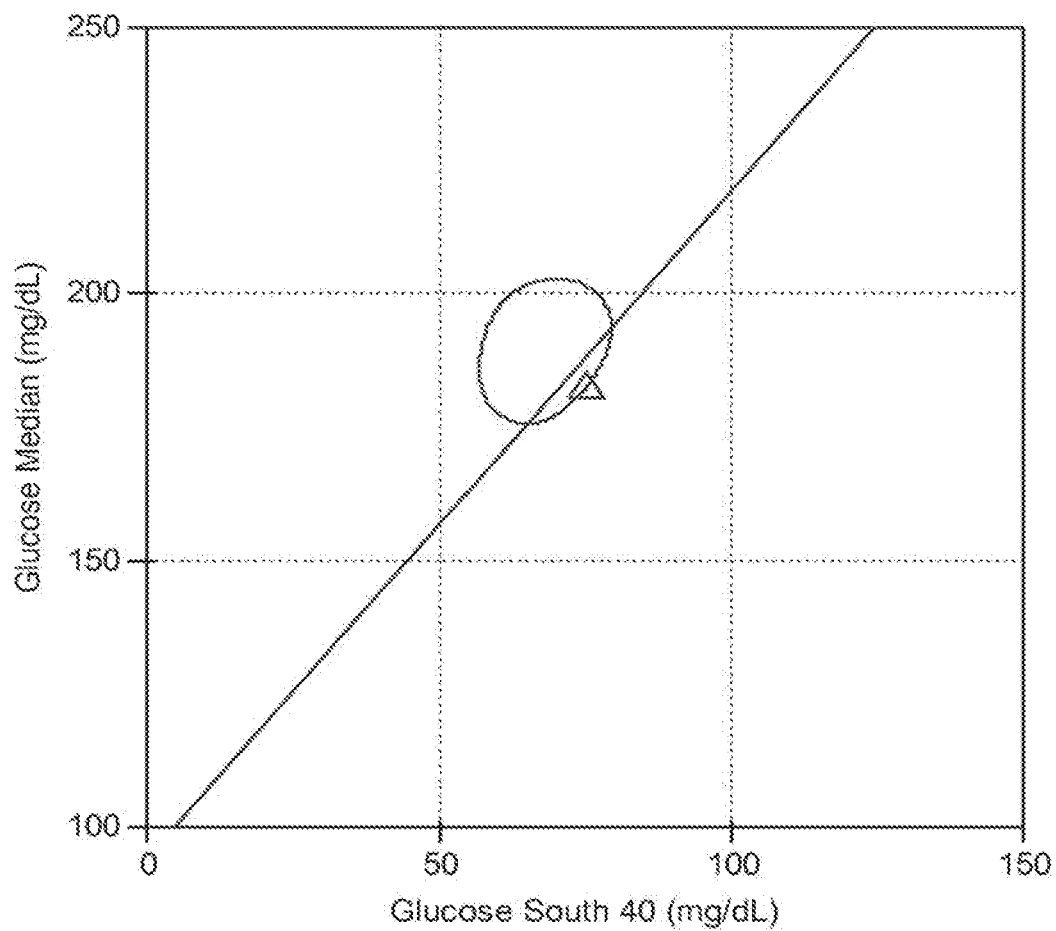
FIG. 48 illustrates a boundary line of a bootstrap cloud that was calculated using confidence limits, according to certain embodiments.

In some instances, confidence limits may be used to calculate a boundary line or "bubble" that gives an indication of the size of the bootstrap cloud. For example, FIG. 48 illustrates a boundary line of a bootstrap cloud that was calculated using confidence limits, according to certain embodiments. The boundary line of the bootstrap cloud is shown along with the TRP (shown as a triangle) and Hypo Risk Zone border line. In this way, the boundary line of the bootstrap cloud may be used for display instead of the points themselves.

Each point on the boundary line of the bootstrap cloud is found in the same way as the TRP value, for example. The direction of the line drawn through the sample point varies, and the resulting polygon is smoothed.

Figure 49:
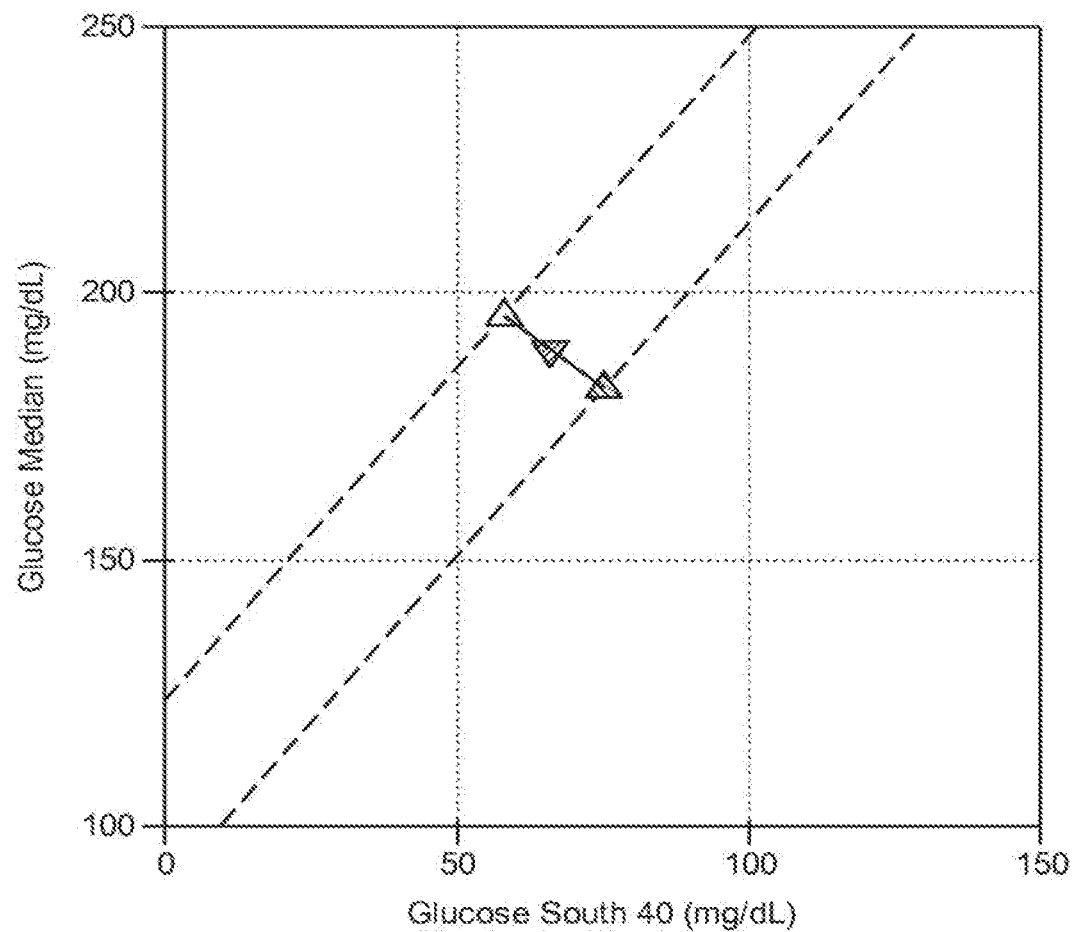
FIG. 49 illustrates a control grid showing a sample point, TRP, and an anti-TRP value, according to certain embodiments.

In some instances, confidence limits may be used to show the extent of the estimate uncertainty along the direction of hypo risk. For example, the TRP and the symmetric point on the other side of the sample point (also referred to herein as an "anti-TRP point") may be calculated. FIG. 49 illustrates a control grid showing a sample point, TRP, and an anti-TRP value, according to certain embodiments. The sample point is the middle triangle shown in the figure, and the TRP is the triangle at the 95th percentile along the dashed perpendicular line below and to the right of the middle triangle. The "anti-TRP" is thus the triangle at the 5th percentile along the dashed perpendicular line above and to the left of the middle triangle.

The distance between the two dashed perpendicular lines is the 90% two-sided confidence interval of the control grid estimate in the direction where the hypo rate is varying most quickly. This may be used, for example, to advocate for larger or smaller sample sizes, because larger samples produce smaller confidence intervals. For instance, it may be used in-house as a figure of merit to evaluate various testing schedules.

Figure 50:
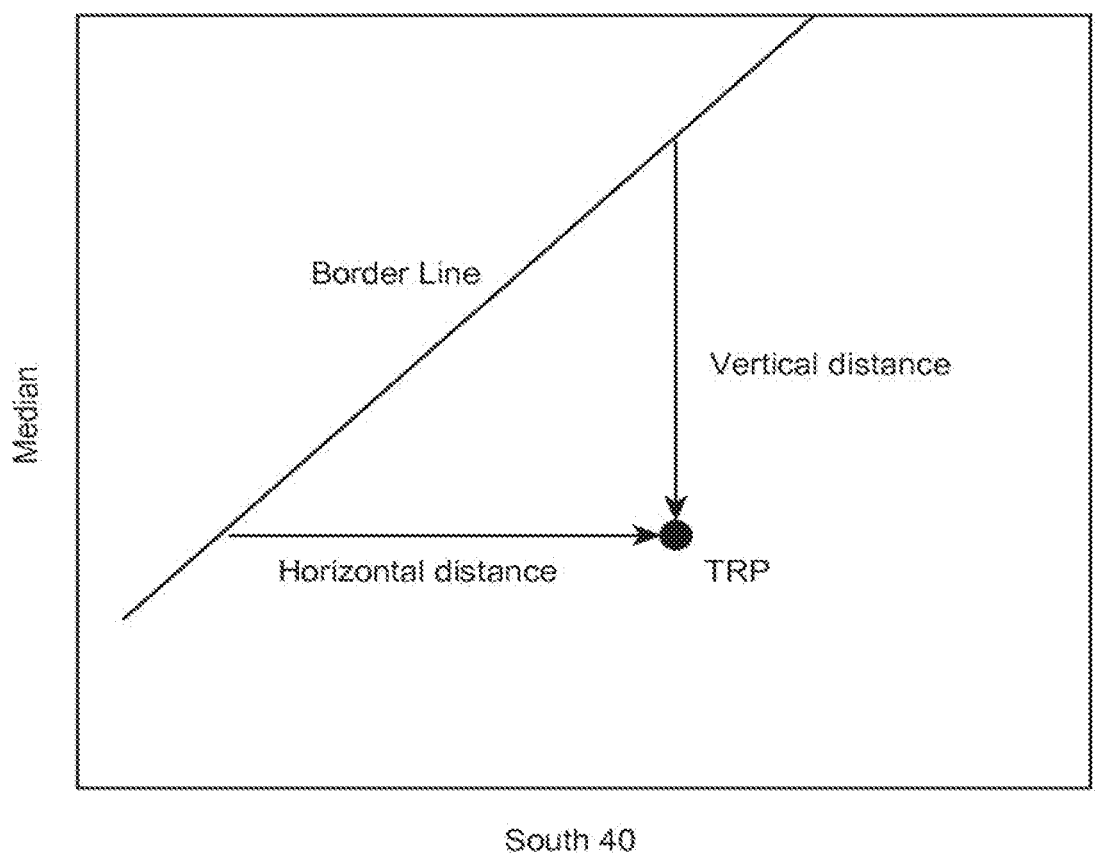
FIG. 50 illustrates the vertical and horizontal distances from a Hypo Risk Zone border line to a TRP point on a control grid, according to certain embodiments.

In some aspects, treatment may be guided when the relationship between the TRP and control grid zones is known. For example, the vertical and horizontal distances of the TRP from the Hypo Risk Zone boundary may be calculated. FIG. 50, illustrates the vertical and horizontal distances from a Hypo Risk Zone border line to a TRP point on a control grid, according to certain embodiments.

Positive and negative distance may be defined—e.g., distances may be defined as positive if the TRP point is above or to the left of the border line. In this way, the signs of the distances determine which zone the TRP is in, and the magnitudes may be used to guide the treatment changes. For example, if the vertical distance of the TRP to the Hypo Risk Zone border is −50 mg/dl, then the patient is in the Hypo Risk Zone. The doctor might decide that the easiest way to leave the zone is to move vertically upwards by 50 mg/dl, using the patient's insulin sensitivity to calculate the decrease in basal dose.

The perpendicular distance from the TRP to the border (shortest distance) may be derived by:

$$d_\perp = \frac{|vh|}{\sqrt{v^2 + h^2}}$$

where v is the vertical distance, and h is the horizontal distance. This can be seen by calculating the area of the triangle using the vertical and horizontal distances, and by calculating again using the perpendicular distance and the hypotenuse.

It should be appreciated that in some instances, one or more steps of the method described above may vary—e.g., one or more steps omitted, one or more steps combined, one or more steps performed in an a different order, one step performed in multiple steps, etc.

Determination of Appropriate Glucose Testing Schedule Based on Patient's Glucose Control Level and Clinical Risk In some aspects, there is provided a process for determining an appropriate glucose testing schedule based on a patient's glucose control level and clinical risk.

A patient's state of glucose control can be assessed in terms of 2 simple metrics. The first relates to the ability to maintain a desirable glucose level on average. The second relates to the ability to minimize the glucose excursion in the presence of meals and other factors. As described above, one method to graphically present these two metrics comprises the median glucose as the first metric, and the difference between the median and the 10th percentile glucose as the second. This graphical representation, called glucose control grid or chart. In the absence of high density data, such as from a continuous glucose monitoring (CGM) system, a glucose testing schedule may be used to collect the data.

In addition to the patient's state of glucose control, other clinically relevant information can be provided to enhance one's understanding of the impact of a planned treatment on the patient's various clinical states.

In some aspects of the present disclosure, there is provided a method wherein the appropriate testing schedule is a function of an a priori (e.g. population-based) uncertainty of various testing schedules and the relevant clinical risk being reviewed for each patient, as a reflection of the patient's state of glucose control.

As described above, a glucose control grid may be used to provide a snapshot of a patient's glucose control. The snapshot represents the multitudes of blood glucose (BG) data from self monitoring BG (SMBG) fingerstick readings and/or CGM system recordings over the course of days or weeks in between visits to the patient's health care provider (HCP), into a single point in the chart. In the case of SMBG as the sole data source, the patient needs to follow a pre-determined testing schedule.

Figure 51:
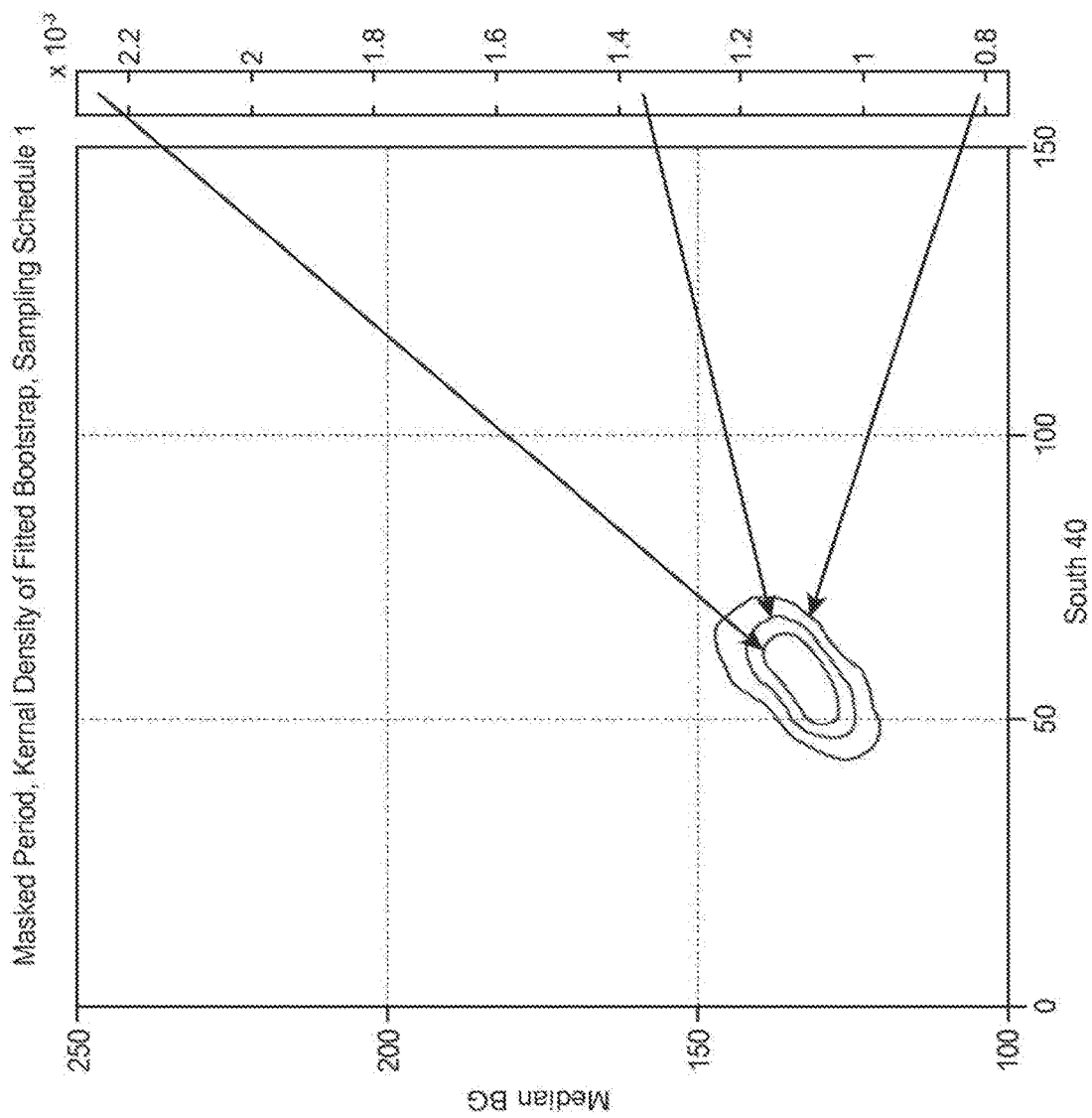
FIG. 51 illustrates contour plots of a probability distribution function of a patient's state of glucose control, according to certain embodiments.

Since the testing schedule may only sample glucose values and may not capture all the essential nature of a patient's state of glucose control, the uncertainty surrounding the single point estimate as presented in the glucose control chart depends on the testing schedule. FIG. 51 illustrates contour plots of a probability distribution function of a patient's state of glucose control, according to certain embodiments. For example, the distribution may be obtained from a patient performing a prescribed testing schedule over 14 days, and then using the bootstrap method to obtain 400 more estimates. This set of 400 glucose control grid data points is then used to create a probability distribution function. In the embodiment shown in FIG. 51, the 25%, 50%, and 75% contour heights are displayed. In this way, the uncertainty level of the patient's estimated glucose control level is represented.

Figure 52:
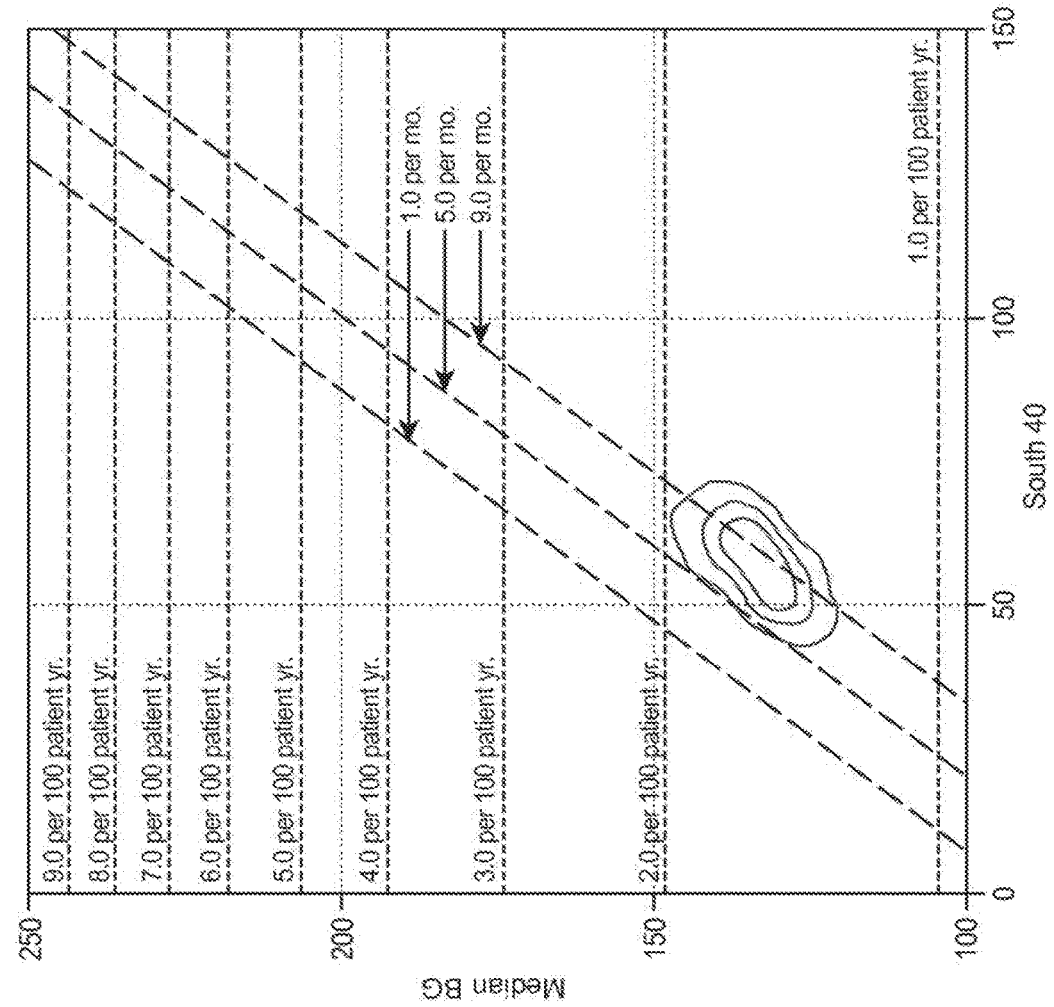
FIG. 52 shows the same distribution from the same patient shown in FIG. 47, in the context of two different clinical risks, namely the risk of retinopathy (horizontal lines) and risk of severe hypoglycemia (diagonal lines), according to certain embodiments.

In some aspects, different SMBG testing schedules may be implemented. For example, depending on the level of glucose control and the relevant clinical risk being focused on, different SMBG testing schedules that focus on different times of the day, different times relative to events such as meals and exercise, and testing frequency, may be needed. FIG. 52 shows the same distribution from the same patient shown in FIG. 51, in the context of two different clinical risks, namely the risk of retinopathy (horizontal lines) and risk of severe hypoglycemia (diagonal lines), according to certain embodiments. For example, the control grid shows the constant lines for 1 occurrence per month, 5 occurrences per month, and 9 occurrences per month. If the difference between five hypos per month and nine hypos per month is clinically relevant, then given the patient's current state of glucose control, the prescribed testing schedule is marginally able to distinguish a clinically meaningful change in severe hypoglycemia risk. This is because the extent of the contour lines is comparable to the distance between very different amounts of hypoglycemic risk. Assuming there is no large clinical difference between the 1% and 2% retinopathy lines, the testing schedule is sufficient to distinguish a clinically meaningful change in risk of retinopathy. Since the contour line span is significantly smaller than the gap between the nearest two retinopathy risk lines, the testing schedule is adequate to measure the patient's level of retinopathy risk.

Figure 53:
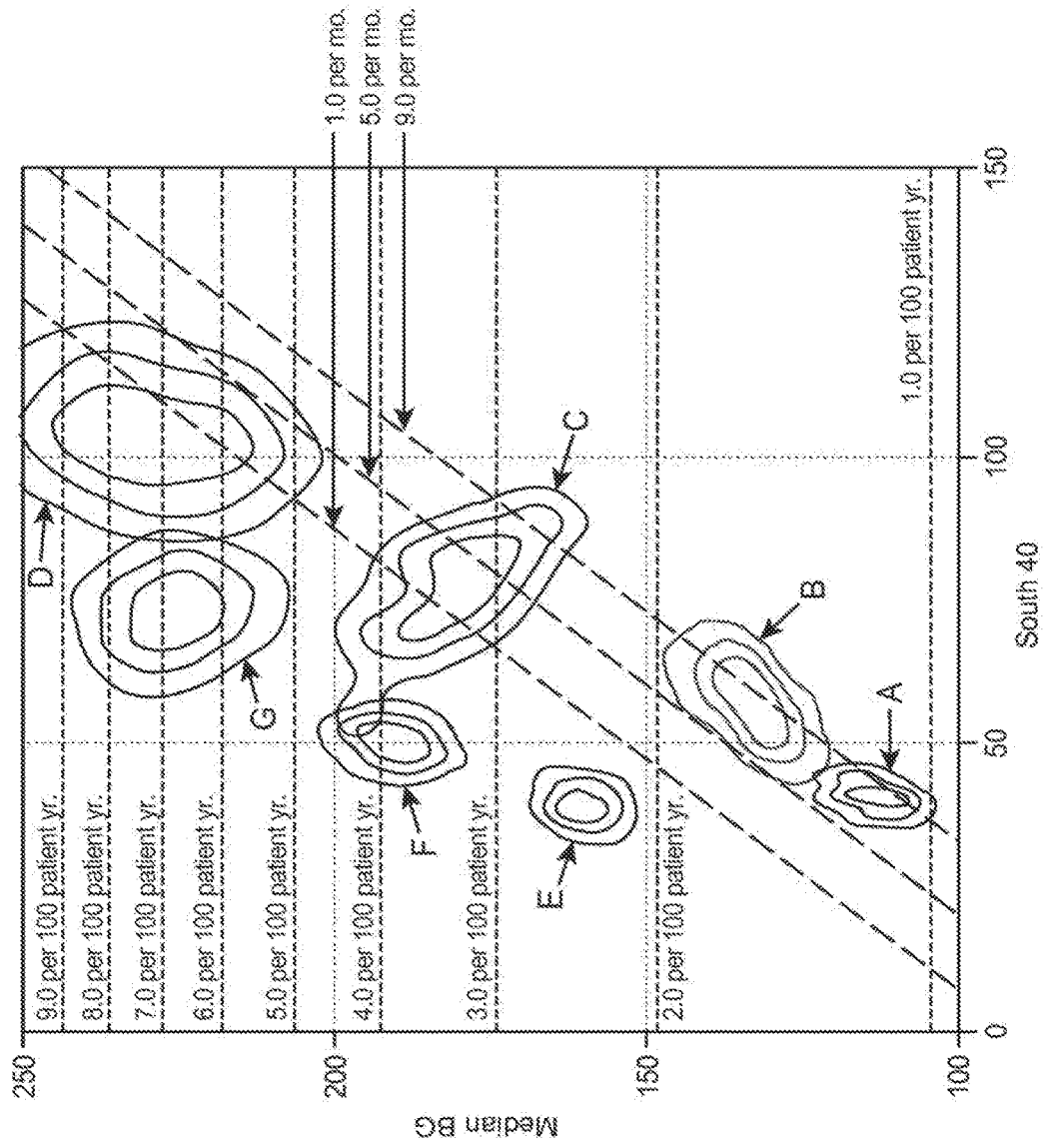
FIG. 53 illustrates contour lines for 6 additional patients plotted on the same control grid, according to certain embodiments.

The testing schedule used for the illustration in FIG. 52 may or may not be adequate in assessing different clinical risks for the same patient. This was already shown by the fact that the width of the contour lines along the different clinical risk gradient lines; risk of severe hypoglycemia and risk of retinopathy; are not the same. Similarly, the testing schedule used for the illustration in FIG. 52 may or may not be adequate in assessing the same clinical risks for a different patient, or the same patient with a significantly altered level of glucose control. FIG. 53 illustrates contour lines for 6 additional patients plotted on the same control grid, according to certain embodiments. Each set of contour lines A, B, C, D, E, F, and G represent the contour lines for one of the seven patients.

Note that as the patient's glucose variability increases (as represented by a larger x-axis value), and as the patient's propensity for high BG (blood glucose) value increases (as represented by a larger y-axis value), the same testing schedule generates different uncertainty levels as indicated by the different contour line size and shapes. For example, it may not possible to say anything definite about the patient C's risk of hypoglycemia, as the uncertainty contours span a range from less than one occurrence per month to more than nine occurrences per month. This is important because either extreme can trigger different sequences of treatment priorities. For example, the former would put the patient's high mean glucose as the immediate focus for improvement, while the latter could result in the temporary reduction of glucose lowering medications to reduce the acute mortality risk associated with severe hypoglycemia.

Figure 54:
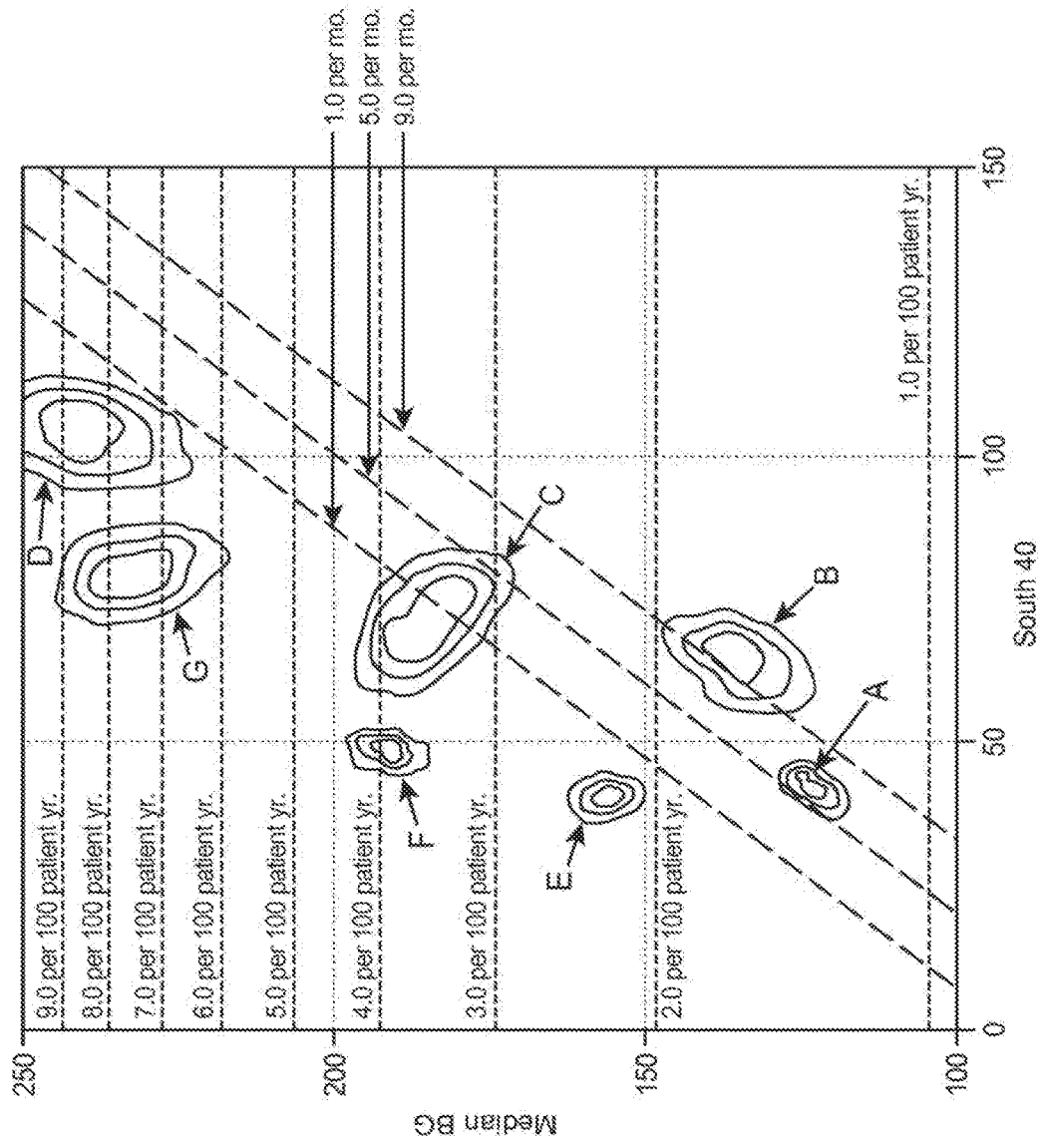
FIG. 54 illustrates the contour lines generated from a relatively stringent testing schedule on the same 7 patients as shown in FIG. 48, according to certain embodiments.

When a more stringent testing schedule is adopted, for example, the uncertainty of the patient's glucose control generally decreases regardless of the level of glucose control (e.g., regardless of where the point is in the glucose control chart). FIG. 54 illustrates the contour lines generated from a relatively stringent testing schedule on the same 7 patients as shown in FIG. 52, according to certain embodiments. Compared to FIG. 53, the uncertainty levels are markedly decreased, particularly in areas of poor glucose control. For patients A and E, for example, the more stringent testing schedule may not offer any significantly better insight with respect to the two clinical risks discussed as examples. However, for patient F, who achieves low glucose variability while maintaining high mean glucose levels, the more stringent testing schedule may help differentiate the patient's risk of retinopathy when compared to the next or previous visit (not shown in the plots). Furthermore, patient D's risk of hypoglycemia has been clarified.

In some aspects, there is provided a method to generate uncertainty levels of a patient's state of glucose control estimate as a function of specific SMBG testing schedules, a given clinical risk, and the two axis of the glucose control chart.

In certain embodiments, different SMBG testing schedules are collected, wherein for each schedule, uncertainty levels are computed a priori from population data.

In certain embodiments, the population data is comprised of CGM values or SMBG data taken at a relatively frequent interval that approaches that of a CGM. For example, in some instances, the frequency interval may range from once every 15 minutes of faster. In other instances, less frequent frequency intervals may be used.

In certain embodiments, the population data is obtained from human studies wearing CGM systems.

In certain embodiments, the population data is obtained from in-silico human models representing a wide range of demographics, state of diabetes, and various other physiological parameters.

In certain embodiments, the uncertainty levels from the population data is projected along the gradient of a particular clinical risk. This may result, for example, in a map of uncertainty levels for a given SMBG testing schedule and clinical risk as a function of the two axis of the glucose control chart.

Figure 55:
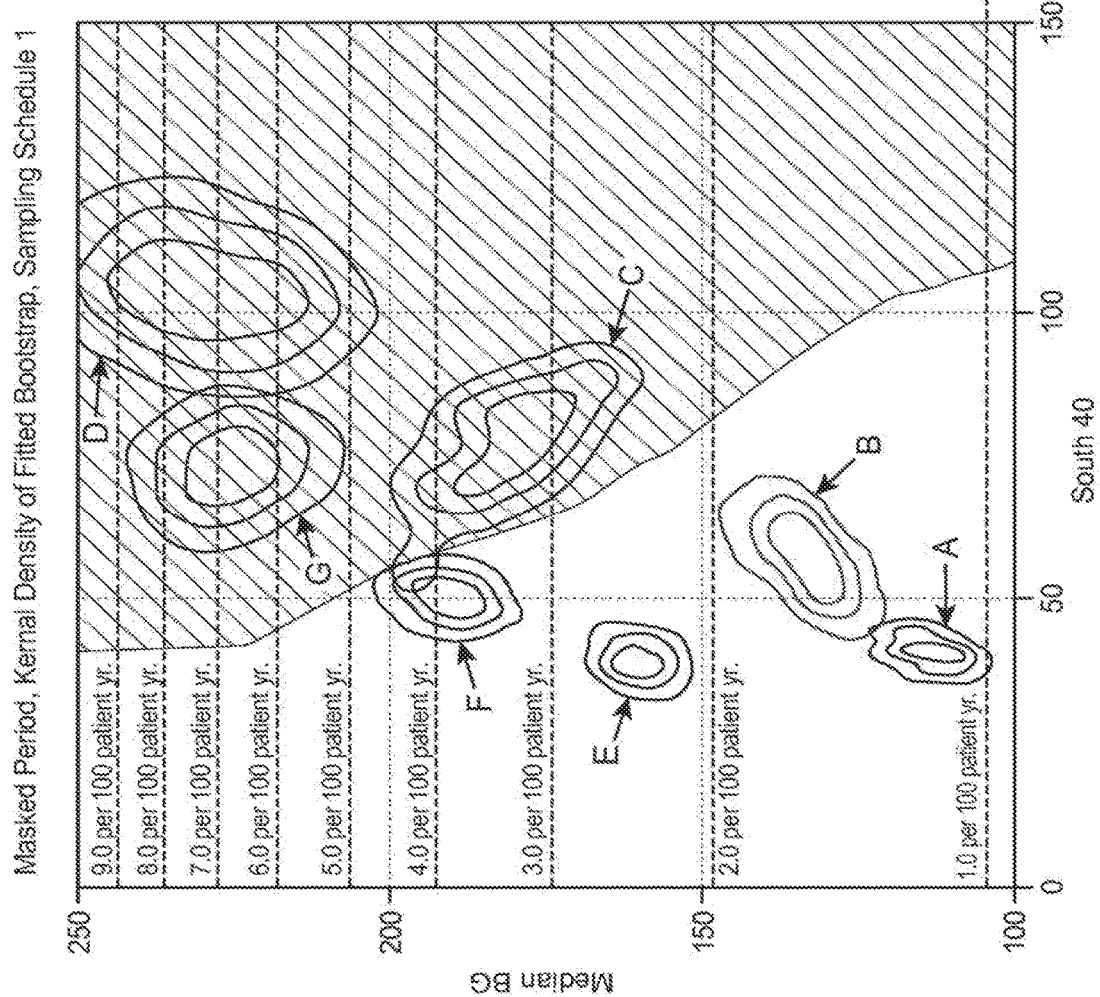
FIG. 55 illustrates the determination of areas where a given testing schedule is adequate vs. inadequate in detecting a clinically meaningful change in risk of retinopathy, according to certain embodiments.

In certain embodiments, adequate and inadequate areas in the glucose control chart are identified for each combination of SMBG testing schedule and clinical risk being considered. For example, an area may be considered adequate if it has a sufficiently small uncertainty level relative to a clinically relevant gradient change. Otherwise, it is considered to be inadequate. For example, FIG. 55 illustrates the determination of areas where a given testing schedule is adequate vs. inadequate in detecting a clinically meaningful change in risk of retinopathy, according to certain embodiments. For FIG. 55, a testing schedule of 4 times a day at 7 am, 11 am, 5 pm, and 10 pm was used. It should be appreciated that different testing schedules may be implemented—e.g., that include any number of additional times in the day.

In FIG. 55, The shaded area corresponds to areas where the particular testing schedule is not adequate in detecting a clinically meaningful change in the risk of retinopathy, because the spread of the estimates along the direction of clinical change is much larger than the distance between local clinical risk lines. Thus, for example, it may be determined that a patient whose current state of glucose control puts their estimates in the inadequate space relative to the clinical risks being considered will need to follow a different testing schedule. Conversely, a patient whose glucose state is far from the boundary between inadequate and adequate region may be determined to be able to use a potentially less demanding testing schedule. It should be appreciated that different clinical risks (e.g. severe hypoglycemia, diabetic ketoacidosis, kidney failure, etc.) may result in different boundaries between adequate and inadequate areas for the same testing schedule.

In some aspects, there is provided a method to utilize the mapped uncertainty levels in the context of a specific set of clinical risks to provide a recommended SMBG testing schedule specific to each patient's latest state of glucose control.

In certain embodiments, given a patient's initial data under the particular SMBG testing schedule, the proper map described above (the map representing uncertainty levels of a patient's state of glucose control estimate as a function of specific SMBG testing schedules, a given clinical risk, and the two axis of the glucose control chart) is referenced to see if the patient's glucose control estimate falls within the adequate or inadequate region.

In certain embodiments, clinical risks being considered, a recommended SMBG testing schedule is offered that will not render the patient's testing efforts meaningless for the clinical aspect being focused on.

In certain embodiments, given the set of SMBG testing schedules that a patient can fall into the adequate range, and given the intended direction of the next treatment leading to the next follow-up visit, an SMBG testing schedule that puts the next predicted state of glucose control into an adequate range is considered, and one that is the least demanding may be offered to the patient. In this way, the least demanding schedule may be offered that will still allow for a useful determination of changes in clinical risk while keeping in mind that while a more demanding schedule may be ideal, it may practically be the exact opposite when a patient's concordance is too low.

Graphical Presentation of Clinical Impact on Patient's State of Glucose Control

In some aspects, there is provided a method for graphically representing clinical impact on a patient's state of glucose control.

In addition to the patient's state of glucose control, other clinically relevant information can be provided to enhance one's understanding of the impact of a planned treatment on the patient's various clinical state.

In some aspects, there is provided a method whereby clinically relevant states (e.g., long term cardiovascular risk, long term retinopathy risk, short term diabetic ketoacidosis risk, acute hypoglycemia risk, etc.) are adapted by performing transformations and mapping from population data. In this way, given a patient's state of glucose control, as shown in the glucose control chart, the various clinical risks may be identified, in order to provide relevancy in selecting a median glucose target.

Figure 56:
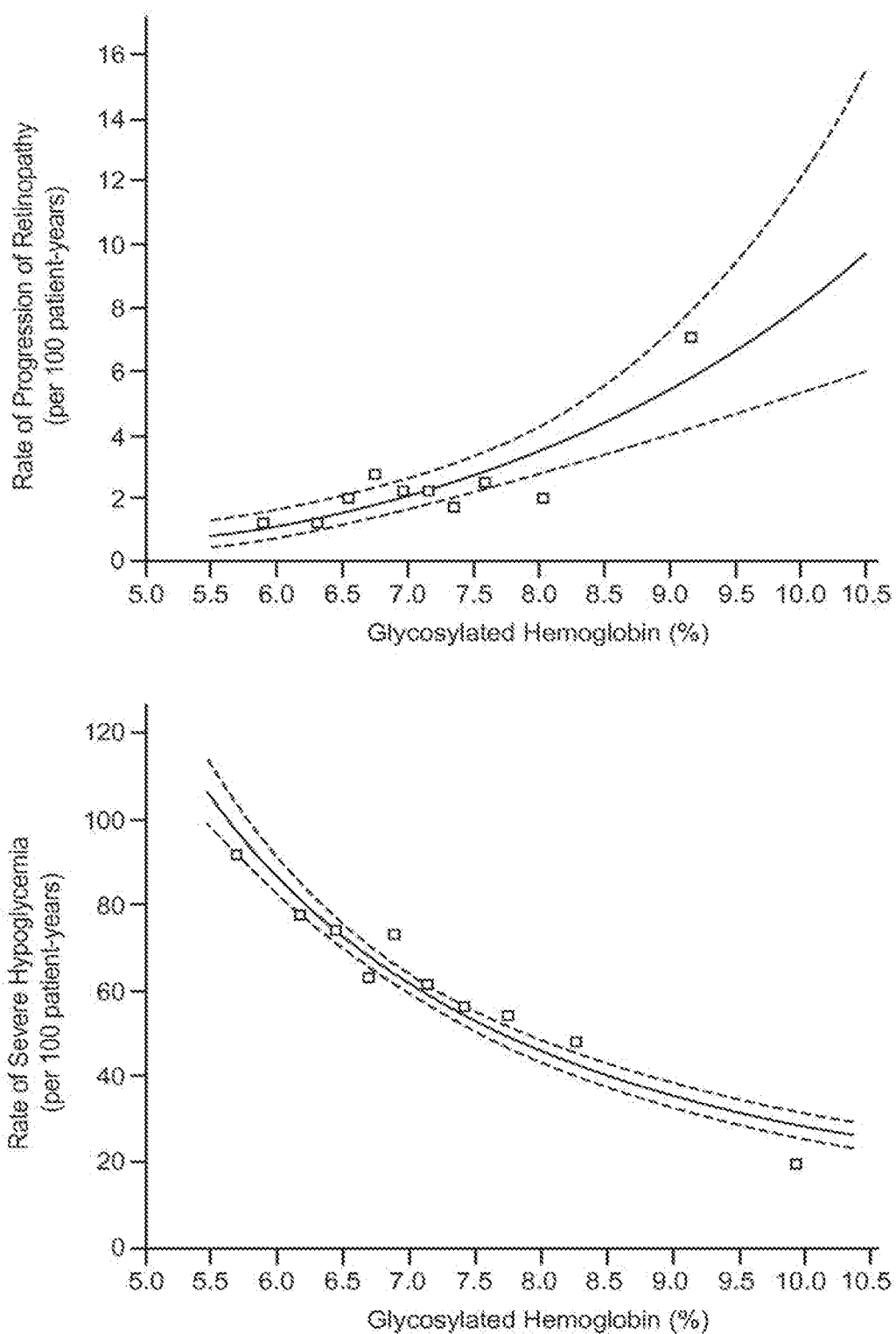
FIG. 56 illustrates the association between HbA1c and risk of retinopathy and HbA1c and risk of sever hypoglycemia.

Long-term complications may cause major morbidity and mortality in patients with insulin-dependent diabetes mellitus. Studies have established these clinical risks with measurable markers, where an association between long-term complications and HbA1c are often made. For example, associations between HbA1c and risk of progression of retinopathy, and between HbA1c and risk of severe hypoglycemia have been made—e.g., such as described in the article, "The Diabetes Control and Complications Trial Research Group, "The Effect of Intensive Treatment of Diabetes on Development and Progression of Long-Term Complications in Insulin-Dependent Diabetes Mellitus" (The New England Journal of Medicine, v329, n14, 1993), the entirety of which is incorporated herein by reference. FIG. 56 illustrates the association between HbA1c and risk of retinopathy and HbA1c and risk of sever hypoglycemia.

Focusing on the association between HbA1c and risk of retinopathy as an example, a connection may be made to the glucose control chart. For example, one method may use an association between estimated average glucose (eAG) and HbA1c. Using population data, a further association can be made between eAG and one or more axis of the glucose control chart. For example, an association may be made between eAG and the median glucose axis of the glucose control chart. Various methods can be used to obtain these associations. For example, the association between eAG and median glucose may be made by computing the eAG and median glucose values of a population of patients, and then using these pairs to fit a curve by Least Squares Error fit or other curve fitting methods. In another embodiment, a non parametric approach may be taken, where a table is generated that maps a certain range of eAG to a range of median glucose, and vice versa.

Figure 57:
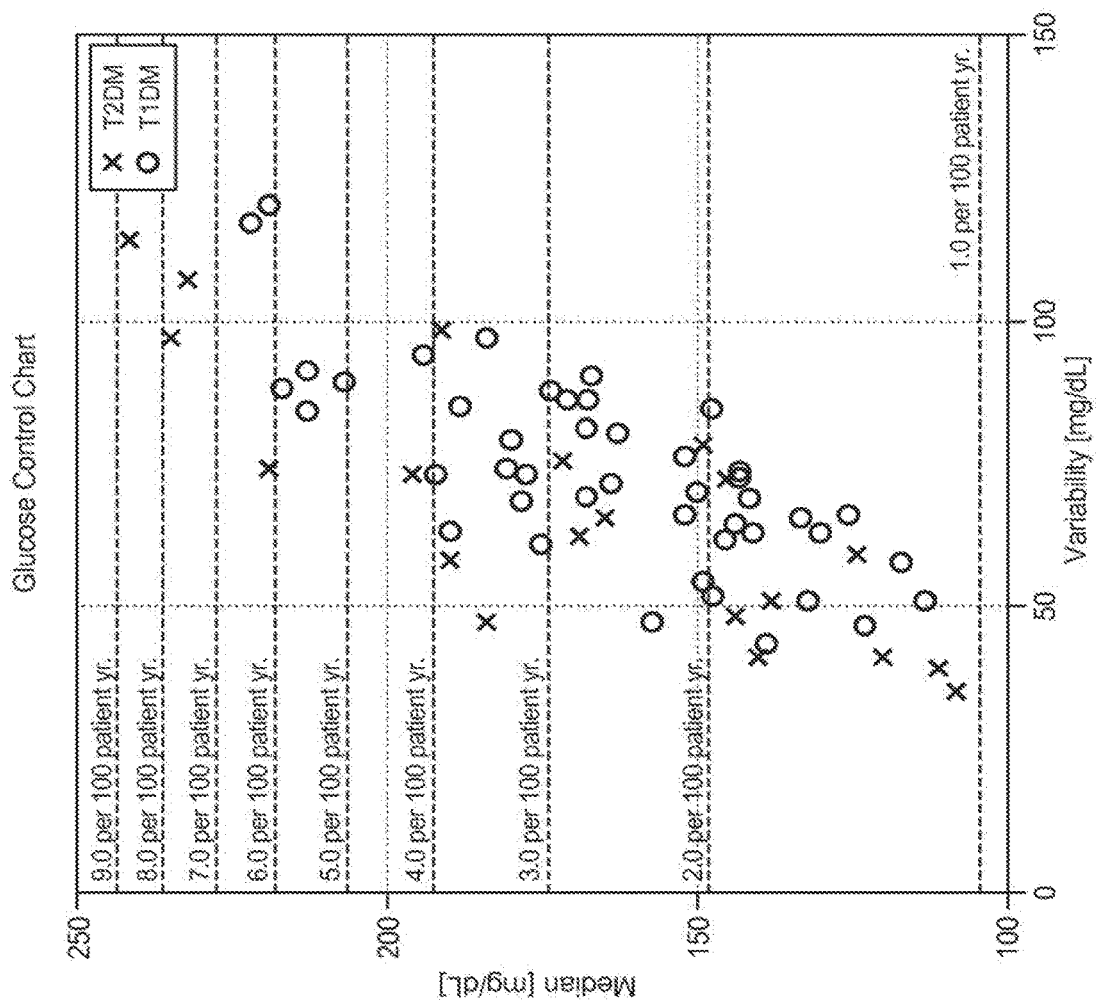
FIG. 57 illustrates a mapping a clinical risk, namely risk of retinopathy, onto a glucose control chart, according to certain embodiments.

FIG. 57 illustrates a mapping a clinical risk, namely risk of retinopathy, onto a glucose control chart, according to certain embodiments. The graphical overlay of retinopathy risk may be added onto the glucose control chart, as shown in FIG. 57, by, for example: 1) using a Least Squares Error fit of a line may be used to define the correlation between median glucose and eAG; 2) using a correlation between eAG and HbA1c—e.g., using a previously published correlation between eAG and HbA1c, such as described in the article by Nathan et al., entitled "Translating the A1c Assay Into Estimated Average Glucose Values" (Diabetes Care, v.31, n8, 2008), the entirety of which is incorporated herein by reference; and then 3) determining the logarithmic correlation between HbA1c and risk of retinopathy.

In FIG. 57, each patient's state of glucose control, as represented by a single icon (each cross indicates a Type 2 Diabetes Mellitus patient, each circle indicates a Type 1 Diabetes Mellitus patient), can be viewed directly in terms of their clinical risk. In particular, the figure shows each patient's retinopathy risk. In addition, given an expected change in median glucose and glucose variability, an anticipated change in clinical risk may be estimated.

Figure 58:
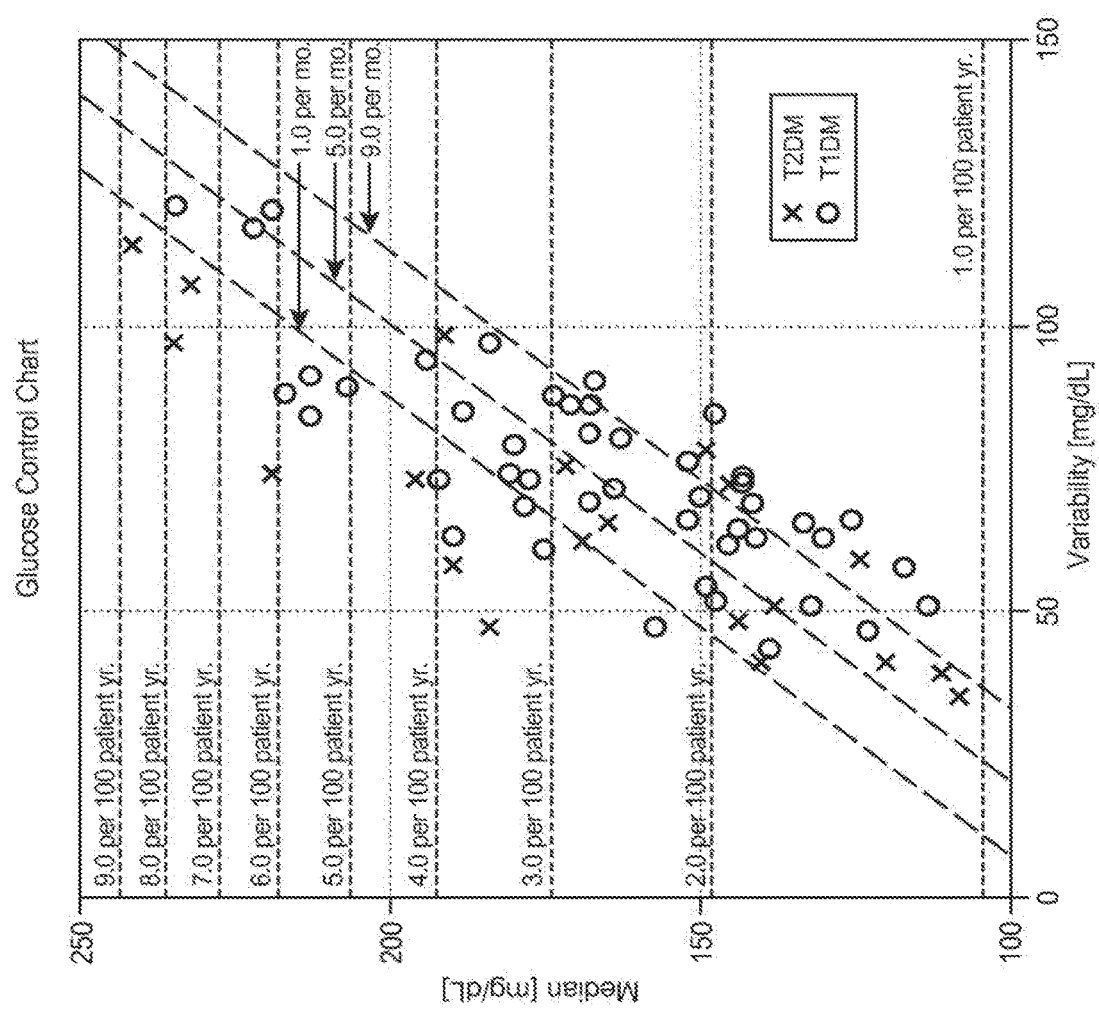
FIG. 58 illustrates multiple clinical risks—clinical risk of retinopathy and acute risk of hypoglycemia—overlaid on glucose control chart containing data for two separate diabetic sub-populations, according to certain embodiments.

FIG. 58 illustrates multiple clinical risks—clinical risk of retinopathy and acute risk of hypoglycemia—overlaid on glucose control chart, according to certain embodiments. The control grid also shows the constant lines for the number of occurrences of hypoglycemia per time period (e.g., 1, 5, and 9 occurrences per month).

Figure 59:
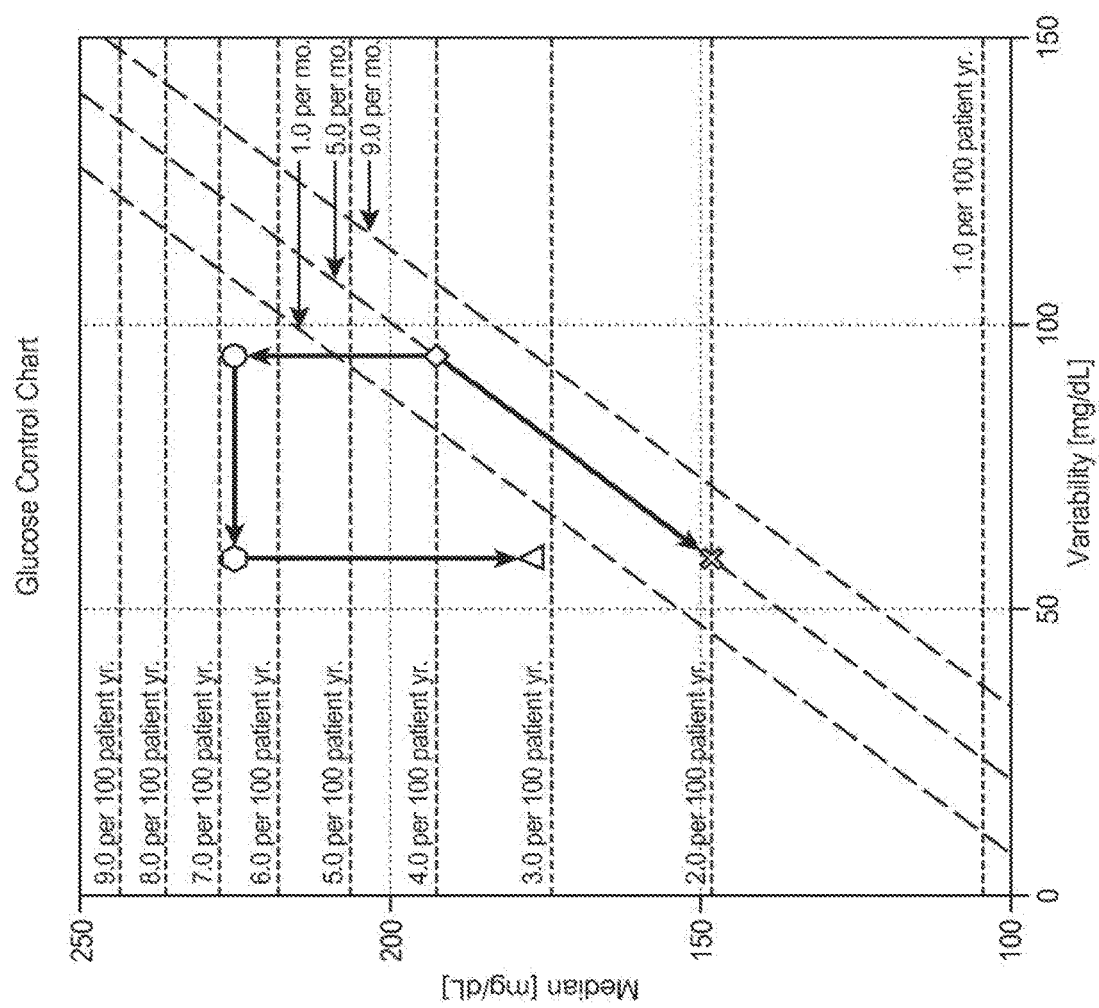
FIG. 59 illustrates an example of the progression of a patient's state of glucose control relative to two clinical risks, according to certain embodiments.

FIG. 59 illustrates an example of a patient's state of glucose control relative to two clinical risks, according to certain embodiments. The two risks are risk of retinopathy and hypoglycemia. If, for example, a patient's latest state of glucose control is represented by the diamond icon in FIG. 59, the patient has a 4% chance of suffering from retinopathy, and 5 severe hypoglycemic events per month, if no change is made on the patient's state of glucose control. The circle and cross icons represent, for example, two medical options that are available. While the second option offers a 50% reduction in retinopathy risk, the acute risk of hypoglycemia remains practically unchanged. The first option on the other hand, allows the patient to resolve the immediate issue of hypoglycemia risk, although at the cost of an increased risk of retinopathy. Since retinopathy is a longer term risk, this may be a more rational choice in some instances, as the subsequent visit to the patient's health care provider may then focus on further reducing glucose variability (as shown, for example, by the pentagon icon in FIG. 59) before attempting to reduce the patient's overall glucose (as represented by the triangle icon in FIG. 59)

In some aspects, a method is provided to overly various clinical risks onto the glucose control chart in order to provide context of a patient's state of glucose control relative to various clinical risks. For example, in certain embodiments, risk of retinopathy and hypoglycemia are used.

In some aspects, a method is provided to compare the relative clinical benefits of modifying one or both aspects of a patient's glucose control given a patient's current state of glucose control and given the available treatment options.

In some aspects, a method is provided to associate clinical risks to one or more axis of the glucose control chart. For example risk of retinopathy may be associated to a glucose control chart by one of the following sequence of maps: median glucose to eAG, eAG to HbA1c, and HbA1c to risk of retinopathy. It should be appreciated that different paths may be needed in different circumstances depending on data availability from clinical studies.

In some aspects, a method is provided to allow doctors or other health care professionals to recommend treatment to patients. For example, the doctor may select an appropriate median glucose target from a range of possible targets by associating these targets with a) long term and short term complications, and b) an achievable near-term goal based on where the patient metrics currently fall on the grid. The combination of the target and the grid provides the clinician with a clinical perspective of how to modify therapy (e.g., by addressing the median or addressing variability or both) in relationship to the target. In certain embodiments, for example, the method may comprise 1) processing glucose data to determine the median and variability metrics, 2) plotting the point (or uncertainty bubble) representing these metrics on the grid, 3) displaying the grid with various targets related to complications (e.g., this may be done with multiple tabbed displays where each tab is related to a different complication), 4) providing a means for the doctor to select a target (for instance, mouse clicking on the desired target), 5) displaying the grid with only the selected target, 6) generating treatment recommendations based on which grid zone the metric falls into.

Medication Titration Between Clinical Visits Using Glucose Median and Variability Algorithm In some aspects of the present disclosure, the methods and devices described above that map the glucose median and variability metric to treatment recommendations may be used to titrate medication, such as insulin, in a setting outside the standard clinical visit. For instance, in certain embodiments, algorithms for such methods may be implemented completely within the glucose measurement system, such as an SMBG meter, an "on-demand" CG meter or a CGM, where the outputs of the algorithm are titration instructions displayed periodically, e.g., once per week, on the device to the patient. The titration amounts may be preconfigured, or the algorithm could determine titration amounts based on preconfigured parameters, such as maximum titration amount, maximum total dose amount, and parameters common to bolus calculators, such as insulin sensitivity and carbohydrate ratio.

In another embodiment, the algorithms for methods described herein may be implemented partially within the glucose measurement device and partially within a remote software program accessible to clinicians (e.g, via a remote computer). The remote software program may provide, for example, titration recommendations to be approved by the clinician and then allow the clinician to remotely configure the glucose measurement device to display updated dosing instructions. The functionality may be divided between the device and the remote program a variety of ways. As an example, the device may upload data periodically to the remote software program, which contains the mapping algorithm and generates titration recommendation and other analysis to the clinician. The clinician may confirm the recommendation or otherwise alter the current titration and remotely configures the device with the new titration settings. In this way, the clinician is able to monitor patient titration. Remote data upload and configuration may be accomplished using any number of communication mechanisms, wired or unwired, known in the art.

Software Application for Communicatively Coupling an Analyte Monitoring Device with a Remote Server Via a Computer In some aspects, a software program is provided for transferring data from an analyte meter to a computer or other data processing device. For example, in certain embodiments, once loaded on the patient's computer or data processing device, the software application will activate whenever their meter is connected to the computer and will automatically upload the data from the meter to a remote server. In some instances, no user action may be required by the user for the automatic upload process. It should be appreciated that the source of this data from a blood glucose meter or any other type of analyte monitoring device.

Figure 60:
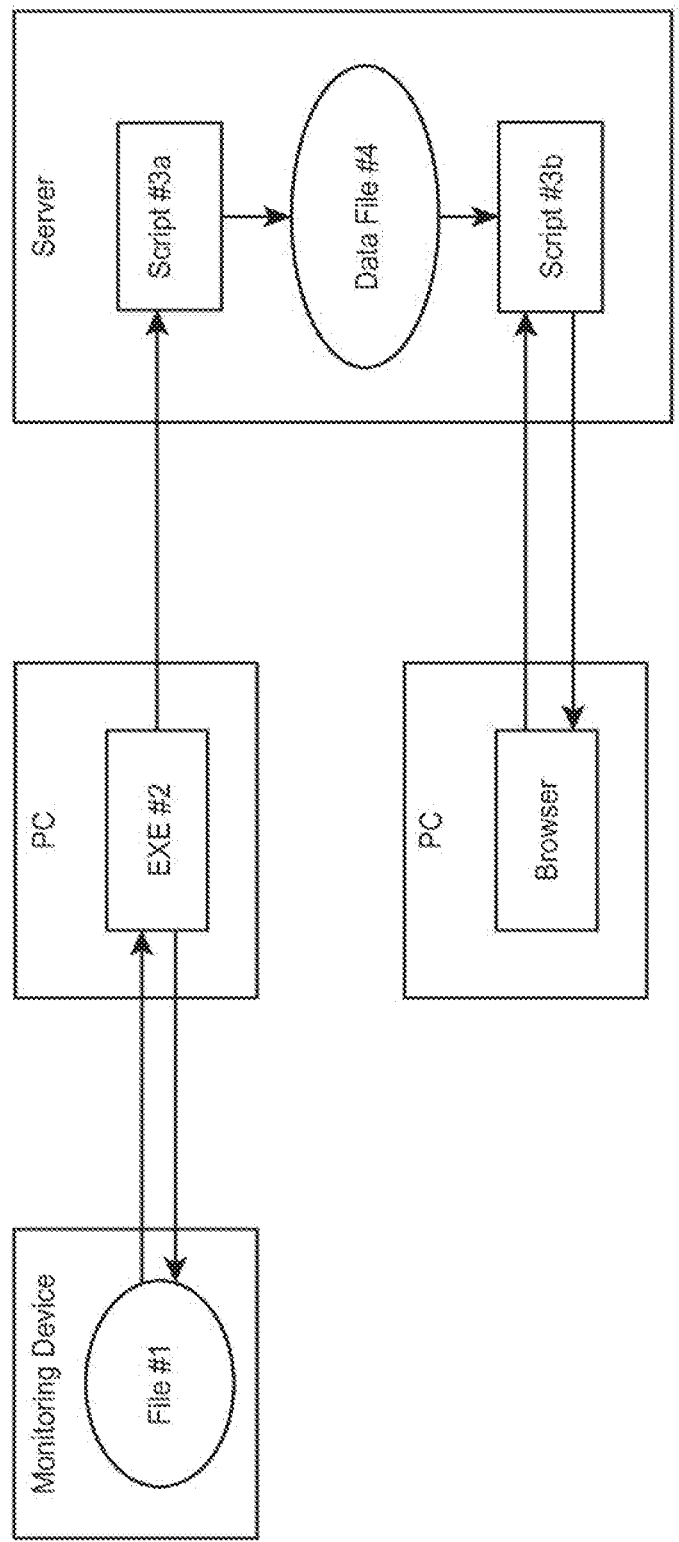
FIG. 60 illustrates an example block diagram for the software application for communicatively coupling the meter with the remote server via a computer, according to certain embodiments.

FIG. 60 illustrates an example block diagram for the software application for communicatively coupling an analyte monitoring device (e.g., a glucose meter) with the remote server via a computer, according to certain embodiments. In certain embodiments, two separate software programs are used—one program (#2) runs in the background on the patient's computer ("PC") and the other comprises scripts (#3a,#3b) running on a remote server (e.g., PERL scripts or other suitable scripts). The scripts may include, for example, a script for uploading data (#3a), a script for viewing data (#3b). The software running on the remote server may also include a data file (#4) on the remote server that accumulates uploaded data.

In certain embodiments, once the PC program is installed, it runs silently in background mode until the monitoring device is communicatively coupled to the computer (e.g., plugged into a USB port or wirelessly connected, for example). If the device is appropriate, the PC program invokes the remote server script #3a for uploading some or all of the data ("File #1") by for example making an HTTP request, which uploaded data is then stored on the remote server in the data file. For example, the upload script (#3a) is invoked via HTTP POST request from the program #2, wherein the data is sent via STDOUT and arrives via STDIN on the server side. For example, the data file (#4) is written by script #3a to a server directory protected by HTTP authentication. A browser user may then visit the URL for Script #3b and logs in via HTTP authentication to view the uploaded data. Script #3b reads the data file (#4), formats it into an HTML table, and generates a web page that is sent to the user's browser.

In some instances, the communicated data also includes other related information such as the BGM serial number and/or the MAC address of the PC which could be used to minimize the possibility that the BGM data gets associated with the wrong patient. It should also be appreciated, that in some instances, the software program may include a script for deleting the data from the monitoring device. For example, the computer program may invoke a script on the monitoring device to delete the data from the monitoring device after the data is uploaded.

Software Application for Configuring a Continuous Glucose Monitor (CGM)

In certain embodiments there is provided a CGM alarm configuration tool. CGM alarms include high and low threshold crossings and projected threshold crossing based on trend information. These alarms can be configured to be more or less sensitive based on the threshold values and the projection time. For instance, a projected low glucose alarm would occur more often if the threshold is set high and/or the projected time is long. This may be annoying for the patient. On the other hand, a high threshold and/or long projected time may also lead to better glucose management. So a trade-off can be made between better glucose management and usability (fewer annoying alarms).

This trade-off may not be easy for most CGM patients or their HCPs to understand. Provided herein is a software tool that can be used to inform patients and HCPs on how to best adjust alarm settings.

The software tool incorporates a glucose response simulation based on a glucose response model defined for that specific patient or defined for a population of patients. The simulation would be based on recorded inputs of prior glucose, meals, insulin injection and other recorded factors that may impact glucose response. Assuming that the patient would treat a high or low glucose alarm immediately or soon after occurrence, various alarm setting scenarios would be simulated and results (glucose control metrics and alarm occurrences) would be generated for each of these settings. The "treatments" associated with each scenario, such as eating and insulin injection, would be included as inputs to the simulation. The software would provide a "trade-off table" or plot of glucose control metrics and alarm metrics as a function of alarm settings. For example, the table may provide average glucose, hypoglycemia occurrences, and alarms per day versus combinations of low glucose threshold and projection time. The HCP may then discuss these results with the patient and decide on appropriate alarm settings. The software may also have a means to program the CGM with the selected settings.

In another embodiment, the software tool uses a non-parametric model that simulates the statistical characteristics of a patient's glucose variability. For instance, the spectral characteristics of the glucose response would be estimated from the patient's glucose data, using standard data analysis techniques, and a random simulation based on these characteristics would be generated for different alarm setting scenarios.

In another embodiment, the software tool creates a database of various actual glucose responses based on various alarm settings and patient glucose control characteristics. For each category of glucose response characteristic, a trade-off table is generated using associated data in the database. The patient's glucose response characteristic would be matched to the closest data set in the database, and the software would look up the associated trade-off table.

These features may be incorporated into any diabetes analysis software, into a stand-alone application, or into a stand-alone device (e.g., CGM device).

Software Application for Creating Therapy Recommendation Smart Reports

In certain embodiments, there is provided a method for creating therapy recommendation smart reports.

A common complaint from HCPs who treat people with diabetes is the time and involvement required to analyze retrospective data associated with the diabetic condition. Specifically, HCPs have favorite reports that they walk through to try to understand how well the patient is managing their diabetes and to determine necessary treatment adjustments. Data analysis software that detects adverse conditions and reports these conditions, and perhaps makes recommendations, has been disclosed. The condition would be reported by some means like a textual display listing the adverse conditions by priority. The data may be summarized on a standard report with for instance a modal day plot and key statistics. However, some HCPs like to look through various reports to get different perspectives of the data and the problem that has been detected.

Provided herein is an automated feature associated with data analysis that detects adverse conditions and makes recommendations. This feature is to pre-define one or more specific types of reports for each possible adverse condition and/or recommendation, and then when the analysis software detects this condition, to display the specific report(s) that best illustrates the problem. The advantage here is that HCPs will no longer need to take the time to drill down to the report they want for a specific condition (some HCPs may not even know what the best report is to illustrate a condition/recommendation). The optimum report type is generated automatically and displayed to the HCP. The report may illustrate the condition and demonstrate the expected effect from a recommended treatment adjustment.

For example, the software would detect that the patient almost always has low glucose in the morning prior to breakfast. Along with an indication displayed to the HCP of this condition, the software may also display a modal day graphic that shows the aggregate effect of being low in the morning—perhaps only the first half of the day is displayed. The plot may also highlight the portion where it is low and show the low target. Finally, the plot may also show an expected modal plot based on the recommendation which may be a reduction in the basal insulin dose, demonstrating how the recommendation would be executed to improve glucose management. The HCP would see this almost instantly after initiating the analysis and would not have to search for the appropriate plot or report.

Another example would be that the patient is occasionally very high after the dinner meal. When this is detected by the analysis routine, an overlay plot where each data series is time aligned around the dinner meal would be appropriate. The problem data series may be highlighted and when the cursor is placed over it, more information about the meal may be presented. Then, the HCP can have a discussion with the patient about these specific meals and perhaps find out that the patient is having a problem counting carbs for a specific type of meal, for instance.

A final example is where the analysis routine detects that there is not enough glucose measurements to adequately detect adverse conditions. Then, the graphic may be a bar chart showing average BG measurements per each day over the period of analysis. The HCP can then have a discussion about the importance of taking frequent measurements.

The process steps for this invention, in certain embodiments, would be as follows: 1) retrieve stored data associated with diabetes management for a specific patient, such as glucose readings, insulin delivery data, meal data, etc.; 2) analyze the data based on one or more predefined conditions to check; 3) for each condition detected, output a specific graphical report that best demonstrates that condition.

The process steps for this invention, in another embodiment, would be as follows: 1) retrieve stored data associated with diabetes management for a specific patient, such as glucose readings, insulin delivery data, meal data, etc.; 2) analyze the data based on one or more predefined conditions to check; 3) for the pre-defined highest priority condition detected, output a specific graphical report that best demonstrates that condition; 4) provide a graphical means for the user to select any lower priority conditions detected and output the corresponding specific graphical report that best demonstrates that condition.

This invention would preferably be implemented on a PC software program, but may also be incorporated into a handheld device, that may interact with glucose measurement and/or insulin delivery.

Software Application for Providing a Single Page Integrated Multi-Day Report

In certain embodiments, there is provide a method for creating a single page integrated multi-day report. For example, in certain embodiments, there is provided a multi-day report that integrates insulin, glucose, exercise, meal, and medication details into one single, readable, page. This integrated multi-day report concept contains all the contextual glucose, insulin, meal, exercise, and medication information and presented over a period of multiple days in an iconic display. The iconic approach to present different events also enhances port comprehension. The advantage of a single multi-day report is that more contractual information in a single page will aid the interpretation and treatment of diabetes.

Software Application for Providing Recommendations for Glucose Monitor Type Based on Simulations In certain embodiments, there is provided a method for recommending glucose monitor type based on simulations.

A therapy calculator determines optimal glucose response model parameters based on glucose history, meal history, and insulin delivery history. These parameters can be loaded into an enhanced bolus calculator that accounts for this model and provides the patient with more accurate bolus recommendations. Software can then be used to simulate expected glucose response to treatment events for different types of glucose measurement devices; e.g., SMBG, GoD, CGM, or blind (no glucose measurement device is used).

As such, there is provided a process to use these simulations to recommend to a HCP the appropriate glucose measurement device to use. The more effective methods typically are also more costly and inconvenient, so the natural choice of device is to use the least costly and inconvenient, that can still effectively treat the patient's condition. The least effective is generally "blind" or no glucose measurement device, then SMBG, GoD, and CGM are progressively more effective, in that order.

The simulations are based on multiple meal and/or correction events that have been recorded. The therapy calculator uses the glucose history, meal information and insulin delivery information around these events to calculate the optimal parameters specific to the patient for the model. The simulation for the "blind" scenario then assumes that each meal bolus event is based only on meal information not glucose. Glucose correction events, for instance for a CGM simulation where a hyper alarm is indicated, would not assume a correction occurred for the blind scenario.

The simulation for the SMBG scenario assumes that for each meal bolus event, the bolus is now based on the meal information and the glucose level but not the trend. For correction events, it should be assumed that like the blind situation, these are not accounted for.

The GoD simulation scenario is much like that for SMBG except that glucose trend can be taken into account for the bolus calculation. Alternatively, the GoD and SMBG simulation scenarios may take into account extreme low and high glucose events assuming that patients may sense these and would initiate a glucose reading.

The CGM simulation will assume that whenever the glucose exceeds a high or low threshold, that a correction bolus occurred, which is based on glucose level and trend. Alternative, corrections based on projected high or low thresholds may trigger a correction event. Finally, correction events may be associated with actual correction events from the data.

The process would generate these multiple simulations based on past glucose, meal and insulin history. Metrics may be generated from these simulation results to provide an indication of acceptable glucose control—the least expensive and inconvenient glucose measurement device that provides an adequate simulated glucose management metric should be selected for the patient. Alternatively, or in conjunction with metrics), the simulations may be presented to the HCP so they can visually determine the appropriate device for that patient.

The above invention may also be extended to non-insulin medication treatments, diet/exercise treatments, etc.

Software Application for Providing Extension of Therapy Calculator to Treatments Beyond Insulin Delivery In certain embodiments, there is provided methods for providing an extension of the therapy calculator to treatments beyond insulin delivery.

A therapy calculator generally records insulin delivery data, glucose measurements, and food intake (and potentially other data relevant to diabetes) for a patient for some time, transfers data to a processor that uses it along with a model of the patient's physiology, and calculates key model parameters that would be used to optimize subsequent insulin treatment such that glucose levels would stay level. Specifically, the treatment adjustments may include adjustments to the amount of insulin needed to compensate for meals or glucose level corrections. These adjustments may include other factors such as when to bolus relative start of meal, type of bolus and variations related to the type of meal.

Provided herein are methods of extending the above-described design to other treatments for diabetes, and for treatments for other deceases. Specifically in regards to insulin treatment, these methods may be used to inform a patient of how much insulin to take via other mechanisms, such as oral or nasal, for example. A physiological model is needed for the specific type of insulin medication/delivery, and one or more parameters are identified related to insulin amount or timing or any other parameter type in which the patient may use to determine how to administer the drug. These parameters may be utilized by the patient directly, such as to determine how much to inject or ingest, or these parameters may be loaded (manually or automatically) into a device that calculates how much insulin should be delivered. The amount may be delivered manually with an amount indicated by a bolus calculator, or remotely by a device designed for convenient user interaction, or automatically by a system that is programmed to delivery this amount at a various times (for instance the same time(s) every day or at times relative to other events such as meals, meal announcements, glucose level/profile indicators, etc.).

The bolus calculator may take into account one or more CGM data in order to better compensate for glucose rate-of-change. To do this, the bolus calculator may incorporate the same or similar model as the therapy calculator, where some of the model parameters are identified by the therapy calculator. These parameters would not need to be such that they are usable directly by the patient (e.g., insulin-to-carb ratio or insulin-to-glucose ratio) but may be combinations of these. The bolus calculator may be able to utilize the identified parameters to provide an optimal dose information to the patient.

In certain embodiments, the methods may be extended to drug therapies other than insulin. For any drug that induces a physiological response with a means to measure one or more relevant patient's conditions, a model can be developed to describe this response. Some model parameters can be considered constant for a population and others can be identified specifically for that patient for that point in time. Additionally, some parameters may be identified for the patient at that time, then subsequently held constant, while other parameters are identified at a later time. The parameters may be related to drug amount, or time of day timing, or timing related to some patient condition indicator. The parameters may be utilized directly by the patient, or programmed into a device that provides delivery information, allows the patient a remote means to initiate delivery, or can be programmed for automatic delivery.

Integration with Medication Delivery Devices and/or Systems

In some embodiments, the analyte measurement systems disclosed herein may be included in and/or integrated with, a medication delivery device and/or system, e.g., an insulin pump module, such as an insulin pump or controller module thereof, or insulin injection pen. In some embodiments the analyte measurement system is physically integrated into a medication delivery device. In other embodiments, an analyte measurement system as described herein may be configured to communicate with a medication delivery device or another component of a medication delivery system. Additional information regarding medication delivery devices and/or systems, such as, for example, integrated systems, is provided in U.S. Patent Application Publication No. 2006/0224141, published on Oct. 5, 2006, entitled "Method and System for Providing Integrated Medication Infusion and Analyte Monitoring System", and U.S. Patent Application Publication No. 2004/0254434, published on Dec. 16, 2004, entitled "Glucose Measuring Module and Insulin Pump Combination," the disclosure of each of which is incorporated by reference herein in its entirety. Medication delivery devices which may be provided with analyte measurement system as described herein include, e.g., a needle, syringe, pump, catheter, inhaler, transdermal patch, or combination thereof. In some embodiments, the medication delivery device or system may be in the form of a drug delivery injection pen such as a pen-type injection device incorporated within the housing of an analyte measurement system. Additional information is provided in U.S. Pat. Nos. 5,536,249 and 5,925,021, the disclosures of each of which are incorporated by reference herein in their entirety.

The embodiments presented herein provide further advantages such as: the ability to upgrade strip port modules as new test strip technologies evolve; the ability to clean or sterilize a strip port module; and the ability to allow users to replace strip port modules without returning the entire measurement system to the manufacture.

Certain embodiments relate to in vivo (e.g., continuous monitoring) systems. A continuous monitoring system typically includes a sensor that is worn or placed below the skin, a transmitter that collects glucose information from the sensor, and a receiver that collects the information from the transmitter. The sensor can collect glucose level information continuously, periodically, or at other intervals. Advantageously, a user is relieved from having to repeatedly lance his or her body to collect a blood sample once the sensor is inserted, although the sensor (e.g., an electrochemical sensor that is inserted into a body) can be replaced. U.S. Pat. No. 6,175,752, which is hereby incorporated by reference in its entirety, discloses additional examples of a continuous monitoring system.

Embodiments of the invention relate to components of a continuous monitoring system that may be replaceable. In certain embodiments, the interface between the sensor and the transmitter may become contaminated. The transmitter or sensor control unit, for example, may have an interface with the sensor that has been molded to form a barrier between the transmitter's contacts and circuitry internal to the transmitter. This allows the transmitter's contacts to be washed without damaging the transmitter's circuitry. Alternatively, the contacts may be included in a replaceable port that can be replaced as needed. Similarly, the interface on the sensor may be molded to form a barrier to contamination or be replaceable.

Embodiments of the invention further extend to kits. Examples of a kit include a measurement device with one or more strip connectors. In some kits, different strip connectors or ports for different types of strips may be included. This allows the measurement device to be used with different strip form factors. The kits may also include a plurality of test strips. In certain examples, the measurement device may be configured for use with disposable test strips as well as with test strips that are configured for continuous monitoring systems. Thus, the measurement device may include a receiver to receive information from a transmitter that collects glucose information from an inserted sensor. The measurement device may also include a strip connector, such as those disclosed herein, for use with single use test strips.

Analyte Test Strips

Analyte test strips for use with the present devices can be of any kind, size, or shape known to those skilled in the art; for example, FREESTYLE® and FREESTYLE LITE™ test strips, as well as PRECISION™ test strips sold by ABBOTT DIABETES CARE Inc. In addition to the embodiments specifically disclosed herein, the devices of the present disclosure can be configured to work with a wide variety of analyte test strips, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. patent application Ser. No. 12/102,374, filed Apr. 14, 2008, and U.S. Patent Application Publication No. 2009/0095625; U.S. Pat. Nos. 6,616,819; 6,143,164; 6,592,745; 6,071,391 and 6,893,545; the disclosures of each of which are incorporated by reference herein in their entirety.

Calculation of Medication Dosage

In certain embodiments, the analyte measurement system may be configured to measure the blood glucose concentration of a patient and include instructions for a long-acting insulin dosage calculation function. Periodic injection or administration of long-acting insulin may be used to maintain a baseline blood glucose concentration in a patient with Type-1 or Type-2 diabetes. In one aspect, the long-acting medication dosage calculation function may include an algorithm or routine based on the current blood glucose concentration of a diabetic patient, to compare the current measured blood glucose concentration value to a predetermined threshold or an individually tailored threshold as determined by a HCP or other treating professional to determine the appropriate dosage level for maintaining the baseline glucose level. In certain embodiments, the long-acting insulin dosage calculation function may be based upon LANTUS® insulin, available from Sanofi-Aventis, also known as insulin glargine. LANTUS® is a long-acting insulin that has up to a 24 hour duration of action. Other types of long-acting insulin include Levemir® insulin available from NovoNordisk. Examples of such embodiments are described in in US Published Patent Application No. 2010/01981142, the disclosure of which is incorporated herein by reference in its entirety.

Strip Port Configured to Receive Test Strips for Different Analytes

In another embodiment, there is provided an analyte measurement system for multichemistry testing. The test strips are for chemical analysis of a sample, and are adapted for use in combination with a measuring device having a test port and capable of performing a multiplicity of testing functionalities. Each type of test strip corresponds to at least one of the testing functionalities, and at least some types of test strips have indicators of the testing functionality on them. The test port is adapted for use in combination with a multiplicity of different types of test strips and includes a sensor capable of specifically interacting with the indicator(s) on the test strips, thereby selecting at least one of the multiplicity of testing functionalities corresponding to the type of test strip. Such system would include a strip port that can be used to read a test strip for glucose and a test strip for ketone bodies. Examples of such embodiment are provided in U.S. Pat. No. 6,773,671, which is incorporated herein by reference in its entirety.

Strip Port Configured to Receive Test Strips Having Different Dimensions and/or Electrode Configurations In some embodiments, an analyte measurement system as described herein includes a strip port configured to receive test strips having different dimensions and/or electrode configurations, e.g., as described in the U.S. patent application Ser. No. 12/695,947 filed on Jan. 28, 2010, and entitled "Universal Test Strip Port", the disclosure of which is incorporated by reference herein in its entirety.

Implanted Analyte Sensor

In some embodiments, an analyte measurement system as described herein may include an implanted or partially implanted analyte sensor, e.g., a system including an implanted or partially implanted glucose sensor (e.g., a continuous glucose sensor). A system including an implanted or partially implanted glucose sensor may include an analyte measurement system as described herein, which is configured to receive analyte data from the implanted or partially implanted glucose sensor either directly or through an intermediate device, e.g., an RF-powered measurement circuit coupled to an implanted or partially implanted analyte sensor. In some embodiments, where an analyte measurement system according to the present disclosure is integrated with an implanted sensor, the analyte measurement system does not include a strip port for receiving an analyte test strip. In certain embodiments, the analyte measurement system may be used to calibrate the analyte monitoring system, e.g., using one point calibration or other calibration protocol. For additional information, see U.S. Pat. No. 6,175,752, the disclosure of which is incorporated by reference herein in its entirety. In some embodiments, the analyte measurement system may be configured to communicate with the implanted or partially implanted analyte sensor via Radio Frequency Identification (RFID) and provide for intermittent or periodic interrogation of the implanted analyte sensor.

Exemplary analyte monitoring systems that may be utilized in connection with the disclosed analyte measurement system include those described in U.S. Pat. Nos. 7,041,468; 5,356,786; 6,175,752; 6,560,471; 5,262,035; 6,881,551; 6,121,009; 7,167,818; 6,270,455; 6,161,095; 5,918,603; 6,144,837; 5,601,435; 5,822,715; 5,899,855; 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,461,496; 6,503,381; 6,591,125; 6,616,819; 6,618,934; 6,676,816; 6,749,740; 6,893,545; 6,942,518; 6,514,718; 5,264,014; 5,262,305; 5,320,715; 5,593,852; 6,746,582; 6,284,478; 7,299,082; U.S. patent application Ser. No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Application Publication No. 2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; US patent Application Publication No. 2010/0198034; and U.S. Provisional Application No. 61/149,639 titled "Compact On-Body Physiological Monitoring Device and Methods Thereof", the disclosures of each of which are incorporated herein by reference in their entirety.

Communication Interface

As discussed previously herein, an analyte measurement system according to the present disclosure can be configured to include a communication interface. In some embodiments, the communication interface includes a receiver and/or transmitter for communicating with a network and/or another device, e.g., a medication delivery device and/or a patient monitoring device, e.g., a continuous glucose monitoring device. In some embodiments, the communication interface is configured for communication with a health management system, such as the CoPilot™ system available from Abbott Diabetes Care Inc., Alameda, Calif.

The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In certain embodiments, the communication interface is configured to include one or more communication ports, e.g., physical ports or interfaces such as a USB port, an RS-232 port, or any other suitable electrical connection port to allow data communication between the analyte measurement system and other external devices such as a computer terminal (for example, at a physician's office or in hospital environment), an external medical device, such as an infusion device or including an insulin delivery device, or other devices that are configured for similar complementary data communication.

In certain embodiments, the communication interface is configured for infrared communication, Bluetooth® communication, or any other suitable wireless communication protocol to enable the analyte measurement system to communicate with other devices such as infusion devices, analyte monitoring devices, computer terminals and/or networks, communication enabled mobile telephones, personal digital assistants, or any other communication devices which the patient or user of the analyte measurement system may use in conjunction therewith, in managing the treatment of a health condition, such as diabetes.

In certain embodiments, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In certain embodiments, the analyte measurement system is configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen. With such an arrangement, the user can control the analyte measurement system indirectly by interacting with the user interface(s) of the server device, which in turn interacts with the analyte measurement system across a wireless link.

In some embodiments, the communication interface is configured to automatically or semi-automatically communicate data stored in the analyte measurement system, e.g., in an optional data storage unit, with a network or server device using one or more of the communication protocols and/or mechanisms described above.

Input Unit

As discussed previously herein, an analyte measurement system according to the present disclosure can be configured to include an input unit and/or input buttons coupled to the housing of the analyte measurement system and in communication with a controller unit and/or processor. In some embodiments, the input unit includes one or more input buttons and/or keys, wherein each input button and/or key is designated for a specific task. Alternatively, or in addition, the input unit may include one or more input buttons and/or keys that can be 'soft buttons' or 'soft keys'. In the case where one or more of the input buttons and/or keys are 'soft buttons' or 'soft keys', these buttons and/or keys may be used for a variety of functions. The variety of functions may be determined based on the current mode of the analyte measurement system, and may be distinguishable to a user by the use of button instructions shown on an optional display unit of the analyte measurement system. Yet another input method may be a touch-sensitive display unit, as described in greater detail below.

In addition, in some embodiments, the input unit is configured such that a user can operate the input unit to adjust time and/or date information, as well as other features or settings associated with the operation of an analyte measurement system.

Display Unit

As discussed previously herein, in some embodiments, an analyte measurement system according to the present disclosure includes an optional display unit or a port for coupling an optional display unit to the analyte measurement system. The display unit is in communication with a control unit and/or processor and displays the analyte test strip signals and/or results determined from the analyte test strip signals including, for example, analyte concentration, rate of change of analyte concentration, and/or the exceeding of a threshold analyte concentration (indicating, for example, hypo- or hyperglycemia).

The display unit can be a dot-matrix display, e.g., a dot-matrix LCD display. In some embodiments, the display unit includes a liquid-crystal display (LCD), thin film transistor liquid crystal display (TFT-LCD), plasma display, light-emitting diode (LED) display, seven-segment display, E-ink (electronic paper) display or combination of two or more of the above. The display unit can be configured to provide, an alphanumeric display, a graphical display, a video display, an audio display, a vibratory output, or combinations thereof. The display can be a color display. In some embodiments, the display is a backlit display.

The display unit can also be configured to provide, for example, information related to a patient's current analyte concentration as well as predictive analyte concentrations, such as trending information.

In some embodiments an input unit and a display unit are integrated into a single unit, for example, the display unit can be configured as a touch sensitive display, e.g., a touch-screen display, where the user may enter information or commands via the display area using, for example, the user's finger, a stylus or any other suitable implement, and where, the touch sensitive display is configured as the user interface in an icon driven environment, for example.

In some embodiments, the display unit does not include a screen designed to display results visually. Instead, in some embodiments the optional display unit is configured to communicate results audibly to a user of the analyte measurement system, e.g., via an integrated speaker, or via separate speakers through a headphone jack or Bluetooth® headset.

Expanding Menu Item for Improved Readability

In some embodiments, the display unit includes a graphical user interface including a plurality of menu items, wherein the display unit is configured to provide clarification with respect to the meaning of a menu item based on a user's response speed with respect to a user input for the menu item. The menu item may take any of a variety of forms, e.g., text, icon, object or combination thereof.

In certain embodiments, the graphical user interface includes a menu which in turn includes a plurality of selectable menu items. As a user navigates through the menu, e.g., by highlighting or scrolling through individual menu items, a menu item that is either unreadable or incomprehensible to the user may cause the user to pause over a menu item to be selected. In certain embodiments, a choice can be presented to the user, e.g., using a dedicated physical button on an input unit, or a soft key on the menu, that offers further explanation of the item to be selected without actually selecting the item. For example, the graphical user interface can be configured such that after a predetermined period of time a soft key offers an explanation of the menu item to be selected, e.g., by displaying a soft key with the word "MORE", "ADDITIONAL INFORMATION", "EXPAND", "MAGNIFY", "HELP" or a variation thereof displayed thereon.

The pre-determined period of time may be based on a fixed factory preset value, a value set by the user or a health care provider, or through an adaptive mechanism based on an analysis of the user's speed of navigation from past interactions with the graphical user interface. In certain embodiments, the pre-determined period of time is from about 5 to about 20 seconds, e.g., from about 10 to about 15 seconds.

If the offer for clarification and/or additional information is selected, e.g., by pressing the softkey, then the menu item to be selected can be displayed in a "high emphasis" mode, e.g., where the item is displayed as if a magnifying lens is held on top of the selected item. In some embodiments, additional emphasis of the menu item to be selected can be provided, e.g., by making the menu item change color, blink, or increase in size to a pre-determined maximum limit.

Support for on-Demand Analyte Determination Using an Analyte Sensor

In some embodiments, an analyte measurement system according to the present disclosure is further configured to receive analyte concentration data and/or signals indicative of an analyte concentration from an analyte sensor, e.g., an implanted or partially implanted analyte sensor or a radio-frequency (RF)-powered measurement circuit coupled to an implanted or partially implanted analyte sensor. In some embodiments, the analyte sensor is a self-powered analyte sensor. An analyte measurement system according to the present disclosure may include software configured to analyze signals received from the analyte sensor. Additional information related to self-powered analyte sensors and methods of communicating therewith are provided in U.S. Patent Application Publication No. 2010/0213057, the disclosure of which is incorporated by reference herein in its entirety.

Analytes

A variety of analytes can be detected and quantified using the disclosed analyte measurement system. Analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. Nos. 6,281,006 and 6,638,716, the disclosures of each of which are incorporated by reference herein in their entirety.

CONCLUSION

It should be understood that techniques introduced above can be implemented by programmable circuitry programmed or configured by software and/or firmware, or they can be implemented entirely by special-purpose "hardwired" circuitry, or in a combination of such forms. Such special-purpose circuitry (if any) can be in the form of, for example, one or more application-specific integrated circuits (ASICS), programmable logic devices (PLDs), field-programmable gate arrays (FPGAs), etc.

Software or firmware implementing the techniques introduced herein may be stored on a computer-readable storage medium and may be executed by one or more general-purpose or special-purpose programmable microprocessors. A "computer-readable medium", as the term is used herein, includes any mechanism that can store information in a form accessible by a computer (a computer may be, for example, a personal computer, network device, cellular phone, personal digital assistant (PDA), manufacturing took, any device with one or more processors, etc.). For example, a computer-accessible medium includes recordable/non-recordable media (e.g., read-only memory (ROM); random access memory (RAM); magnetic disk storage media; optical storage media; flash memory devices; etc.), etc.

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

The detailed description of the figures refers to the accompanying drawings that illustrate an exemplary embodiment of an analyte measurement system. Other embodiments are possible. Modifications may be made to the embodiment described herein without departing from the spirit and scope of the present invention. Therefore, the following detailed description is not meant to be limiting.

Certain embodiments presented herein relate to electrical interfaces in measurement devices. Measurement devices often have electrical interfaces that allow them to electrically connect with another device or apparatus and perform an analysis of an analyte. A device that measures blood glucose levels, for example, includes electrical interfaces that allow the device to measure the blood glucose level from a small blood sample.

What is claimed is:

1. A computer-implemented method for hypoglycemia risk determination and treatment recommendation, the method comprising:
   collecting, by one or more computing devices, a plurality of analyte concentration measurements generated by an in vivo analyte monitoring system, the in vivo analyte monitoring system comprising at least a portion of an analyte sensor in contact with a bodily fluid of a user;
   executing, by one or more processors of the one or more computing devices, software configured to perform the following steps:
   (a) determining a first median value for the plurality of analyte concentration measurements corresponding to a first time of day period;
   (b) determining a first variability value for the plurality of analyte concentration measurements corresponding to the first time of day period;
   (c) determining, with reference to a data space defined by a range of median analyte concentration values and a range of variability analyte concentration values where the data space comprises a plurality of zones, if a first zone of the plurality of zones includes the first median value and the first variability value, wherein the first zone is associated with a risk of hypoglycemia, and
   (d) if it is determined that the first median value and the first variability value are included in the first zone, then outputting either a representation of the first zone or a treatment recommendation based on the first zone, wherein the treatment recommendation is related to a medication adjustment or food intake.

2. The method of claim 1, wherein the first zone is defined by a hypoglycemia risk boundary, wherein the first zone comprises a plurality of median values that are less than the hypoglycemia risk boundary.

3. The method of claim 2, wherein the hypoglycemia risk boundary is either a straight hypoglycemia risk line or a curved hypoglycemia risk line.

4. The method of claim 1, wherein the representation of the identified first zone is output in (d), wherein the representation indicates hypoglycemia risk.

5. The method of claim 1, wherein the treatment recommendation is output in (d).

6. The method of claim 2, wherein the first variability value is a variability of the analyte concentration measurements in a range from the first median value to a tenth percentile value less than the median value, wherein when the plurality of analyte measurement concentrations are sorted from a highest to a lowest value, the tenth percentile value is the value in which about ninety percent of the analyte measurement concentrations are above the tenth percentile value and about ten percent of the analyte measurement concentrations are below the tenth percentile value.

7. The method of claim 2, wherein the first variability value is a variability of the analyte concentration measurements in a range from the first median value to an amount less than the first median value when the analyte concentration measurements are sorted from a highest to a lowest value.

8. The method of claim 2, further comprising adjusting, with the software executed by the one or more processors, the hypoglycemia risk boundary prior to determining if the first zone, from the plurality of zones, includes the first median value and the first variability value.

9. The method of claim 1, wherein the analyte concentration measurements comprise glucose data.

10. The method of claim 1, wherein the software, when executed by the one or more processors of the one or more computing devices, is further configured to perform the following steps:
    (e) determining a second median value for a plurality of analyte concentration measurements corresponding to a second time of day period and a second variability value for the plurality of analyte concentration measurements corresponding to the second time of day period;
    (f) determining with reference to the data space, if a second zone from the plurality of zones includes the second median value and the second variability value, wherein the second zone is associated with a risk of hypoglycemia, and
    (g) if it is determined that the second median value and the second variability value are included in the second zone, outputting a representation of the second zone.

11. The method of claim 10, further comprising:
    displaying a first treatment recommendation to the user based on the first zone for the first median value and the first variability value; and
    displaying a second treatment recommendation to the user based on the second zone for the second median value and the second variability value.

12. A computer-implemented method for hypoglycemia risk determination and treatment recommendation, the method comprising:

collecting, by one or more computing devices, a plurality of analyte concentration measurements generated by an in vivo analyte monitoring system, the in vivo analyte monitoring system comprising at least a portion of an analyte sensor that is in contact with a bodily fluid of a user;

executing, by one or more processors of the one or more computing devices, software configured to perform the following steps:
- (a) determining a first central tendency value for the plurality of analyte concentration measurements corresponding to a first time of day period;
- (b) determining a first variability value for the plurality of analyte concentration measurements corresponding to the first time of day period;
- (c) determining, with reference to a data space defined by a range of central tendency values and a range of variability values where the data space comprises a plurality of zones, if a first zone of the plurality of zones includes the first central tendency value and the first variability value, wherein the first zone is associated with a risk of hypoglycemia, and
- (d) if it is determined that the first central tendency value and the first variability value are included in the first zone, outputting either a representation of the first zone or a treatment recommendation based on the first zone, wherein the treatment recommendation is related to a medication adjustment or food intake.

13. The method of claim 12, wherein the first zone is defined by a hypoglycemia risk boundary, wherein the first zone includes a plurality of central tendency values that are less than the hypoglycemia risk boundary.

14. The method of claim 12, wherein the representation indicates hypoglycemia risk.

15. The method of claim 13, further comprising displaying a treatment recommendation to the user based on the identified first zone.

16. The method of claim 13, wherein the first variability value is a variability of the analyte concentration values in a range from the first central tendency value to a tenth percentile value less than the first central tendency value, wherein when the plurality of analyte measurement concentrations are sorted from a highest to lowest central tendency value, the tenth percentile value is the value in which about ninety percent of the central tendency values are above the tenth percentile value and about ten percent of the central tendency values are below the tenth percentile value.

17. The method of claim 13, wherein the first variability value is a variability of the analyte concentration values in a range from the first central tendency value to an amount less than the first central tendency value when the central tendency values are sorted from a highest to a lowest value.

18. The method of claim 13, further comprising adjusting, with the software executed by the one or more processors, the hypoglycemia risk boundary prior to determining if the first one zone, from the plurality of zones, includes the first central tendency value and the first variability value.

19. The method of claim 12, wherein the analyte concentration measurements comprise glucose data.

20. The method of claim 12, wherein the software, when executed by the one or more processors of the one or more computing devices, is further configured to perform the following steps:
- (e) determining a second a central tendency value for the plurality of analyte concentration measurements corresponding to a second time of day period and a second variability value for the plurality of analyte concentration measurements corresponding to the second time of day period;
- (f) determining, with reference to the data space, if a second zone from the plurality of zones includes the second central tendency value and the second variability value, wherein the second zone is associated with a risk of hypoglycemia; and
- (g) outputting a representation of the identified second zone if it is determined that the second central tendency value and the second variability value are included in the second zone.

21. The method of claim 20, further comprising:
displaying a first treatment recommendation to the user based on the first zone for the first central tendency value and the first variability value; and
displaying a second treatment recommendation to the user based on the second zone for the second central tendency value and the first variability value.

22. The method of claim 1, wherein the one or more computing devices comprise one or more cloud-based servers.

23. The method of claim 1, wherein the one or more computing devices comprise a smart phone.

24. The method of claim 1, wherein the representation of the first zone is output in (d).

25. A system for hypoglycemia risk determination and treatment recommendation, the system comprising:
one or more in vivo analyte monitoring systems, each comprising at least a portion of an analyte sensor in contact with a bodily fluid of a user;
one or more computing devices configured to collect a plurality of analyte concentration measurements generated by the one or more in vivo analyte monitoring systems, wherein the one or more computing devices comprises one or more processors and memory coupled thereto, the memory storing software that, when executed by the one or more processors, cause the one or more processors to perform the following steps:
- (a) determine a first median value for the plurality of analyte concentration measurements corresponding to a first time of day period;
- (b) determine a first variability value for the plurality of analyte concentration measurements corresponding to the first time of day period;
- (c) determine, with reference to a data space defined by a range of median analyte concentration values and a range of variability analyte concentration values where the data space comprises a plurality of zones, if a first zone of the plurality of zones includes the first median value and the first variability value, wherein the first zone is associated with a risk of hypoglycemia, and
- (d) if it is determined that the first median value and the first variability value are included in the first zone, then output a treatment recommendation based on the first zone, wherein the treatment recommendation is related to a medication adjustment or food intake.

26. The system of claim 25, wherein the analyte concentration measurements comprise glucose data.

27. The system of claim 25, wherein the first zone is defined by a hypoglycemia risk boundary, wherein the first zone comprises a plurality of median values that are less than the hypoglycemia risk boundary.

* * * * *